(12) United States Patent
Celik et al.

(10) Patent No.: US 11,485,786 B2
(45) Date of Patent: Nov. 1, 2022

(54) ANTI-ALPHA-V INTEGRIN ANTIBODY FOR THE TREATMENT OF FIBROSIS AND/OR FIBROTIC DISORDERS

(71) Applicant: Merck Patent GmbH, Darmstadt (DE)

(72) Inventors: Ilhan Celik, Zwingenberg (DE); Eike Staub, Darmstadt (DE); Miriam Urban, Leidersbach (DE); Sabine Raab, Rosbach (DE); Eileen Samy, Arlington, MA (US); Andrew Bender, Reading, MA (US); Georgianna Higginbotham, Tewksbury, MA (US); Yin Wu, Andover, MA (US); Daigen Xu, Westford, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/541,650

(22) Filed: Aug. 15, 2019

(65) Prior Publication Data

US 2020/0002424 A1    Jan. 2, 2020

Related U.S. Application Data

(63) Continuation of application No. 15/778,615, filed as application No. PCT/EP2016/001970 on Nov. 22, 2016, now abandoned.

(60) Provisional application No. 62/258,626, filed on Nov. 23, 2015.

(30) Foreign Application Priority Data

Apr. 12, 2016 (EP) .................................... 16164879

(51) Int. Cl.
| | |
|---|---|
| A61K 39/00 | (2006.01) |
| A61K 39/395 | (2006.01) |
| C07K 16/28 | (2006.01) |
| C12Q 3/00 | (2006.01) |
| A61P 17/02 | (2006.01) |
| A61P 11/00 | (2006.01) |
| G01N 33/543 | (2006.01) |

(52) U.S. Cl.
CPC ........ C07K 16/2848 (2013.01); A61K 39/395 (2013.01); A61P 11/00 (2018.01); A61P 17/02 (2018.01); C07K 16/2839 (2013.01); C12Q 3/00 (2013.01); G01N 33/54366 (2013.01); A61K 2039/505 (2013.01); C07K 2317/24 (2013.01); C07K 2317/73 (2013.01); C07K 2317/76 (2013.01)

(58) Field of Classification Search
None
See application file for complete search history.

(56) References Cited

U.S. PATENT DOCUMENTS

| | | |
|---|---|---|
| 5,753,230 A | 5/1998 | Brooks et al. |
| 5,766,591 A | 6/1998 | Brooks et al. |
| 5,985,278 A | 11/1999 | Mitjans et al. |
| 6,001,961 A | 12/1999 | Jonczyk et al. |
| 8,562,986 B2 | 10/2013 | Goodman et al. |
| 2010/0254977 A1 | 10/2010 | Goodman et al. |
| 2014/0086908 A1 | 3/2014 | Hoffmann et al. |
| 2017/0218070 A1 | 8/2017 | Hoffmann et al. |

FOREIGN PATENT DOCUMENTS

| | | |
|---|---|---|
| EP | 0 719 859 | 7/1996 |
| EP | 0 770 622 | 5/1997 |
| EP | 0 531 472 | 8/2003 |
| WO | 2007/008712 | 1/2007 |
| WO | 2009/010290 | 1/2007 |
| WO | 2010/008543 | 1/2010 |
| WO | 2013/148232 | 10/2013 |
| WO | 2014/138906 | 9/2014 |

OTHER PUBLICATIONS

Elez et al. Abituzumab combined with cetuximab plus irinotecan versus cetuximab plus irinotecan alone for patients with KRAS wild-type metastatic colorectal cancer: the randomised phase I/II POSEIDON trial. Annals of Oncology 26: 132-140, 2015. Published online Oct. 15, 2014 (Year: 2015).*
Katsumoto et al. Blocking TGFβ via Inhibition of the αvβ6 Integrin: A Possible Therapy for Systemic Sclerosis Interstitial Lung Disease. International Journal of Rheumatology vol. 2011, 7 pages. (Year: 2011).*
Lafyatis R. Transforming growth factor β-at the centre of systemic sclerosis. Nat Rev Rheumatol. Dec. 2014;10(12):706-19. Epub Aug. 19, 2014 (Year: 2014).*
Agarwal et al. Integrins and cadherins as therapeutic targets in fibrosis. Front Pharmacol., Jun. 3, 2014;5:131. (Year: 2014).*
Nakerakanti et al. The Role of TGF-β Receptors in Fibrosis. The Open Rheumatology Journal, 2012, 6, (Suppl 1: M12) 156-162. (Year: 2012).*
Khanna et al. STRATUS: A Phase II Study of Abituzumab in Patients With Systemic Sclerosis-associated Interstitial Lung Disease . J Rheumatol. Aug. 2021;48(8): 1295-1298. (Year: 2021).*

(Continued)

*Primary Examiner* — Maher M Haddad
(74) *Attorney, Agent, or Firm* — Grüneberg and Myers PLLC

(57) ABSTRACT

The invention relates to the prophylaxis and/or treatment of fibrosis and/or fibrotic diseases by means of antibodies. Above all, the invention relates to the administration of an anti-alpha-v integrin (receptor) antibody to patients suffering from fibrosis and/or fibrotic diseases, including but not limited to systemic sclerosis (SSc). More specifically, the instant invention relates to the treatment of fibrotic diseases of the skin, lung, heart, liver and/or kidney by means of said antibody. Even more specifically, the instant invention relates to the administration of a recombinant, de-immunized monoclonal antibody targeting αv-integrins patients suffering from systemic sclerosis, including, but not limited to systemic sclerosis of the skin, lung, heart and/or kidney by means of the anti-alpha-v integrin antibody DI17E6 and structural mutants or modifications thereof.

15 Claims, 31 Drawing Sheets

Specification includes a Sequence Listing.

(56) References Cited

OTHER PUBLICATIONS

ClinicalTrials.gov. Abituzumab in SSc-ILD. Apr. 20, 2016. pp. 1-18. (Year: 2016).*

Chen et al. Integrin alphaVbetal inhibition ameliorates liver fibrosis in mice. Journal of Hepatology, (Aug. 2020) vol. 73, Supp. Supplement 1, pp. S522. Abstract No. FRI247. (Year: 2020).*

Aluwihare et al., "Mice that lack activity of αvβ6- and αvβ8-integrins reproduce the abnormalities of Tgfb1- and Tgfb3-null mice" Journal of Cell Science, 122 (2), 2009, pp. 227-232.

Asano et al., "Increased Expression of Integrin αvβ5 Induces the Myofibroblastic Differentiation of Dermal Fibroblasts," American Journal of Pathology, vol. 168, No. 2, 2006, pp. 499-510.

Asano et al., "Increased Expression of Integrin αvβ3 Contributes to the Establishment of Autocrine TGF-β Signaling in Scleroderma Fibroblasts," The Journal of Immunology, vol. 175, 2005, pp. 7708-7718.

Asano et al., "Involvement of αvβ5 Integrin—Mediated Activation of Latent Transforming Growth Factor b1 in Autocrine Transforming Growth Factor β Signaling in Systemic Sclerosis Fibroblasts," Arthritis & Rheumatism, vol. 52, No. 9, 2005, pp. 2897-2905.

Asano et al., "Involvement of αvβ5 Integrin in the Establihnt of Autocrine TGF-β Signaling in Dermal Fibroblasts Derived from Localized Scleroderma," Journal of Investigative Dermatology, vol. 126, 2006, pp. 1761-1769.

Assassi et al., "Clinical and Genetic Factors Predictive of Mortality in Early Systemic Sclerosis" Arthritis & Rheumatism, vol. 61, No. 10, 2009, pp. 1403-1411.

Atabai et al., "Mfge8 diminishes the severity of tissue fibrosis in mice by binding and targeting collagen for uptake by macrophages" Journal of Clinical Investigation, vol. 119, No. 12, 2009, pp. 3713-3722.

Benjamini et al., "Controlling the False Discovery Rate: a Practical and Powerful Approach to Multiple Testing," J. R. Statist. Soc. B, vol. 57, No. 1, 1995, pp. 289-300.

Brown et al. Tolerance of single, but not multiple, amino acid replacements in antibody VH CDR 2: a means of minimizing B cell wastage from somatic . hypermutation? J. Immuno. May 1996, 3285-91. (Year: 1996).

Clinicaltrias.gov. A Study to Determine the Safety, Tolerability, Pharmacokinetics and Dynamic Effects of Different Doses of the Study Drug EMD 525797 in Prostate Cancer. Aug. 11, 2009-Dec. 20, 2010, pp. 1-11. (Year: 2010).

Conroy et al., "αv integrins: key regulators of tissue fibrosis," Cell Tissue Research, vol. 365, 2016, pp. 511-519.

Farina et al., "A Four-Gene Biomarker Predicts Skin Disease in Patients With Diffuse Cutaneous Systemic Sclerosis," Arthritis Rheum., vol. 62, No. 2, pp. 580-588.

Goh et al., "Bronchoalveolar Lavage Cellular Profiles in Patients With Systemic Sclerosis—Associated Interstitial Lung Disease Are Not Predictive of Disease Progression," Arthritis & Rheumatism, vol. 56, No. 6, 2007, pp. 2005-2012.

Henderson et al., "Targeting of αv integrin identifies a core molecular pathway that regulates fibrosis in several organs," Nature Medicine, Vo. 19, No. 12, 2013, pp. 1617-1624.

Hinchcliff et al., "Molecular Signatures in Skin Associated with Clinical Improvement during Mycophenolate Treatment in Systemic Sclerosis,"J. Invest. Dermatol., 133(8), 2013, pp. 1979-1989.

Horan et al., "Partial Inhibition of Integrin αvβ6 Prevents Pulmonary Fibrosis without Exacerbating Inflammation," Am J. Respir. Crit. Care Med., vol. 177, 2008, pp. 56-65.

Jenkins et al., "Ligation of protease-activated receptor 1 enhances αvβ6 integrin—dependent TGF-β activation and promotes acute lung injury," J. Clin. Invest., vol. 116, No. 6, 2006, pp. 1606-1614.

Khanna et al. Ongoing clinical trials and treatment options for patients with systemic sclerosis_associated interstitial lung disease. Rheurnatology (Oxford). Jun. 8, 2018, p. 1-13. (Year: 2018).

Lorenzen et al., "Osteopontin in the development of systemic sclerosis—relation to disease activity and organ manifestation," Rheumatology, vol. 49, 2010, pp. 1989-1991.

Luzina et al., "Occurrence of an Activated, Profibrotic Pattern of Gene Expression in Lung CD8+ T Cells From Scleroderma Patients," Arthritis & Rheumatism, vol. 48, No. 8, 2003, pp. 2262-2274.

Lygoe et al., "αv integrins play an important role in myofibroblast differentiation," Wound Rep. Reg., vol. 12, 2004, pp. 461-470.

Maluish et al. The determination of an immunologically active dose of interferon-gamma in patients with melanoma. J Clin Oncol. Mar. 1988;6(3) :434-45 (Year: 1988).

Meltzer et al., "Bayesian probit regression model for the diagnosis of pulmonary fibrosis: proof-of-principle," BMC Medical Genomics, vol. 4, No. 70, 2011, pp, 1-13.

Milano et al., "Molecular Subsets in the Gene Expression Signatures of Scleroderma Skin" PLoS one, vol. 3, Iss. 7, 2008, e2696, pp. 1-19.

Miller et al. Abetuzumab (DI17E6, EMD 525797) Treatment for Chemotherapy-Naive Patients With Asymptomatic or Mildly Symptomatic Metastatic Castration-Resistant Prostate Cancer (MCRPC): PRIMAry . . . Phase 2 Study Perseus (NCT01380840). Annals of Oncology 25, 4): iv255-iv279, 2014 (Year: 2014).

Mitjans et al., "An anti-αv-integrin antibody that blocks integrin function inhibits the development of a human melanoma in nude mice," Journal of Cell Science, vol. 108, 1995, pp. 2825-2838.

Moon et al., "Synthetic RGDS peptide attenuates lipopolysaccharide-induced pulmonary inflammation by inhibiting integrin signaled MAP kinase pathways," Respiratory Research, vol. 10, No. 18, 2009, pp. 1-15.

Neurohr et al., "Activation of Transforming Growth Factor-p. By the Integrin αv62 8 Delays Epithelial Wound Closure," Am. J. Respir, Cell. Mol. Biol., vol. 35, 2006, pp. 252-259.

Pendergrass et al., "Intrinsic Gene Expression Subsets of Diffuse Cutaneous Systemic Sclerosis Are Stable in Serial Skin Biopsies" J. Invest. Dermatol., vol. 132, Iss. 5), 2012, pp. 1383-373.

Scotton et al., "Increased local expression of coagulation factor X contributes to the fibrotic response in human and murine lung injury" J. Clin. Invest., vol. 119, 2009, pp. 2550-2563.

Smyth, "Linear Models and Empirica Bayes Methods for Assessing Differential Expression in Microarray Experiments," Statistical Applications in Genetics and Molecular Biology, vol. 3, Iss. 1, 2004, pp. 1-25.

Staub, "An Interferon Response Gene Expression Signature Is Activated in a Subset of Medulloblastomas[1,2]," Translational Oncology, vol. 5, No. 4, 2012, pp. 297-304.

Steen et al., "Severe rgan Involvement in Systemic Sclerosis with Diffuse Scleroderma," Arthritis & Rheumatism, vol. 43, No. 11, 2000, pp. 2437-2444.

Su et al., "A gene atlas of the mouse and human protein-encoding transcriptomes," PNAS, vol. 10, No. 16, 2004, pp. 6062-6067.

Takahashi et al., "Role of Osteopontin in the Pathogenesis of Bleomycin-Induced Pulmonary Fibrosis," Am. J. Respir. Cell Mal. Biol., vol. 24, 2001, pp. 264-271.

Uhl et al. Safety, tolerability, and pharmacokinetics of the novel av-integrin antibody EMD 525797 (DI 17E6) in healthy subjects after ascending singe intravenous doses. Invest New Drugs (2014) 32:347-354 (Year: 2014).

Ulmasov et al., "Inhibitors of Arg-Gly-Asp-Binding Integrins Reduce Development of Pancreatic Fibrosis in Mice," Cellular and Molecular Gastroenterology and Hepatology, vol. 2, No. 4, 2016, pp. 500-518.

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).

Wirth et al. A Multicenter Phase 1 Study EM D 525797 (DI 17E6), a Novel Humanized Monoclonal Antibody Targeting av Integrins, in Progressive Castration-resistant Prostate Cancer with Bone Metastases After Chemotherapy. Eur Ural. May 2014;65(5):905-6 ( Year: 2014).

Wirth et al. Phase 1 Study of DI17E6, an Antibody Targeting AV Integrins, in Progressive Castrate-resistant Prostate Cancer With Bone Metastases (mCRPC) After Chemotherapy. European Journal of Cancer , 47(Suppl 1): S488, Sep. 2011. Poster 7012. (Year: 2011).

Wu et al., "Osteopontin in Systemic Sclerosis and Its Role in Dermal Fibrosis," Journal of Investigative Dermatology, vol. 132, 2012, pp. 1605-1614.

(56) References Cited

OTHER PUBLICATIONS

Yang et al. PloS One vol. 7, Iss. 7, 2012, e41994, pp. 1-11.
International Search Report dated May 24, 2017 in PCT/EP2016/001970.
Written Opnion dated May 24, 2017 in PCT/EP2016/001970.
"*International Nonproprietary Names for Pharmaceutical Substances (INN),*" WHO Drug Information, vol. 28, No. 1, 2014, 52 pages.

\* cited by examiner

Figure 1: Abituzumab Blocks Elevated aSMA Expression in H358-Fibroblast and Calu3-Fibroblast Co-cultures
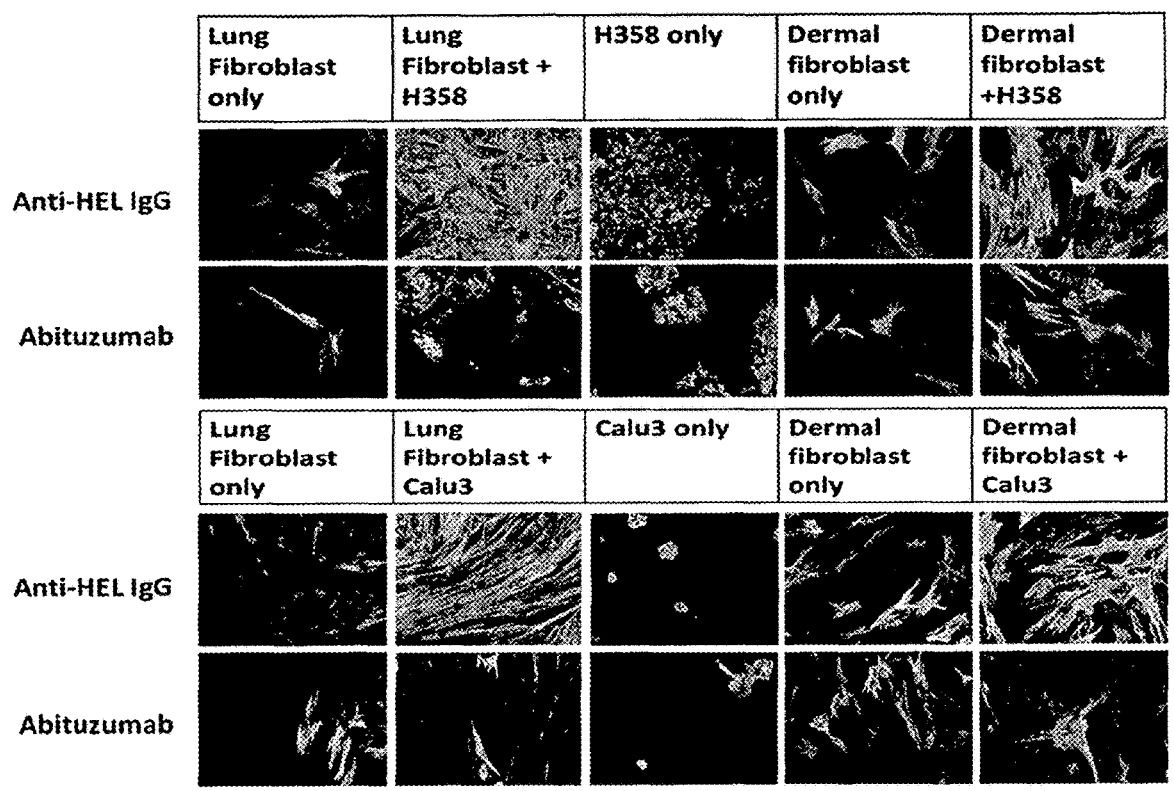

Figure 2: Abituzumab Blocks Elevated Expression of FMT-Related Genes in H358-Fibroblast Co-cultures
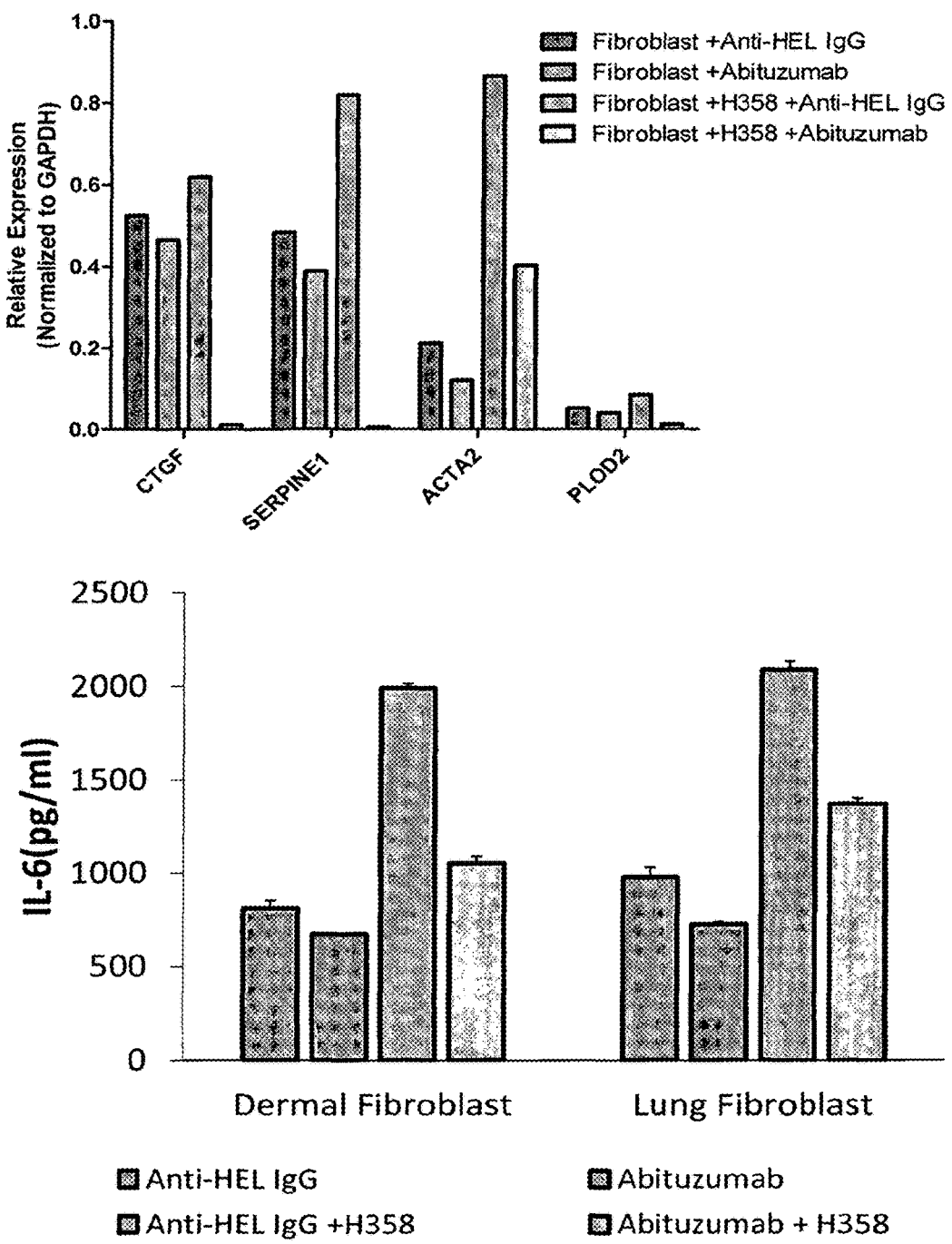

Figure 3: TGF-β Increases Integrins Expression in Human Lung Fibroblast
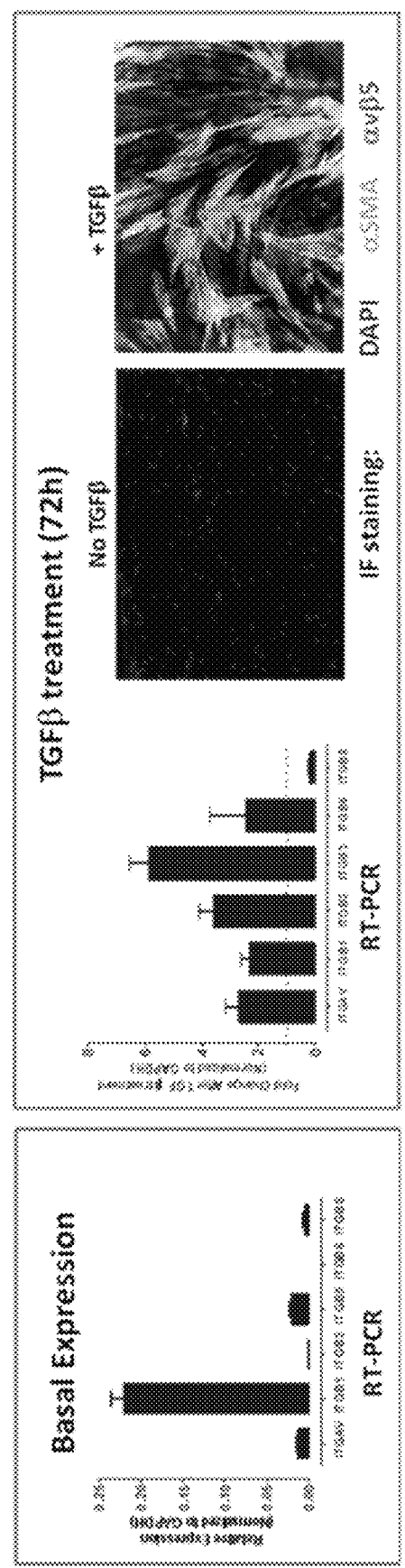

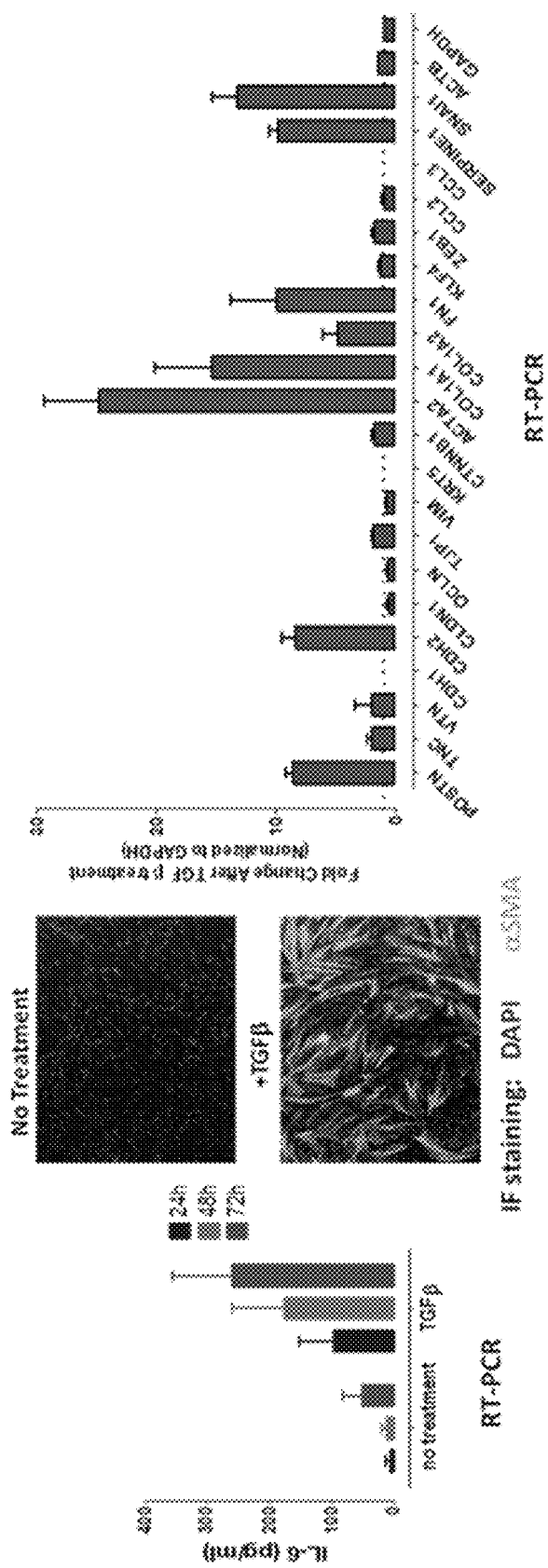
Figure 4: TGF-β Increases aSMA, IL-6 and other Myofibroblast Marker Gene Expression in Lung Fibroblast

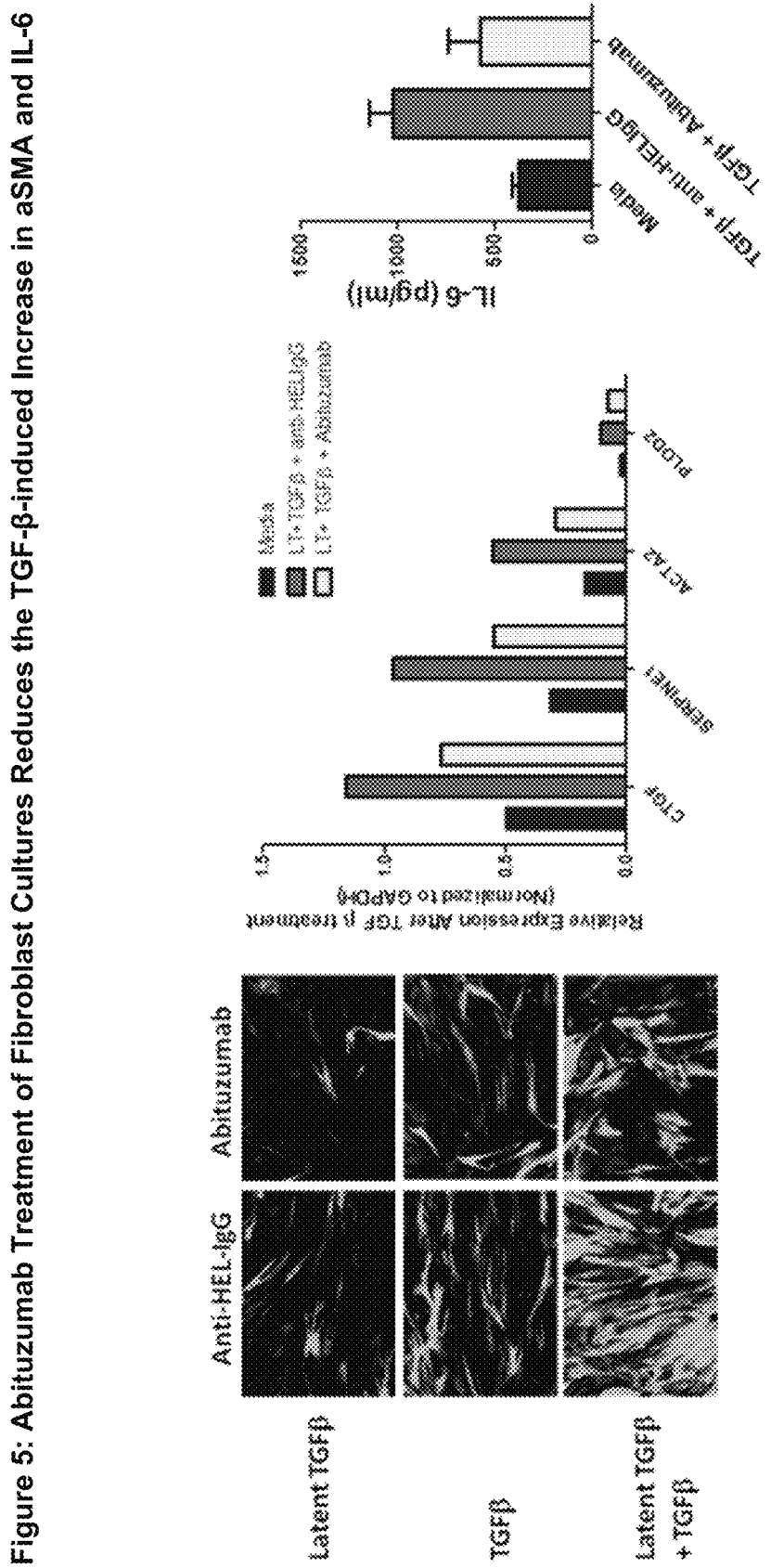
Figure 5: Abituzumab Treatment of Fibroblast Cultures Reduces the TGF-β-induced Increase in aSMA and IL-6

Figure 6: Abituzumab Treatment Reduces TGF-β-induced Collagen Gel Contraction
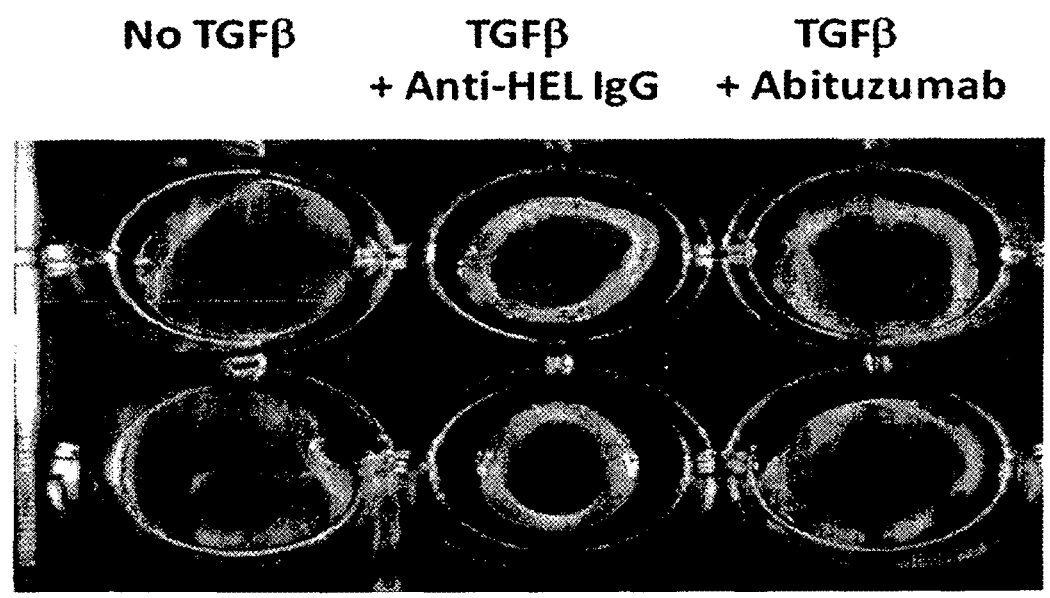

Figure 7: Inhibition of αvβ6 6 binding to LAP by Abituzumab.
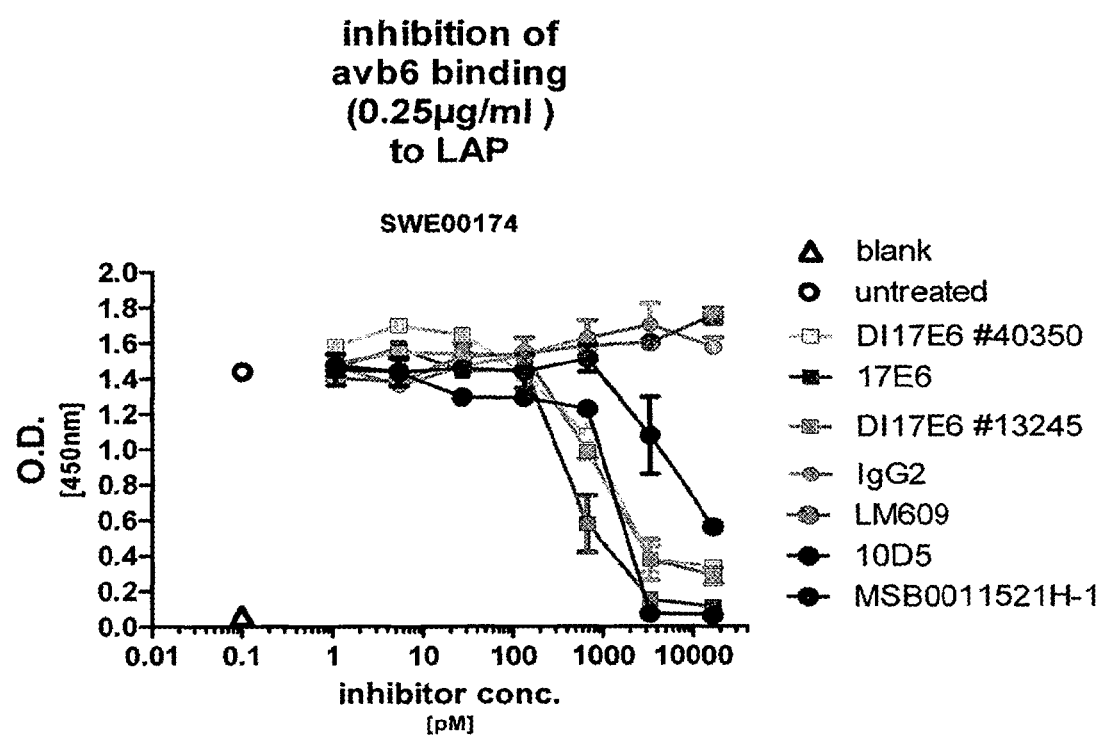

Figure 8: Strategie chart for finding the fibrosis/SSc signature
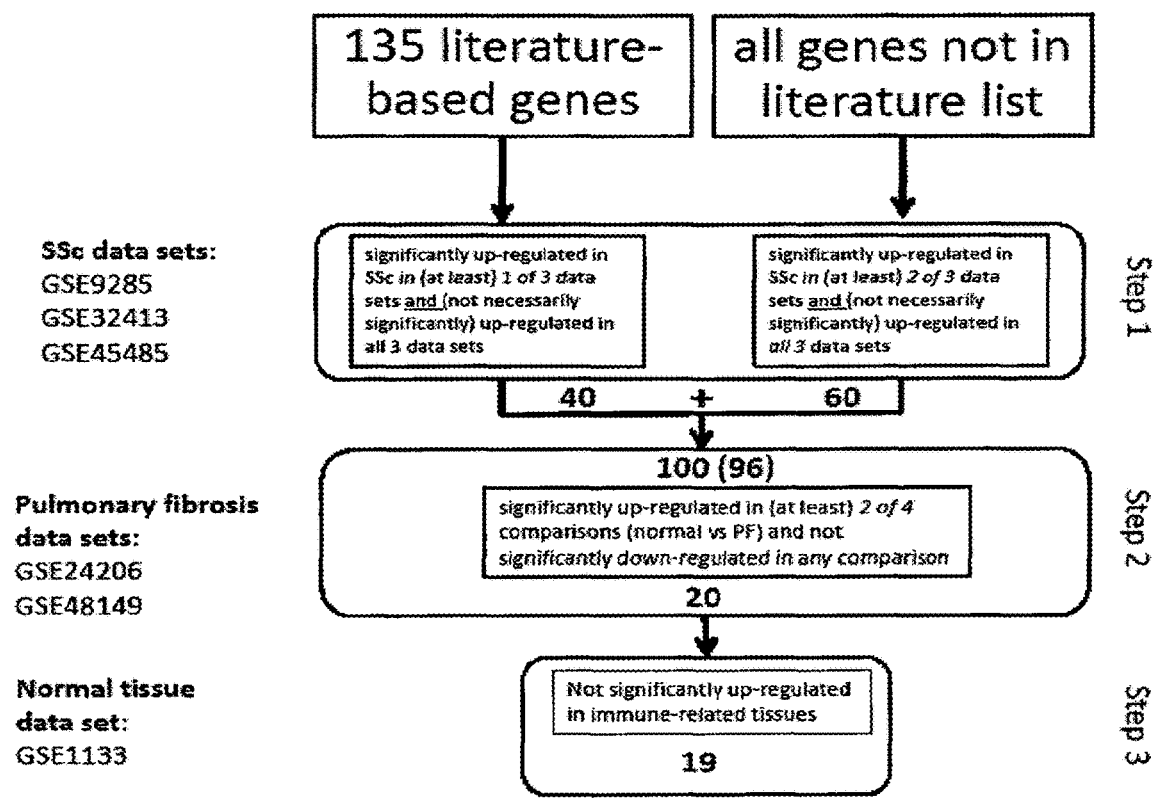

Figure 9: RGS5 expression by SSc and normal skin in GSE45485 with respective results of the moderated t-test comparing expression of RGS5 in SSc and normal skin
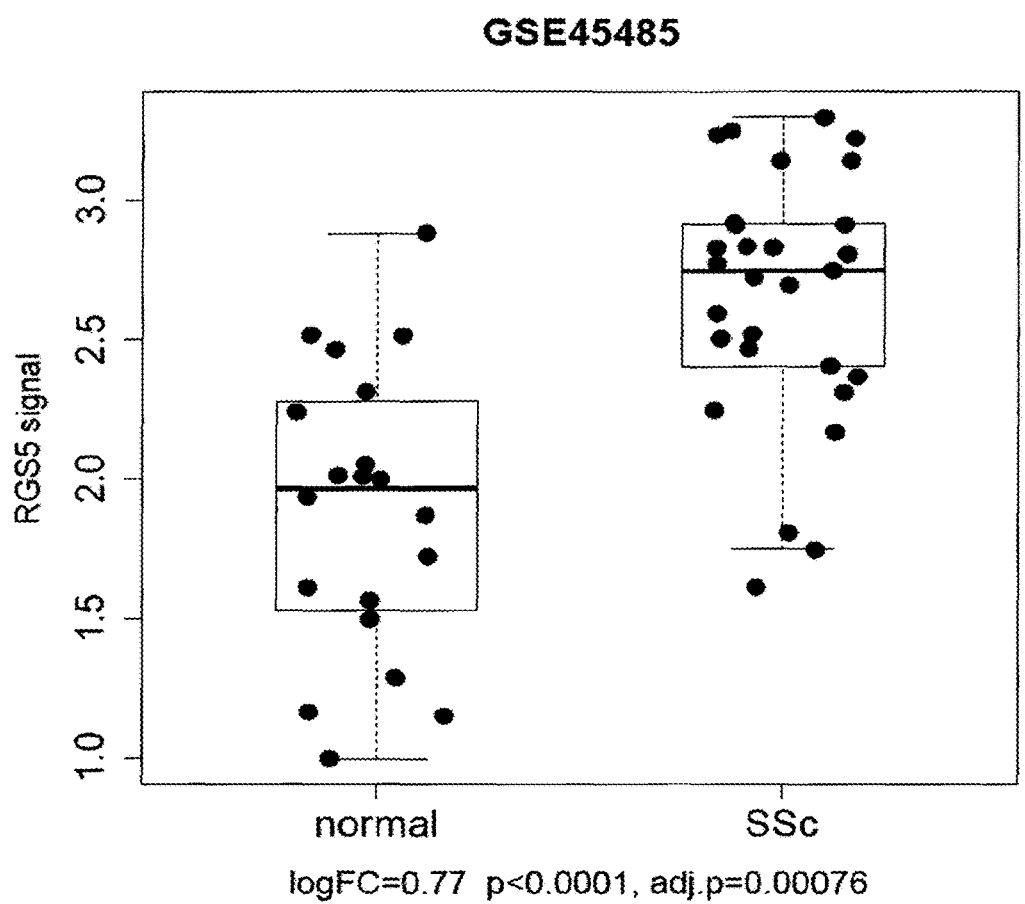
logFC = log fold change (from normal skin to SSc)

Figure 10: COL15A1 expression by early IPF, advanced IPF and normal lung in GSE24206 with respective results of the moderated t-test comparing expression of COL15A1 in early IPF and healthy lung and advanced IPF and healthy lung, respectively
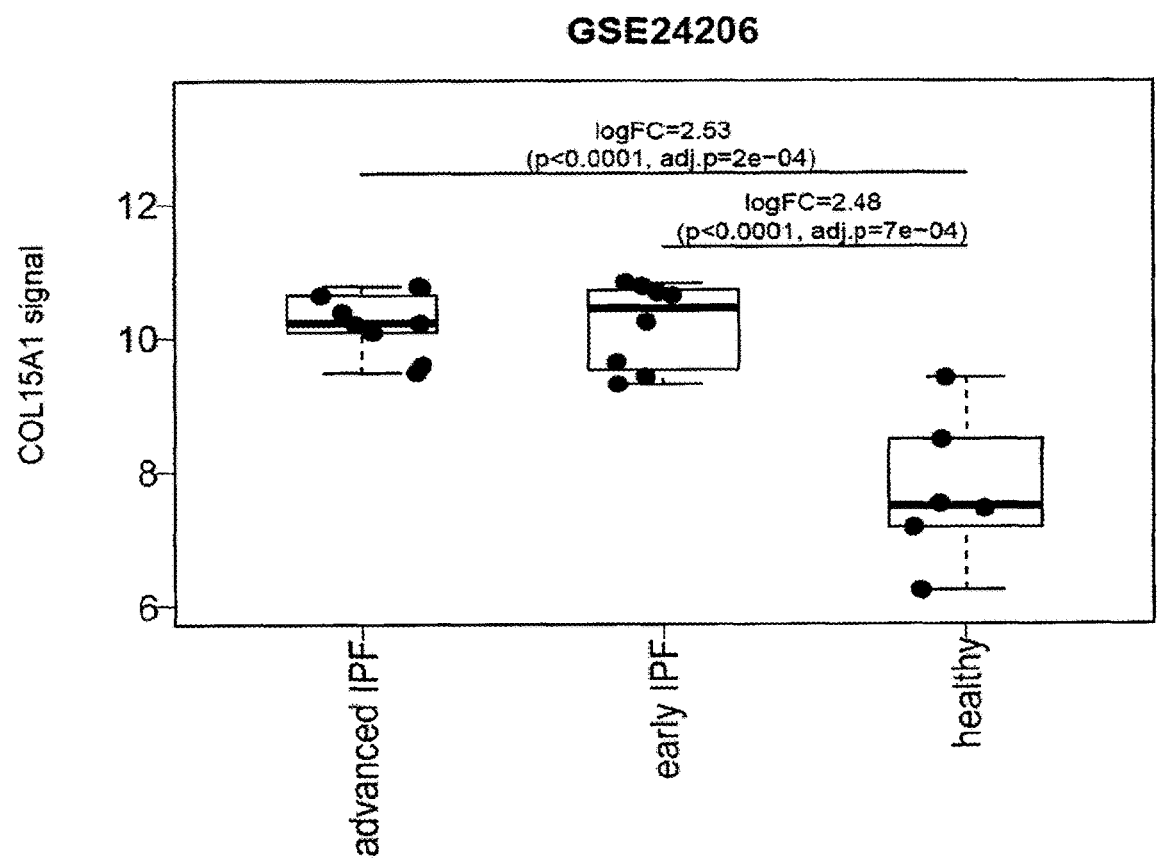
logFC = log fold change (from normal lung to early/advanced IPF)

Figure 11: COL1A1 expression by early IPF, advanced IPF and normal lung in GSE24206 with respective results of the moderated t-test comparing expression of COL1A1 in early IPF and healthy lung and advanced IPF and healthy lung, respectively
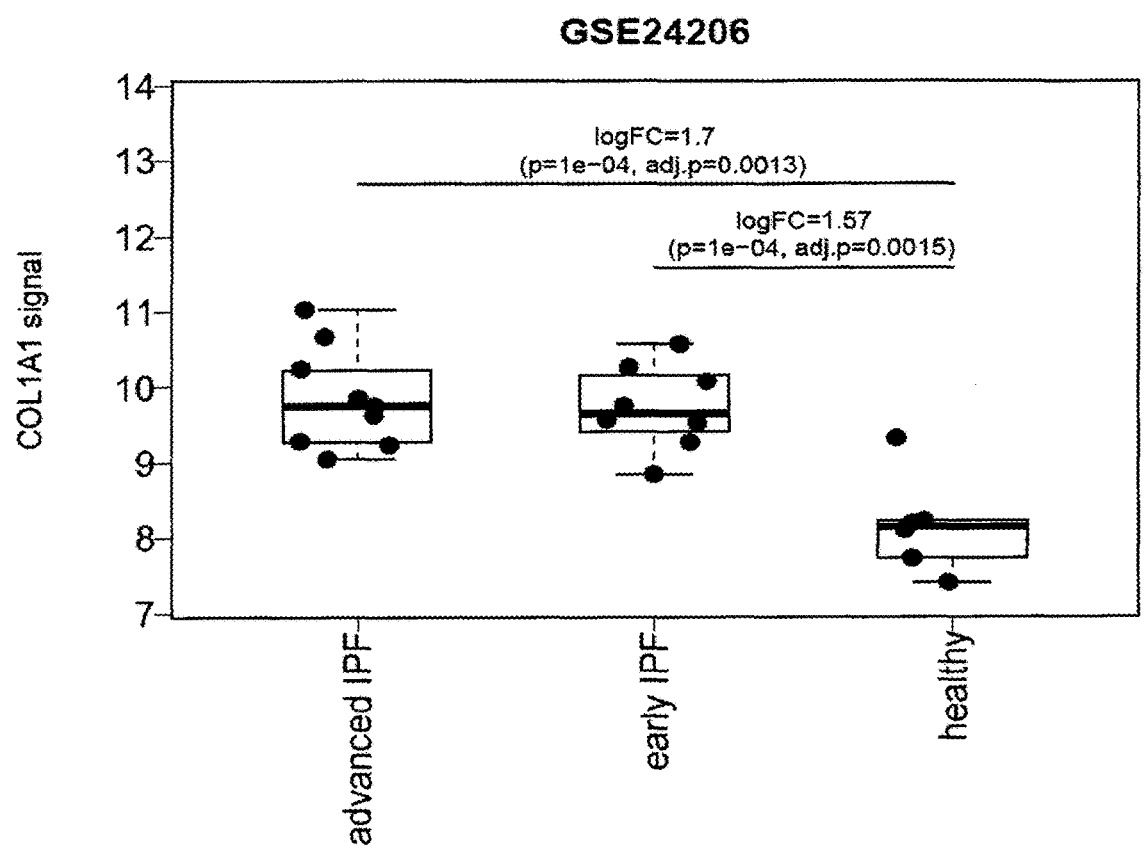
logFC = log fold change (from normal lung to early/advanced IPF)

Figure 12: COMP expression by IPAH (PPH), IPF, SSc-PAH, SSc-PF and normal lung (NL) in GSE48149 with respective results of the moderated t-test comparing expression of COMP in early IPF and normal lung and SSc-PF and normal lung, respectively
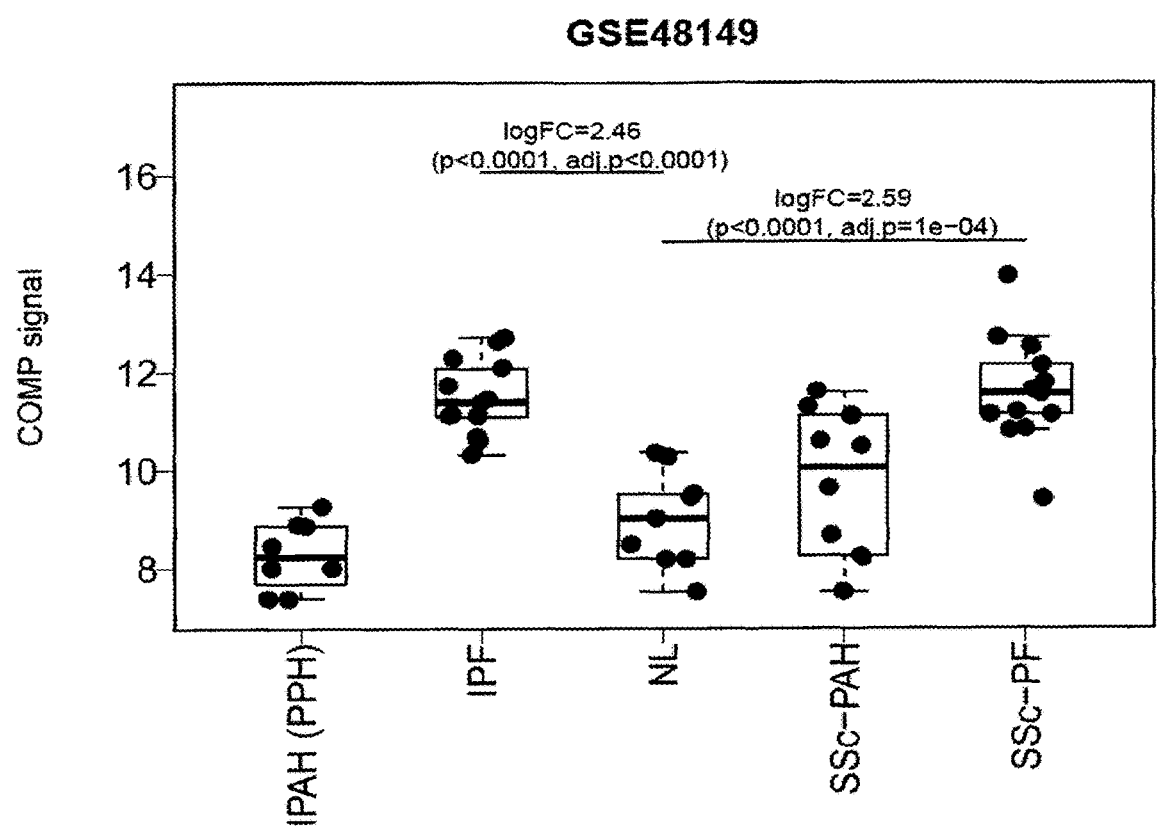
logFC = log fold change (from normal lung to IPF/SSc-PF)

Figure 13: IGFBP2 expression by IPAH (PPH), IPF, SSc-PAH, SSc-PF and normal lung (NL) in GSE48149 with respective results of the moderated t-test comparing expression of IGFBP2 in early IPF and normal lung and SSc-PF and normal lung, respectively
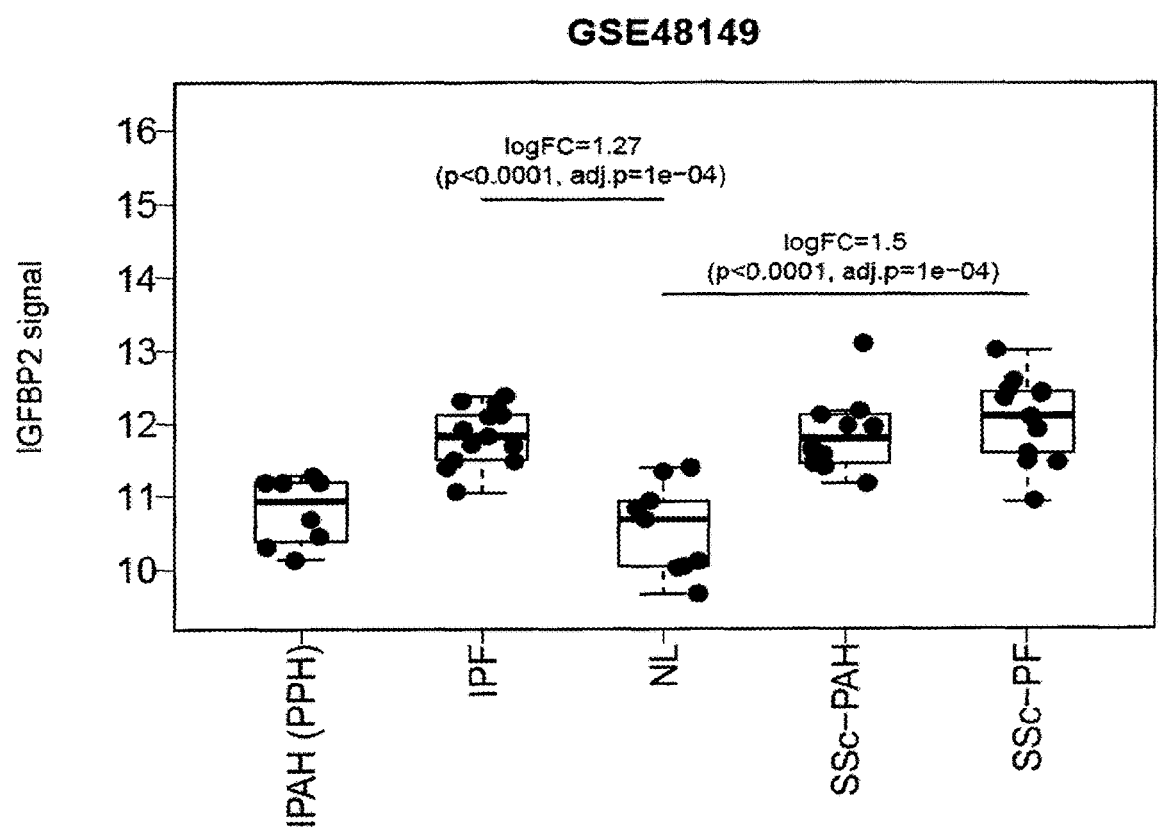
logFC = log fold change (from normal lung to IPF/SSc-PF)

Figure 14a: SSP1 expression by IPAH (PPH), IPF, SSc-PAH, SSc-PF and normal lung (NL) in GSE48149 with respective results of the moderated t-test comparing expression of SSP1 in early IPF and normal lung and SSc-PF and normal lung, respectively
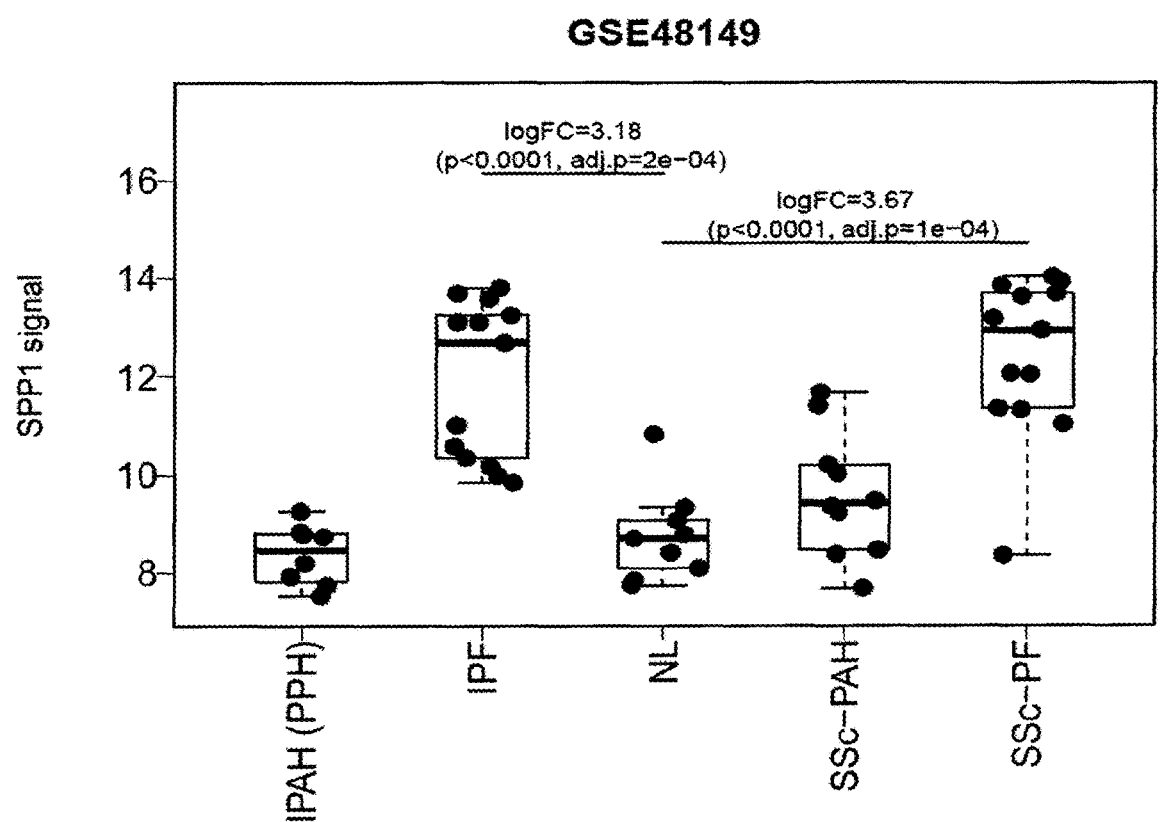
logFC = log fold change (from normal lung to IPF/SSc-PF)

Figure 14b: Signature Score of 19-gene fibrosis/SSc signature by SSc and normal skin in GSE45485 with results of the one-sided t-test comparing 19-gene Signature Score in SSc and normal skin
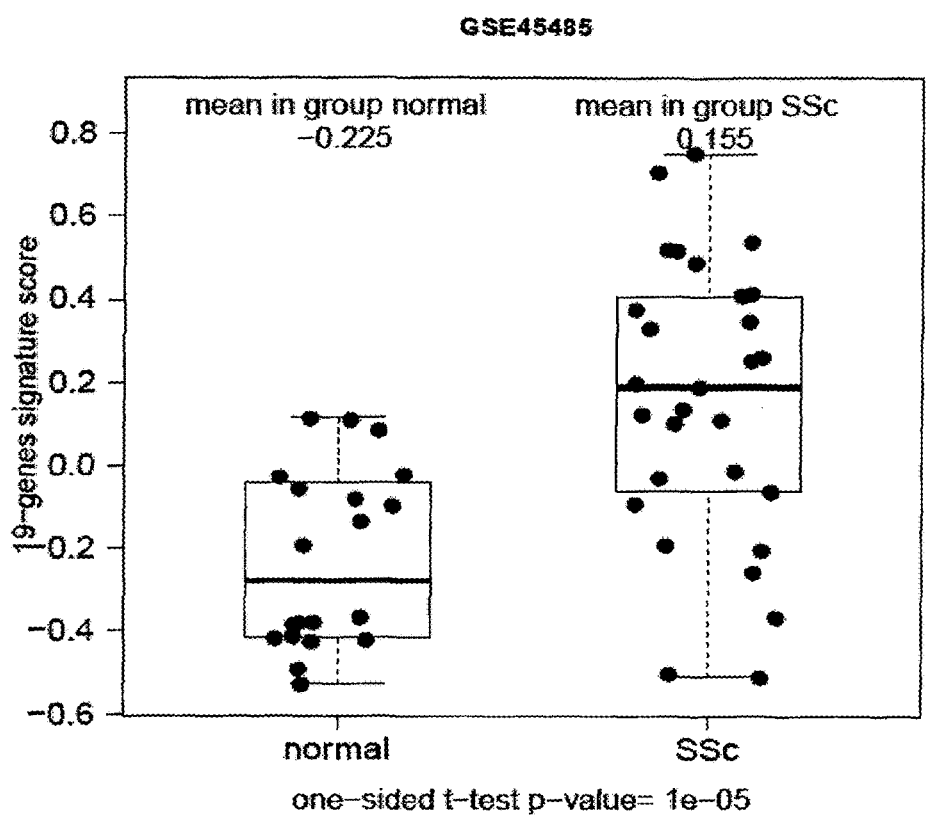

Figure 15a: Signature Score of 19-gene fibrosis/SSc signature by SSc and normal skin in GSE32413 with results of the one-sided t-test comparing 19-gene Signature Score in SSc and normal skin
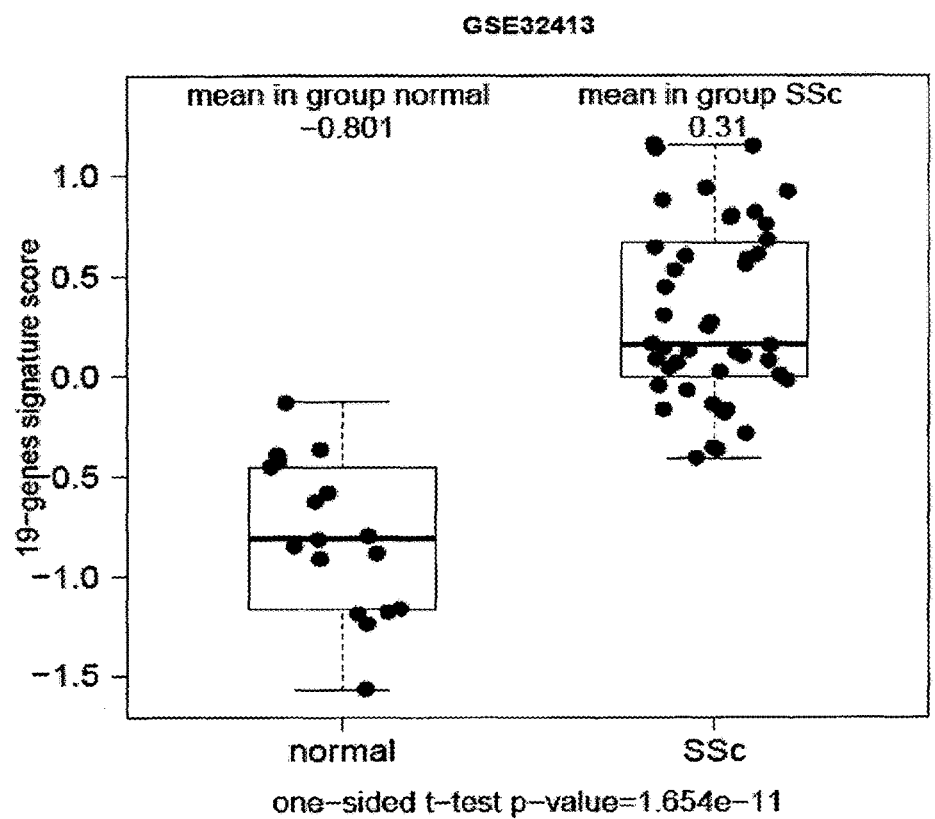

Figure 15b: Signature Score of 9-gene TUAD signature by SSc and normal skin in GSE32413 with results of the one-sided t-test comparing 9-gene Signature Score in SSc and normal skin
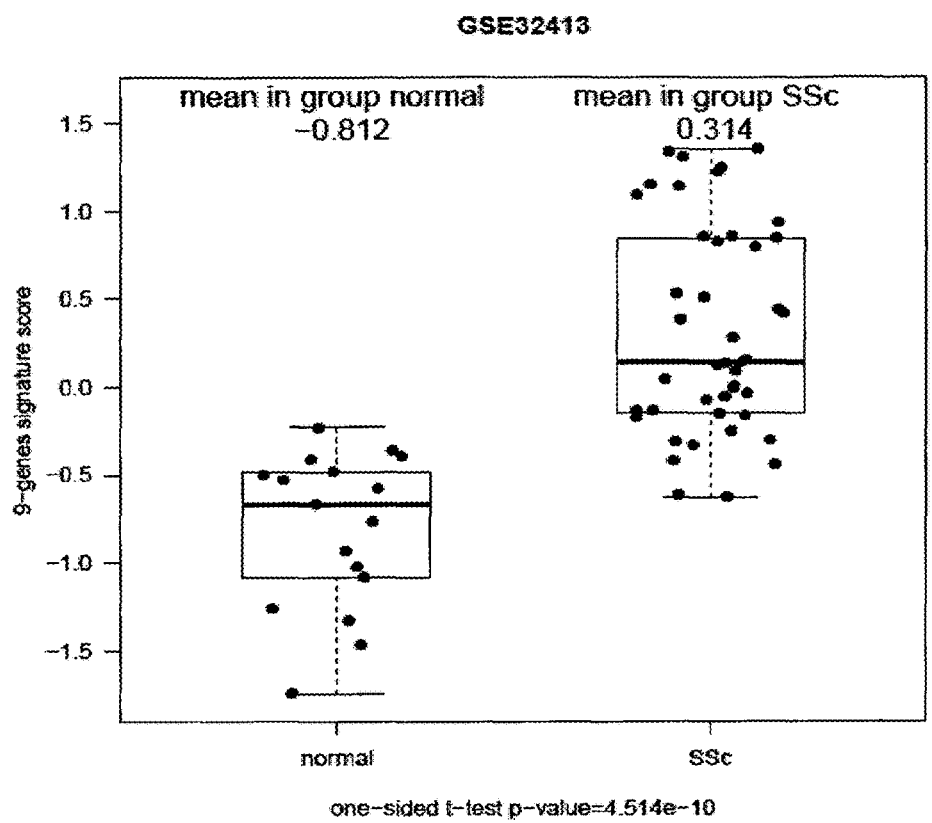

Figure 16a: Signature Score of 19-gene fibrosis/SSc signature by SSc and normal skin in GSE9285 with results of the one-sided t-test comparing 19-gene Signature Score in SSc and normal skin
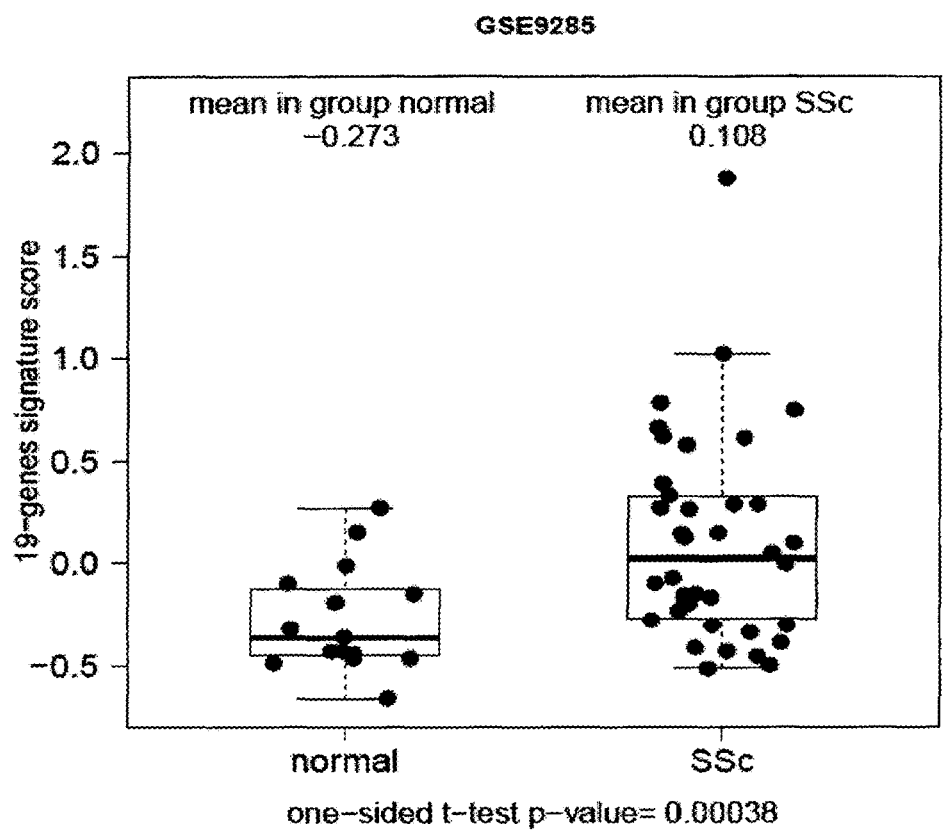

Figure 16b: Signature Score of 9-gene TUAD signature by SSc and normal skin in GSE9285 with results of the one-sided t-test comparing 9-gene Signature Score in SSc and normal skin
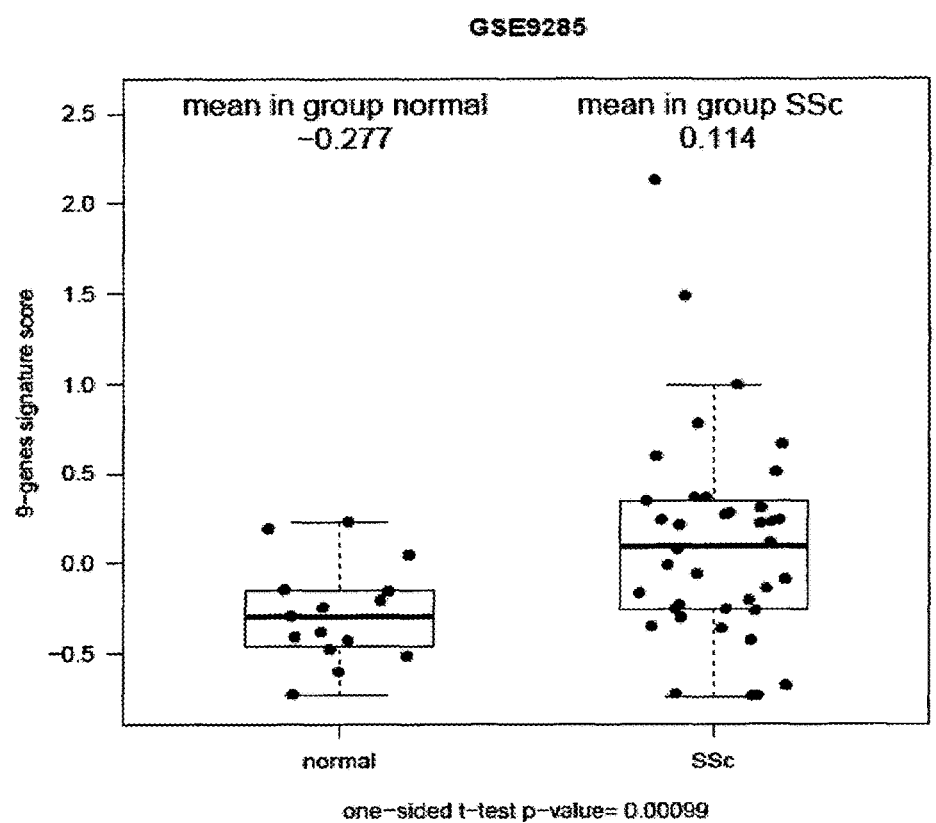

Figure 17a: Signature Score of 19-gene fibrosis/SSc signature by early IPF, advanced IPF and healthy lung in GSE24206 with results of the one-sided t-test comparing 19-gene Signature Score in early IPF and normal lung and advanced IPF and normal lung, respectively
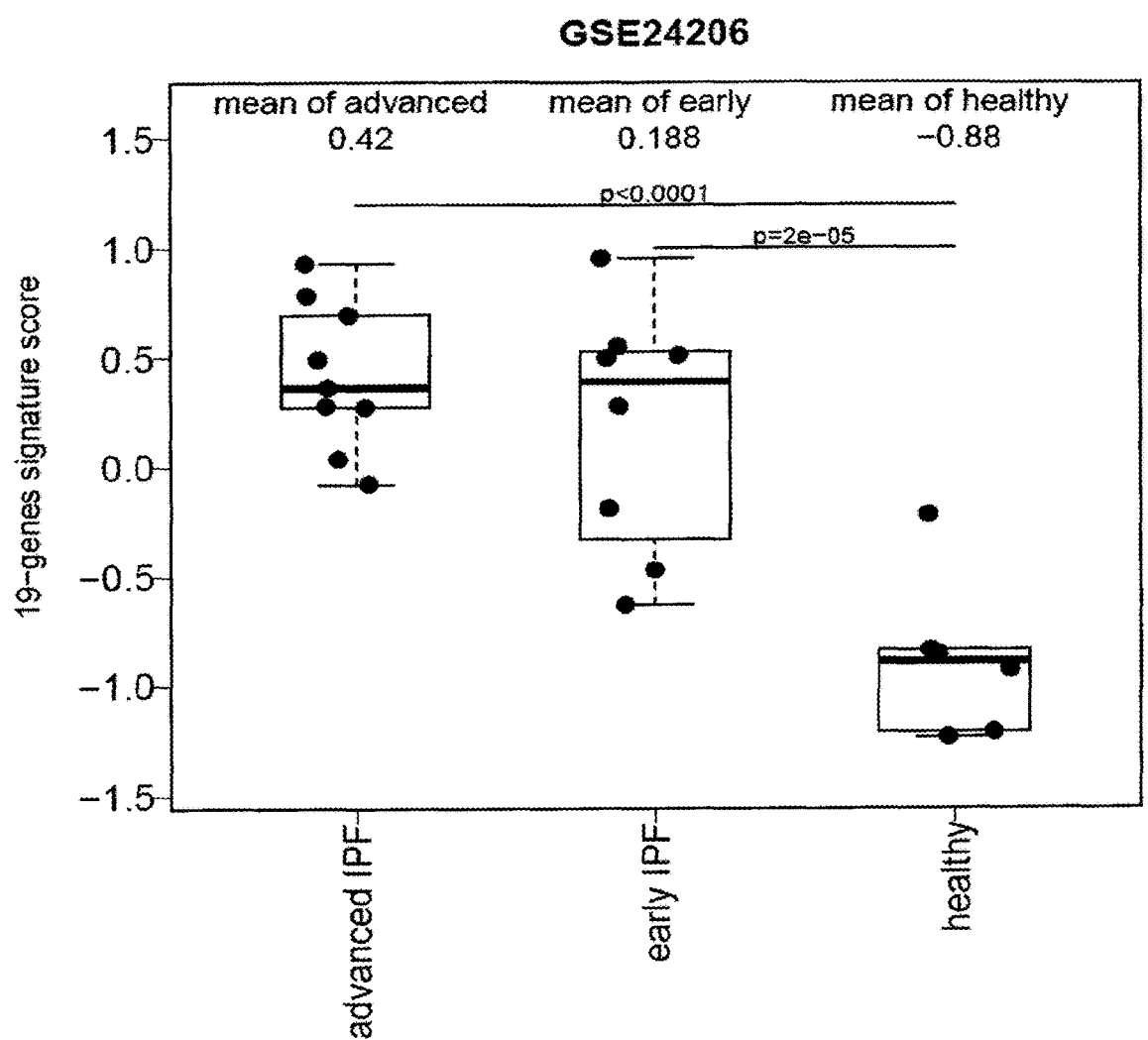

Figure 17b: Signature Score of 9-gene TUAD signature by early IPF, advanced IPF and healthy lung in GSE24206 with results of the one-sided t-test comparing 9-gene Signature Score in early IPF and normal lung and advanced IPF and normal lung, respectively
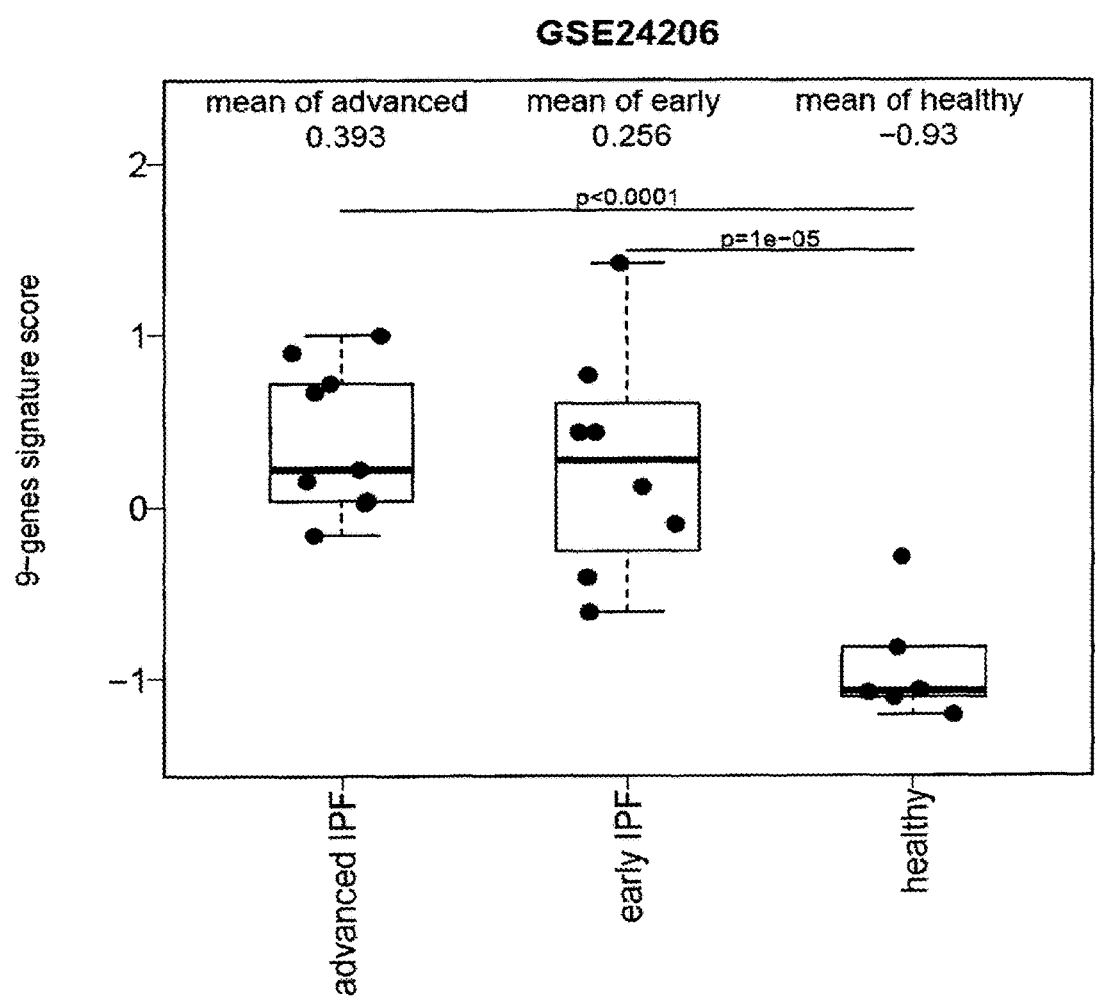

Figure 18a: Signature Score of 19-gene fibrosis/SSc signature by IPAH (PPH), IPF, SSc-PAH, SSc-PF and normal lung (NL) in GSE48149 with results of the one-sided t-test comparing 19-gene Signature Score in IPF and normal lung and SSc-PF and normal lung, respectively
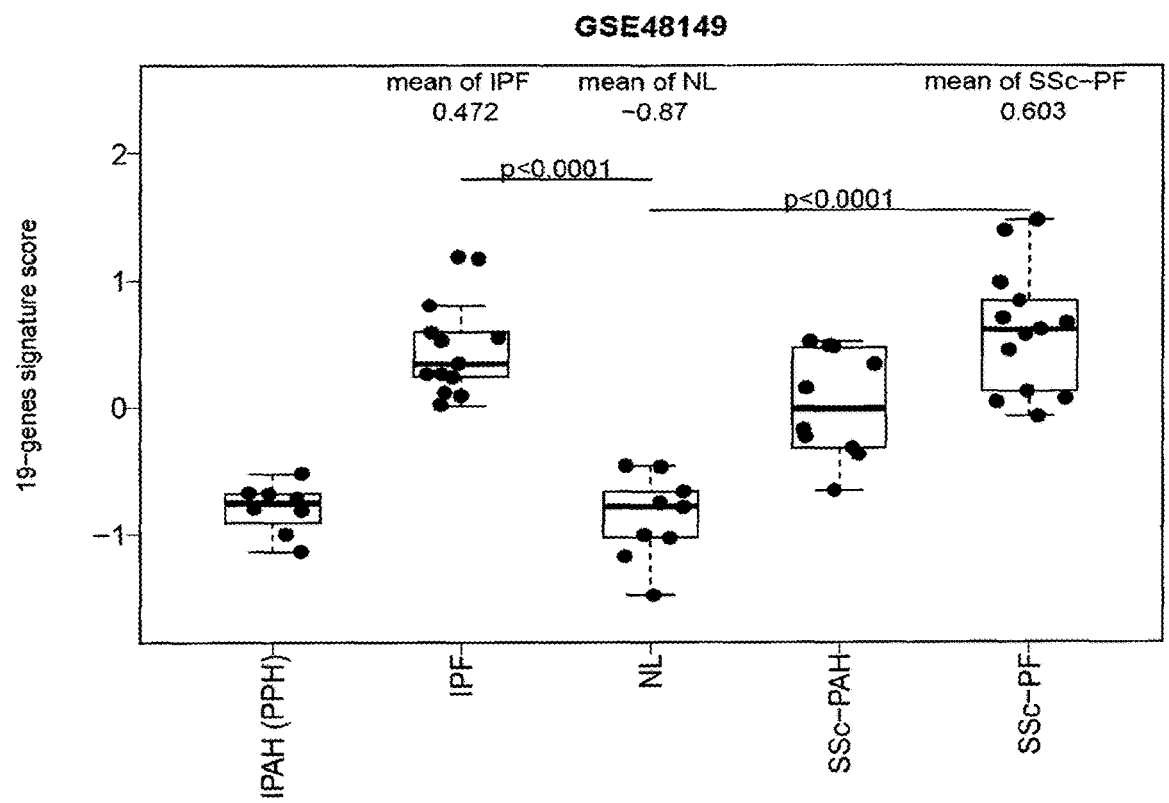

Figure 18b: Signature Score of 9-gene TUAD signature by IPAH (PPH), IPF, SSc-PAH, SSc-PF and normal lung in GSE48149 with results of the one-sided t-test comparing 9-gene Signature Score in IPF and normal lung and SSc-PF and normal lung, respectively
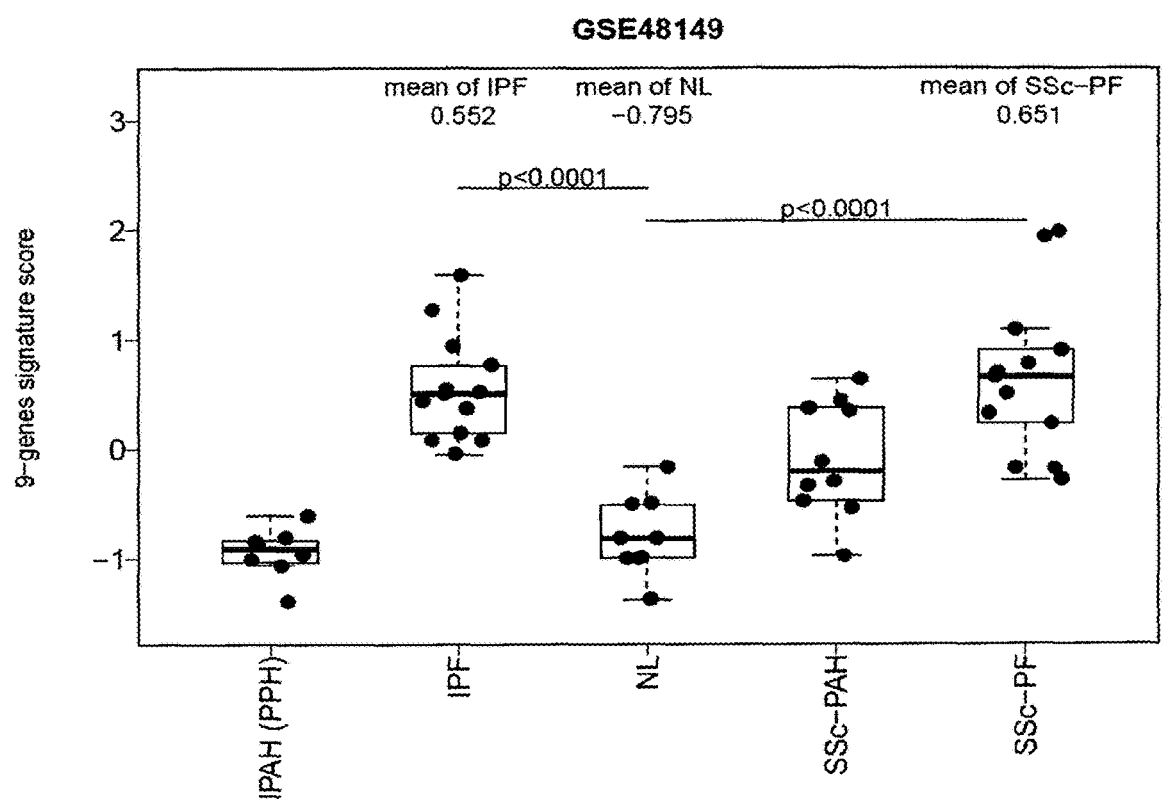

Figure 19a: Signature Score of 19-gene SSc/fibrosis signature by Nash, steatosis, healthy obese and normal liver in GSE48452 with results of the one-sided t-test comparing 19-gene Signature Score in NASH, steatosis and heathy obese against control liver tissue, respectively
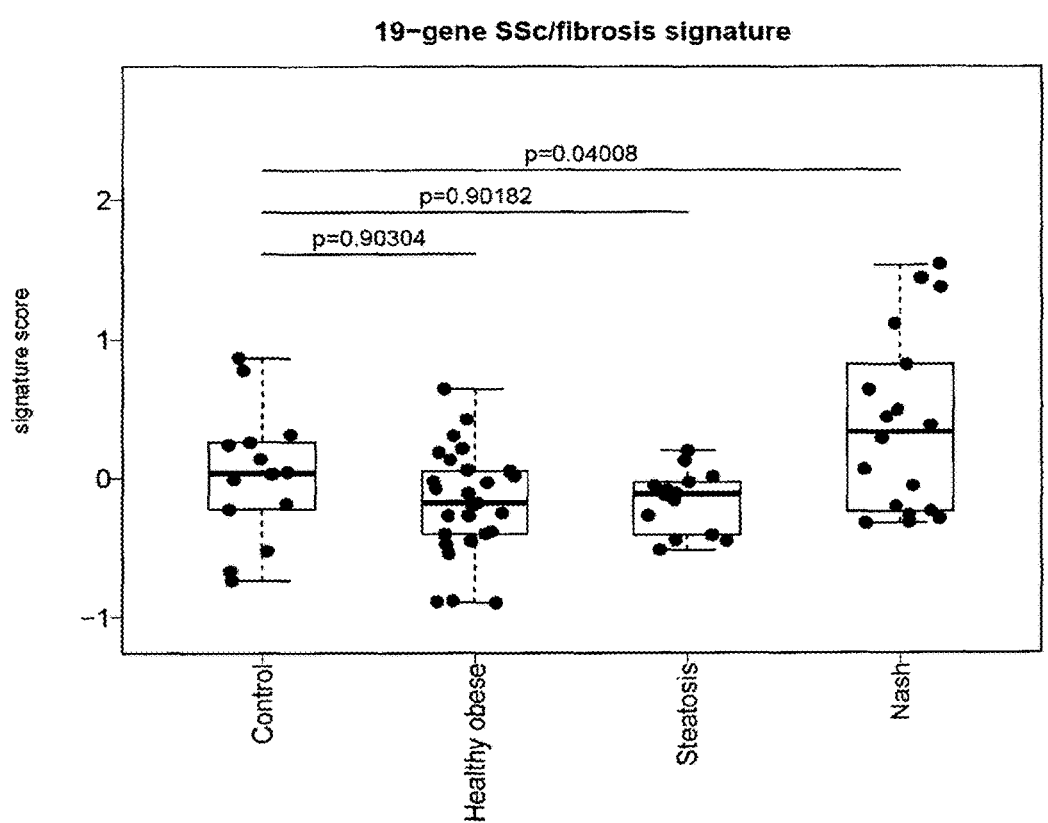

Figure 19b: Signature Score of 9-gene TUAD signature by Nash, steatosis, heathy obese and normal liver in GSE48452 with results of the one-sided t-test comparing 9-gene Signature Score in NASH, steatosis and heathy obese against control liver tissue, respectively
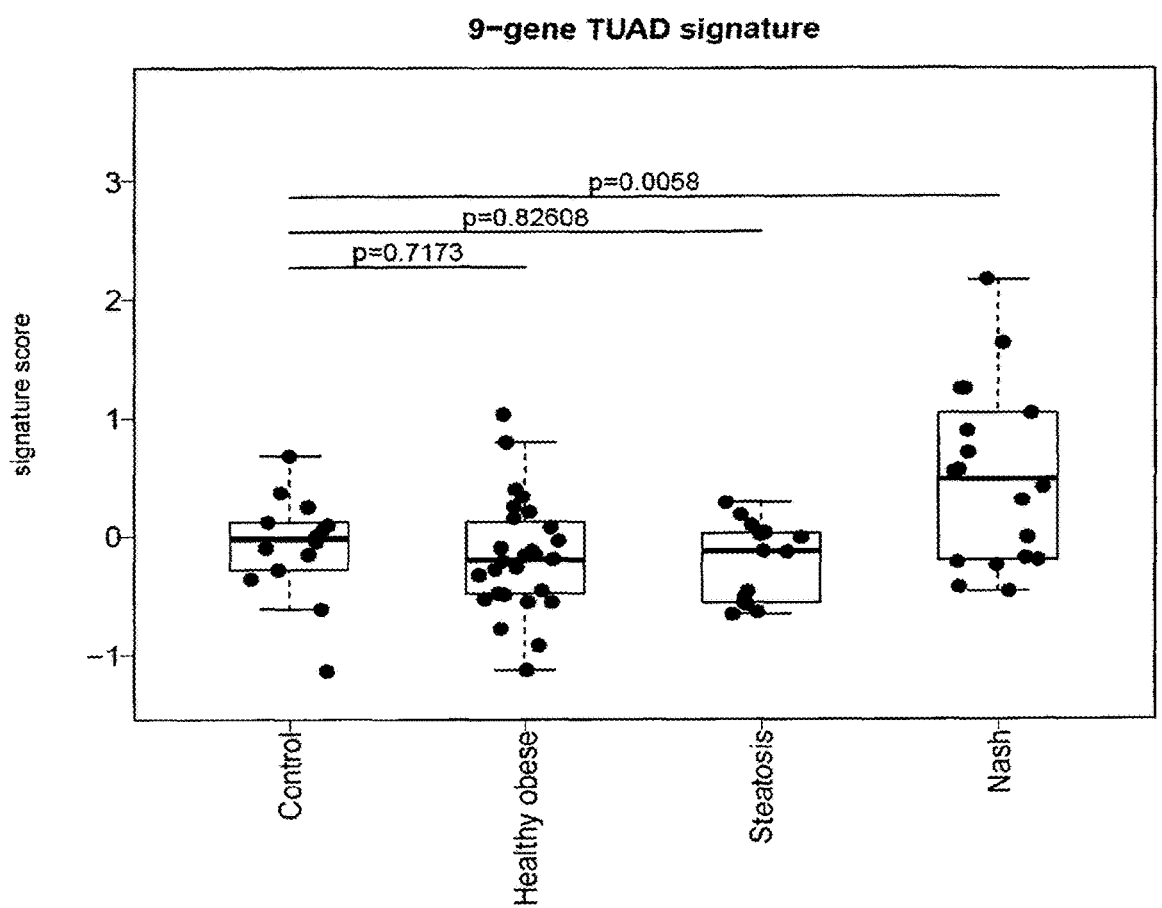

Figure 20a: Signature Score of 19-gene SSc/fibrosis signature mild and advanced stage liver fibrosis in GSE49541 with results of the one-sided t-test
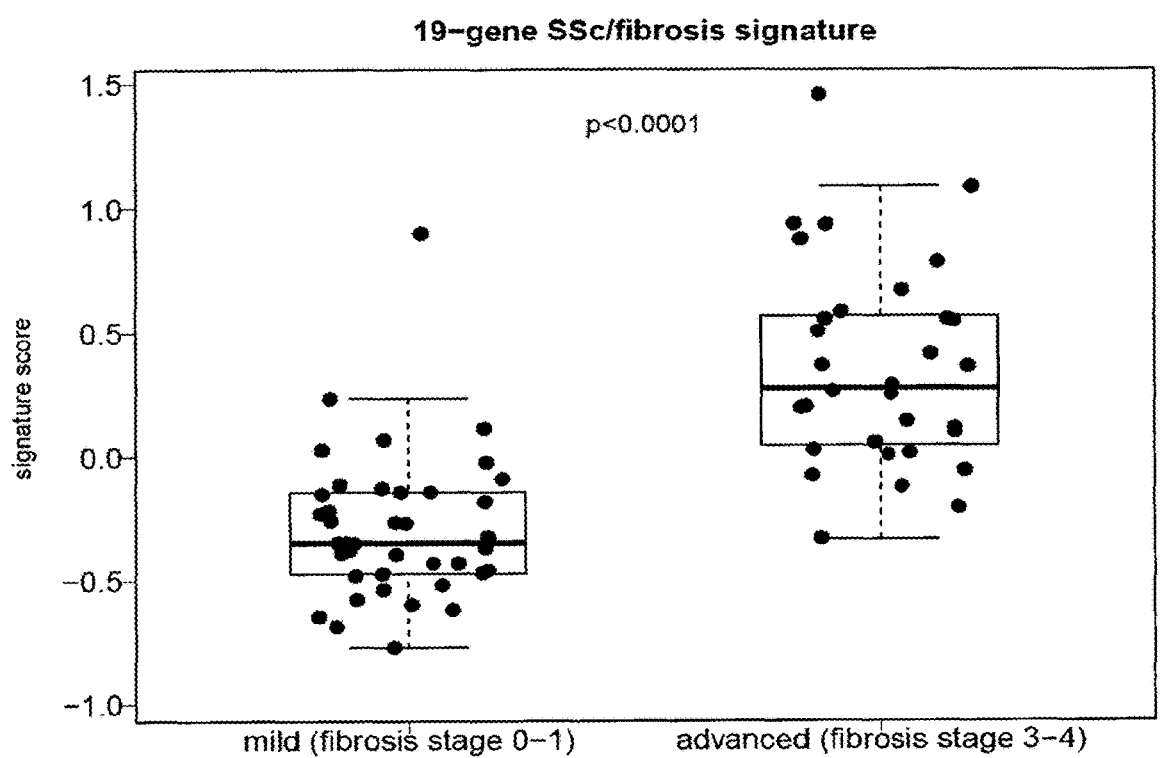

Figure 20b: Signature Score of 9-gene TUAD signature mild and advanced stage liver fibrosis in GSE49541 with results of the one-sided t-test
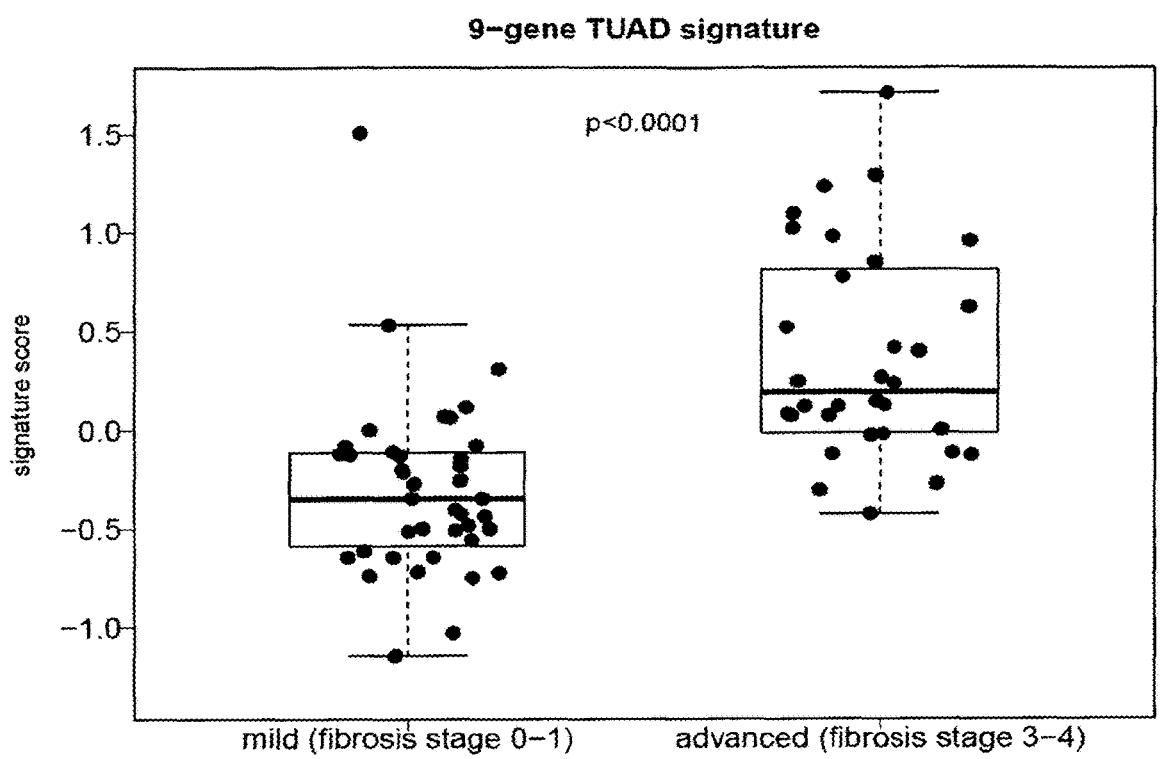

Figure 21a: Signature Score of 19-gene SSc/fibrosis signature by Nash, PSC, PBC, NAFLD, healthy obese and normal liver in GSE61260 with results of the one-sided t-test comparing 19-gene Signature Score in Nash, PSC, PBC and NAFLD against control liver tissue, respectively
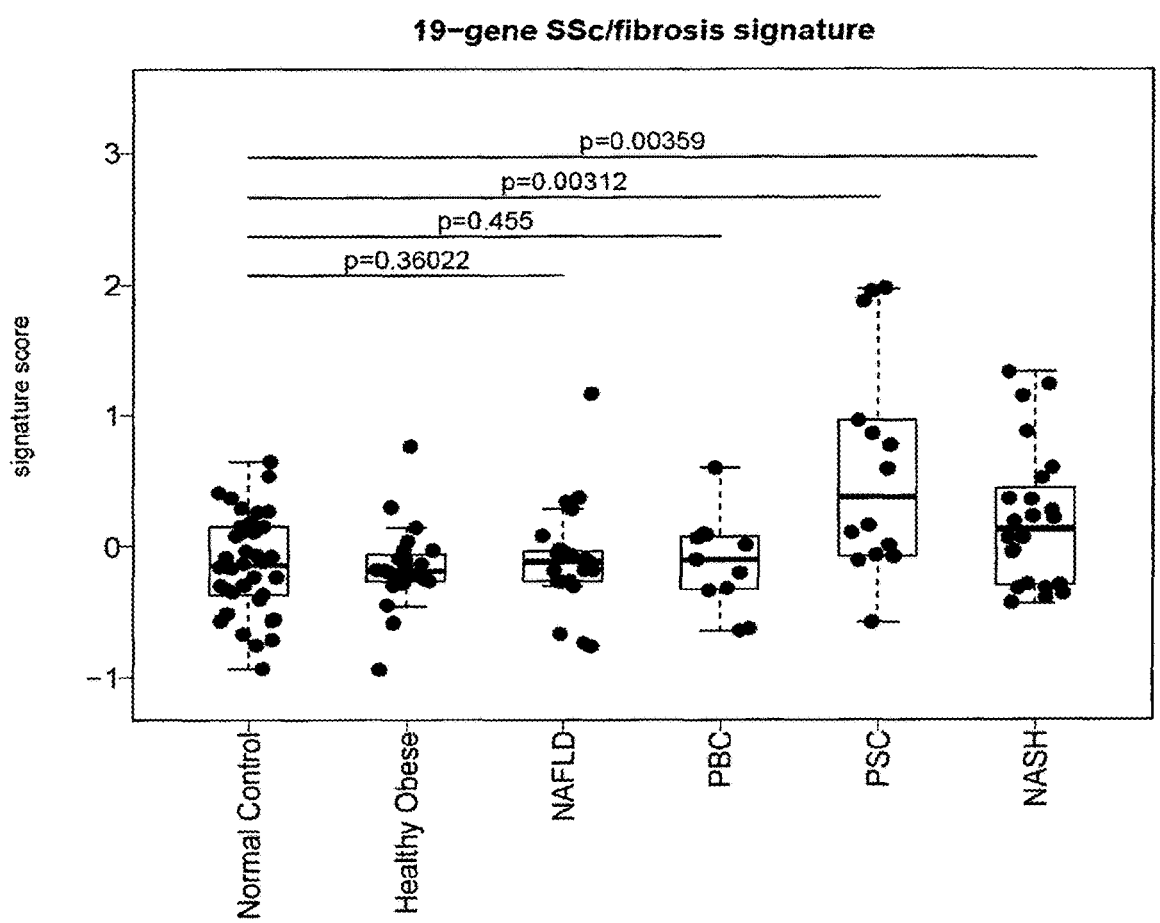

Figure 21b: Signature Score of 9-gene TUAD signature by Nash , PSC , PBC, NAFLD), healthy obese and normal liver in GSE61260 with results of the one-sided t-test comparing 9-gene Signature Score in Nash, PSC, PBC and NAFLD against control liver tissue, respectively
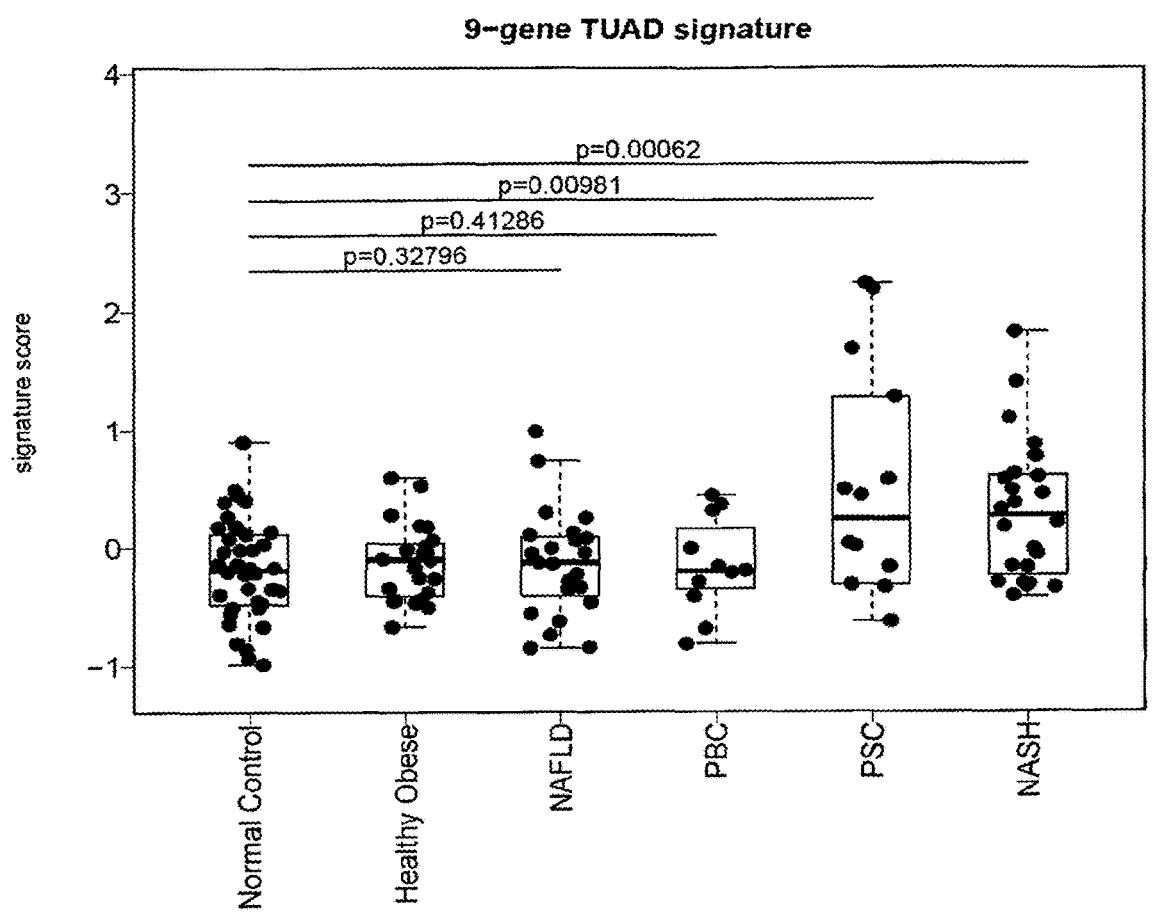

Figure 22a: Signature Score of 19-gene SSc/fibrosis signature by primary myelofibrosis and normal bone marrow in GSE44426 w/results of the one-sided t-test
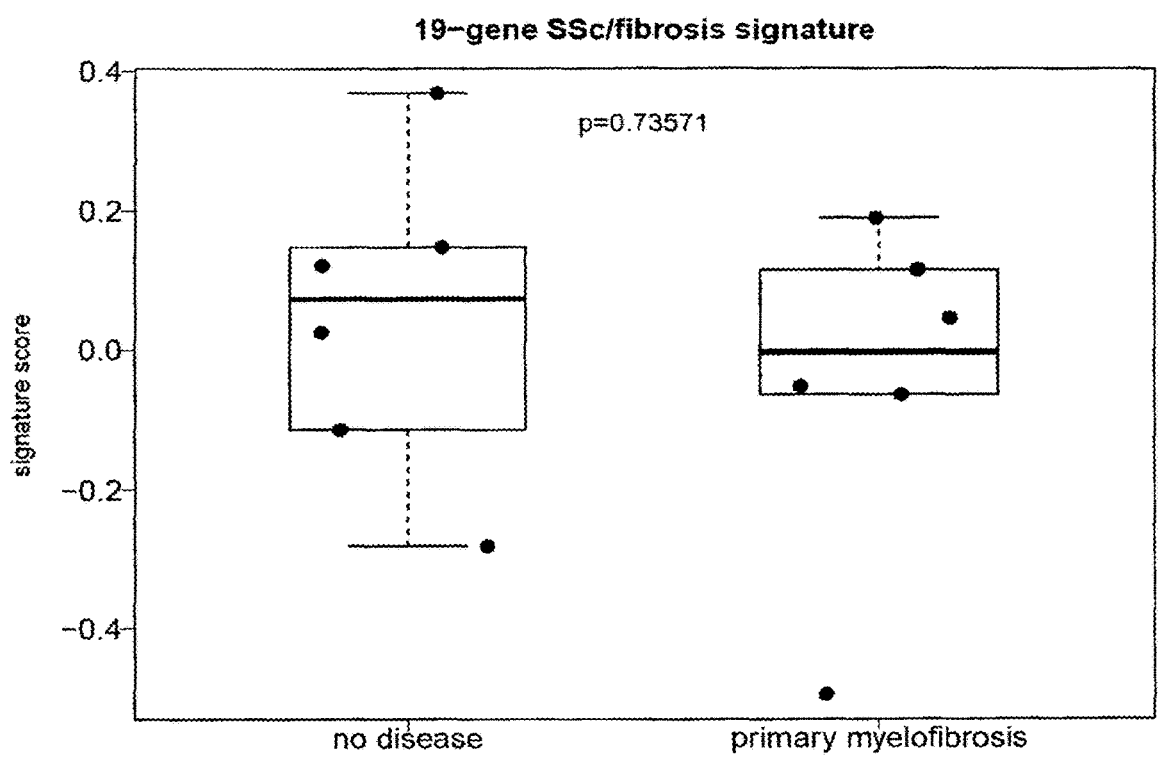

Figure 22b: Signature Score of 9-gene TUAD signature by primary myelofibrosis and normal bone marrow in GSE44426 w/results of the one-sided t-test
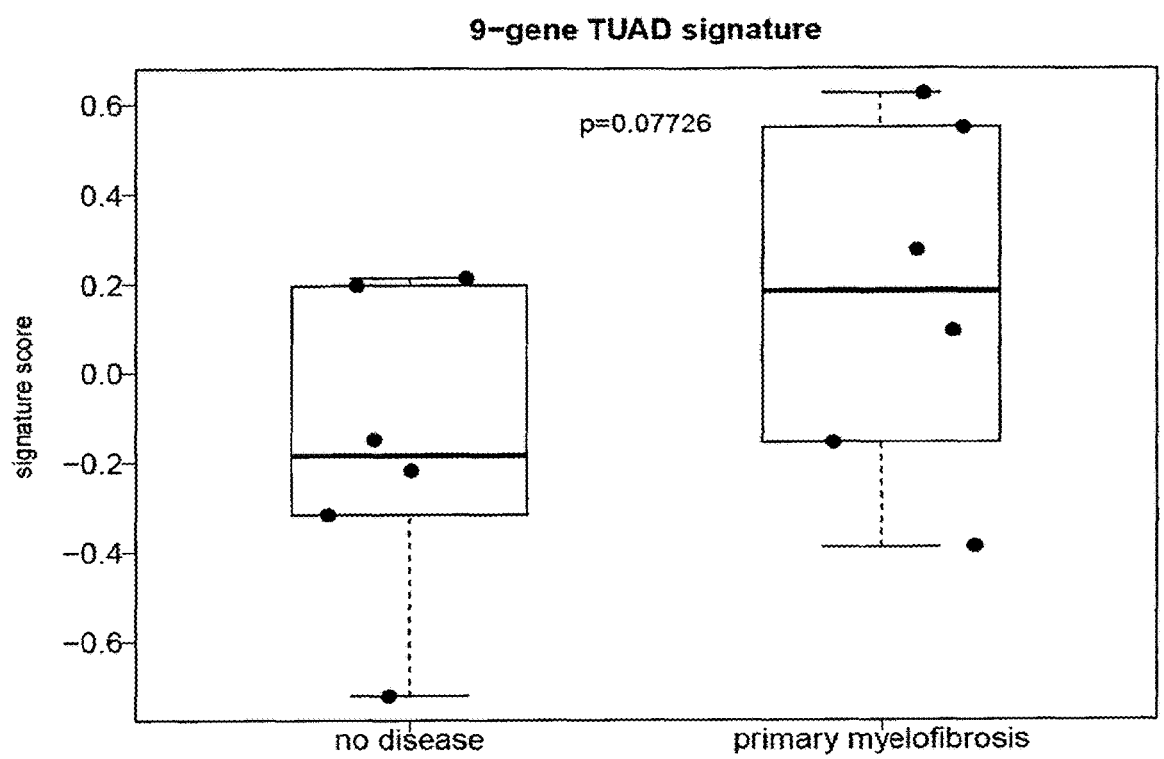

ced ANTI-ALPHA-V INTEGRIN ANTIBODY FOR THE TREATMENT OF FIBROSIS AND/OR FIBROTIC DISORDERS This application is a continuation of U.S. application Ser. No. 15/778,615, filed on May 23, 2018, which was the National Stage entry under § 371 of International Application No. PCT/EP2016/001970, filed on Nov. 22, 2016, and which claims the benefit of U.S. Provisional Application No. 62/258,626, filed on Nov. 23, 2015, and which claims priority to European Application No. 16164879.5, filed on Apr. 12, 2016, all of which are incorporated in their entireties by reference.

The instant application contains a Sequence Listing which has been submitted electronically in ASCII format and is hereby incorporated by reference in its entirety. Said ASCII copy, created on Jun. 8, 2018, is named 2018-06-07-Seg-List.txt and is 8,853 bytes in size.

FIELD OF THE INVENTION

The invention is directed to the treatment of fibrosis and/or fibrotic diseases by means of antibodies. The invention is furthermore directed to the prophylaxis of fibrosis and/or fibrotic diseases by antibodies. Above all, the invention relates to the administration of an anti-alpha-v integrin (receptor) antibody to patients suffering from fibrosis and/or fibrotic diseases, including but not limited to systemic sclerosis (SSc). More specifically, the instant invention relates to the treatment of fibrotic diseases of the skin, lung, heart, liver and/or kidney by means of said antibody, and/or the prophylaxis thereof. Even more specifically, the instant invention relates to the administration of a recombinant, de-immunized monoclonal antibody targeting αv-integrins patients suffering from systemic sclerosis, including, but not limited to systemic sclerosis of the skin, lung, heart and/or kidney. In particular, the invention is relates to the therapy of said patients by means of the anti-alpha-v integrin antibody DI17E6 (Abituzumab) and structural mutants or modifications thereof. One important target of said therapy is to slow, halt and/or revert said fibrosis and/or fibrotic diseases in patients, thus preferably to generally improve the status of a patient suffering from fibrosis and/or fibrotic disease. One further important target of said therapy is to slow, halt and/or revert systemic sclerosis in patients, thus preferably to generally improve the status and quality of life of the patient suffering from said systemic sclerosis. Another preferred aspect of the invention relates to the prophylaxis against fibrosis and/or fibrotic disorders in subjects, preferably human subjects, which are likely to develop fibrosis and/or fibrotic disorders, by administering the anti-alpha-v integrin antibody DI17E6 (Abituzumab) and/or structural mutants or modifications thereof.

BACKGROUND OF THE INVENTION

Fibrosis is preferably defined as the formation of excess fibrous tissue, preferably fibrous connective tissue, in an organ or tissue, preferably in a reparative or reactive process. This can preferably qualified as a reactive, benign, or pathological state. In response to injury, this is preferably called scarring, and if fibrosis arises from a single cell line, this is preferably called a fibroma. Physiologically, fibrosis typically acts to deposit connective tissue, which can obliterate the architecture and function of the underlying organ or tissue. Fibrosis can preferably be used to describe the pathological state of excess deposition of fibrous tissue, as well as the process of connective tissue deposition in healing. In the context of the present invention, the term fibrosis is preferably used to describe the pathological state of excess deposition of fibrous tissue. Fibrosis in the pathological sense is similar to the process of scarring, in that both involve stimulated cells laying down connective tissue, including collagen and glycosaminoglycans. Immune cells called macrophages, as well as any damaged tissue between surfaces called interstitium, typically release TGF-β. There are numerous reasons for this, including inflammation of the nearby tissue, or a generalized inflammatory state, with increased circulating mediators. TGF-β stimulates the proliferation and activation of fibroblasts, which then normally trigger the deposition of connective tissue.

Fibrosis can occur in many tissues of many organs within the body, typically as a result of inflammation or damage, and examples include:

Fibrosis of the lung, e.g. pulmonary fibrosis, cystic fibrosis and/or idiopathic pulmonary fibrosis; Fibrosis of the liver, e.g. liver cirrhosis;

Fibrosis of the heart, e.g. atrial fibrosis, endomyocardial fibrosis and/or as the consequential damage of a previous myocardial infarction.

Moreover, fibrosis, and especially pathological fibrosis, preferably includes arthrofibrosis (predominantly of the knee and shoulder, but also occurring in a variety of other joints), Crohn's Disease (intestines), Dupuytren's contracture (predominantly in the hands and/or fingers), Keloid (predominantly affecting the skin), Mediastinal fibrosis (predominantly relating to the soft tissue of the mediastinum), Myelofibrosis (predominantly affecting the bone marrow), Peyronie's disease (penis), Nephrogenic systemic fibrosis (predominantly affecting the skin), progressive massive fibrosis (e.g. of the lungs, often a consequential complication of coal workers' pneumoconiosis), retroperitoneal fibrosis (predominantly affecting the soft tissue of the retroperitoneum), and/or scleroderma or systemic sclerosis (predominantly affecting the skin and/or lungs).

The terms fibrosis, pathological fibrosis and fibrotic diseases or fibrotic disorders are known and understood in the art.

Preferably, all pathological forms of fibrosis, i.e. forms that are not directly related to acute damage and/or normal wound healing, are also referred to in the context of the present invention as fibrotic disorders. Thus, fibrotic disorders are preferably those states of fibrosis which exceed the level of fibrosis that is normally found in desired, correct wound healing processes.

Systemic sclerosis (SSc, ICD-10 classification M34) is an especially preferred fibrotic disorder to be treated according to the instant invention. Systemic sclerosis is often also referred to as systemic scleroderma and sometimes as progressive systemic sclerosis. Systemic sclerosis is a clinically heterogeneous multi-organ connective tissue disease with a characteristic but variable spectrum of clinical and laboratory presentations with features of autoimmunity, vascular injury and progressive fibrosis, leading to pain, disability, progressive dysfunction and ultimately failure of vital organs such as lung, heart, or kidney. Preferably, SSc can be differentiated from a group of diseases termed localized scleroderma, that preferably include conditions such as morphea, linear scleroderma and scleroderma en-coup-desabre, and preferably also other disorders that mimic one or more signs of scleroderma.

The aetiology of SSc is currently unknown. However, the spectrum of clinical presentations is a consequence of variable degrees of vascular abnormalities, immune mediated damage and fibrosis potentially possible in almost any organ. Organ involvement in SSc can lead to decline of its function and precocious mortality when vital organs such as lung, liver, kidney and heart are affected. The skin is almost always involved. Based on the pattern of skin involvement SSc is classified into diffuse cutaneous (dc) SSc and localized cutaneous (lc) SSc. In lcSSc skin involvement typically extends from the distal extremities to the knees and elbows; in dcSSc the skin involvement typically extends proximally, involving the trunk upper arms and/or thighs. More details on preferred subsets and disease classifications can be found in the sections "Classification" and "Diagnosis and Symptoms". SSc can have overlapping features with other connective tissue diseases (CTD) such as systemic lupus erythematosus, polymyositis, rheumatoid arthritis or Sjögren's syndrome.

SSc is typically associated with one or more of the following histopathological and pathophysiological characteristics:

i) Vascular Abnormalities:

The characteristic pathologic finding in SSc vascular abnormalities is a non-inflammatory proliferative/obliterative vasculopathy involving small arteries and arterioles in multiple vascular beds. Although in long-standing SSc these lesions generally occur in the absence of inflammation, in early stage disease, inflammatory cell infiltrates are prominent in many organs. Histopathologic evidence of vascular damage is present before fibrosis can be detected in involved and non-involved skin, indicating a generalized process. Manifestations, such as Raynaud's phenomenon, generally precede other disease manifestations. Additional clinical signs of SSc vasculopathy include cutaneous telangiectasia, nail-fold capillary alterations, pulmonary arterial hypertension (PAH), digital pit formation, gastric antral vascular ectasia, and scleroderma renal crisis.

In patients with established SSc, the most characteristic vascular finding is bland intimal proliferation in the small and medium sized arteries. In late stages of the disease, extensive fibrin deposition and perivascular fibrosis cause progressive luminal occlusion, and there is a striking paucity of small blood vessels in lesional tissue. Loss of vascular supply leads to chronic tissue hypoxia.

The initial vascular insult is apparently endothelial cell injury. Secondarily platelets may become activated and release mediators that may contribute to vasoconstriction, fibroblast activation and myofibroblast transdifferentiation. Endothelial dysfunction may lead to abnormal vascular dilation/constriction resulting in impaired blood flow responses and episodes of ischemia-reperfusion with oxidative stress that amplifies vascular injury. Endothelin-1, the most potent vasoconstrictor known, is reported to be elevated in patients with SSc, with higher levels in dcSSc than lcSSc. Obstructive vasculopathy of small blood vessels leads to tissue hypoxia and the described tissue remodelling. Vasculogenesis may be impaired in SSc and contribute to the progressive loss of blood vessels.

ii) Tissue Fibrosis:

Fibrosis is characterized by accumulation of excessive amounts of type I collagen and other fibrillar collagens, fibronectin, elastin, proteoglycans, and other connective tissue molecules in the extracellular matrix (ECM). The process causes disruption of tissue architecture. In SSc, interstitial and vascular fibrosis in the skin and internal organs contributes directly to their progressive dysfunction and eventual failure. Most prominently affected are the lungs, gastro-intestinal tract, heart, tendon sheath, and peri-fascicular tissue surrounding skeletal muscle.

Fibrosis in the skin, the hallmark of SSc, causes marked expansion of the dermis. The process obliterates the hair follicles, sweat glands, and other skin appendages. Collagen fiber accumulation is most prominent in the deep dermis, and gradually invades the subadjacent adipose layer with entrapment of fat cells. The proportion of a-smooth muscle actin-positive myofibroblasts that are intermediates between fibroblasts and contractile smooth muscle cells and play a major role in fibrogenesis, is increased in the lesional skin.

In early lung lesions, patchy infiltration of the alveolar walls with lymphocytes, plasma cells, macrophages, and eosinophils is seen. With progression, interstitial lung fibrosis and vascular damage predominate, often coexisting within the same lesions. Intimal thickening of the pulmonary arteries underlies PAH, and at autopsy is often associated with multiple pulmonary emboli and myocardial fibrosis. The typical histologic pattern seen on lung biopsy specimen is non-specific interstitial pneumonitis, a form of interstitial lung disease characterized by mild-to-moderate interstitial inflammation, type II pneumocyte hyperplasia, and uniform distribution of fibrosis. Less commonly, SSc is associated with the usual interstitial pneumonia pattern, which is characterized by scattered fibroblastic foci and patchy distribution of fibrosis. Progressive thickening of the alveolar septa ultimately results in obliteration of the airspaces and honeycombing, and consequent loss of pulmonary blood vessels. This process impairs gas exchange and contributes to increasing pulmonary arterial tension. The prevalence of interstitial lung disease in patients with dcSSc is reported to be about 53% and about 35% in patients with lcSSc.

In the gastrointestinal tract, pathologic changes can occur at any level from the mouth to the rectum. The esophagus is virtually always affected, with fibrosis in the lamina propria, submucosa, and muscular layers, and characteristic vascular lesions. Replacement of the normal intestinal architecture results in disordered peristaltic activity, gastroesophageal reflux and small bowel dysmotility, pseudo-obstruction, and bacterial overgrowth. Chronic gastroesophageal reflux is complicated by esophageal inflammation, ulcerations, and stricture formation.

In the kidneys, vascular lesions predominate, and glomerulonephritis is rare. Chronic renal ischemia is associated with shrunken glomeruli and other ischemic changes. Patients with acute scleroderma renal crisis show dramatic histological changes indistinguishable from other forms of malignant hypertension. Vascular changes in SSc kidneys are most prominent in the small interlobular and arcuate arteries, which show reduplication of elastic lamina, marked intimal proliferation, and accumulation of ground substance. These changes can also be found in SSc patients who do not have renal crisis. Fibrinoid necrosis of the arteriolar walls may be seen. Intimal thickening leads to severe narrowing and total obliteration of the lumen, often with microangiopathic hemolysis.

At autopsy evidence of cardiac involvement is found in 70% of patients with SSc. Modest pericardial effusions are common; occasionally fibrosis with constrictive pericarditis may occur. A characteristic pathologic finding is myocardial contraction band necrosis, which is thought to reflect ischemia-reperfusion injury. Significant interstitial and perivascular fibrosis may occur in the absence of clinically evident heart involvement.

Other organs with fibrotic alterations include the thyroid, penile blood vessels associated with erectile dysfunction, salivary and lacrimal glands. Synovial biopsy specimens show fibrosis and characteristic vascular changes in the small arterioles.

The cellular source of excessive deposition of collagen and other ECM constituents are fibroblast or fibroblast-like cells. Fibroblasts normally residing in the connective tissue or pericytes residing around blood vessels may become activated by growth factors such as TGF-β resulting in proliferation and increased collagen synthesis. Tissue injury, mechanical tension and TGF-β induce activation of fibroblast-like cells and a phenotypic change, resulting in the transformation of these cells into myofibroblasts, a process designated fibroblast-myofibroblast-transformation (FMT). Myofibroblasts are characterized by increased motility, expression of a smooth muscle actin, increased collagen synthesis, tissue inhibitors of metalloproteinases, and other ECM components. Myofibroblasts are a major source of TGF-β activation during the fibrotic response and are responsible for contraction of early granulation tissue. In pathologic fibrogenesis, myofibroblasts persist, resulting in excessively contracted ECM characteristic of chronic scars.

Immune Dysfunction:

The innate and adaptive arms of the immune system seem to be activated in early SSc, and autoimmunity is prominent; however, the role of cellular and humoral autoimmune effector pathways in the pathogenesis is uncertain.

In early stages of the disease, activated CD4 and CD8 lymphocytes and monocytes and macrophages, and less commonly B cells, eosinophils, mast cells, and natural killer cells, are observed in perivascular regions in the lesional skin, lungs, and other affected organs. Mononuclear cell infiltrates in skin are predominantly CD3CD4 positive T cells and express markers of activation.

Circulating autoantibodies with multiple antigenic specificities can be detected in virtually all patients with SSc.

Although SSc-associated autoantibodies have validated clinical utility as diagnostic markers, their contribution to disease manifestations is uncertain and it is unknown whether these autoantibodies precede, or are a consequence of, vascular injury, tissue damage and/or fibrosis. Target specificities and clinical associations are summarized in table 1.

TABLE 1

Autoantibody frequency and their main clinical associations

| Autoantibody type | Frequency (%) | Clinical Associations |
|---|---|---|
| Antinuclear antibody | 93-9 | lcSSc and dcSSc |
| Anti-centromere | 16-39 | lcSSc, PAH without ILD, PBC, protective for ILD abnd SRV |

TABLE 1-continued

Autoantibody frequency and their main clinical associations

| Autoantibody type | Frequency (%) | Clinical Associations |
|---|---|---|
| Anti-topoisomerase 1 | 9-39 | dcSSc > lcSSc, ILD, SDV |
| Anti-RNA polymerase | 4-25 | dcSSC, SRC |
| Anti-Th/to | 1-7 | lcSSc, ILD, PAH |
| Anti-U3RNP | 1-6 | dcSSc > lcSSc, severe disease, muscle involvement, PAH |
| Anti-PM-Scl | 0-6 | PM/DM overlap, arthritis overlap, ILD |
| Anti-Ku | 1-3 | Muscle and joint involvement |
| Anti-U1RNP | 5-35 | Overlap syndromes |
| Anti-U11/U12RNP | 1.6-5 | ILD |

Abbreviations:
PBC, primary biliary cirrhosis;
PM/DM, polymyositis/dermatomyositis;
SDV, severe digital vasculopathy;
SRC, scleroderma renal crisis.

SSc is typically associated with one or more of the following clinical characteristics: The clinical manifestations of SSc are protean, reflecting its complex underlying pathology. The frequency of various clinical features differs according to the stage and subset of the disease. The course and the severity of organ involvement are unpredictable in individual patients. In addition, the severity and activity of each complication needs to be considered in making treatment decisions. Fatigue and lethargy are common throughout the illness, although usually more pronounced in its early phases. Reactive depression is a frequent accompaniment to this often relentless and disfiguring disorder.

The prevalence of major organ manifestations reported in textbooks is given in table 2. Higher frequencies were recently published from the European Scleroderma Trials and Research (EUSTAR) cohort based on the characteristics of 7,655 patients, all fulfilling the 1980 ACR criteria for the clinical characteristics of the different involved organ systems are presented in a tabulated overview (tables 2 and 3). Typically, females are affected more often than males, with a predominance of 3-5:1 being reported.

TABLE 2

Clinical characteristics of SSc

Skin

In some cases edema initially (puffy hands and fingers, sometimes feet) followed by thickening and hardening of the skin, sometimes visible skin inflammation, sometimes hypo and hyperpigmentation. Distribution of skin lesions: distal extremities in localized cutaneous SSc (lcSSc) or in diffuse cutaneous SSc (dcSSc) with lesions extending proximally and involving truncal skin (see also table).
Raynaud's phenomenon. Episodic vasospasm induced by cold or emotional stress. Intermittent pallor followed by cyanosis, suffusion, or pain and tingling, and sometimes redness.
Telangectasias are dilated small blood vessels in the skin forming red spots. Telangiectasias in SSc are typically oval or rectangular in shape.
Abnormal nailfold capillaries.
Complications: loss of skin appendices (sweat glands, hair follicles) and subcutaneous fat, neural compression (e.g. carpal tunnel syndrome), adherence to tendons and joints, limited to absent joint motility, digital pitting scars and ulcers, digital gangrene, other skin ulcers (e.g. overlying the metacarpophalangeal joints) due to vascular involvement, impaired wound healing, infection of skin ulcers, calcinosis cutis (macroscopic tissue calcifications that can break through skin and also lead to chronic skin ulceration).

TABLE 2-continued

Clinical characteristics of SSc

Gastrointestinal tract

Mouth: perioral tight skin, reduced oral aperture, dental caries, xerostomia.
Esophagus: dysmotility, reflux; complications: strictures, hiatal hernia, Barrett's metaplasia (replacement of physiologic squamous epithelium by columnar epithelium with goblet cells, precancerous condition).
Stomach: gastroparesis with bloating and vomiting, gastric antral vascular ectasia with intermittent bleeding (can cause anemia).
Small bowel: hypomotiliy, stasis, bacterial overgrowth; complications: pseudoobstruction, diarrhea, bloating, malabsorption, weight loss, malnutrition, cachexia.
Large bowel: hypomotility, pseudodiverticulosis; complications: pseudoobstruction/megacolon, volvulus, pneumatosis cystoides intestinalis.
Rectum: sphincter incompetence.

Musculoskeletal system

Inflammatory synovitis and tendon friction rubs caused by inflammation in tendon sheath.
Fibrotic process in tendons, ligaments and joint capsules can contribute together with skin fibrosis to joint contractures.
Myopathy, myositis in case of SSc-/myositis overlap.
Osteolysis.

TABLE 3

Clinical characteristics of SSc cont.

Lung

Pulmonary fibrosis and/or alveolitis (interstitial lung disease, ILD) with breathlessness, especially on exertion, dry cough, bilateral inspiratory crackles at the lung bases, radiographic features of ILD (in conventional radiographs, in high resolution computer tomography (HRCT) with higher sensitivity and at earlier stages) and abnormal lung function tests (reduced Forced Vital Capacity, FVC; Total Lung Capacity, TLC; Diffusion Capacity of Lung for carbon monoxide, DLCO). The survival of patients with full blown SSC-ILD is much shorter than the survival of overall SSC patients.
Pulmonary hypertension (1) as a primary abnormality due to fibroproliferative abnormalities in the pulmonary vasculature (pulmonary arterial hypertension, PAH), (2) associated with disease of the left side of the heart, (3) associated with chronic hypoxia (due to ILD and loss of pulmonary vascular bed), (4) associated with chronic thromboembolism, including pulmonary occlusive disease. PAH usually does not manifest with dyspnea until quiet advanced stages. Reduced exercise capacity is a typical finding. PAH can be characterized by abnormal echocardiographic, pulmonary function and/or electrocardiographic findings, although right heart catheterization remains the gold standard and is required to confirm the diagnosis of PAH. Definitive diagnosis requires exclusion of thromboembolic disease, >25 mmHg of the mean pulmonary arterial pressure at rest or >30 mmHg with exercise. The prognosis of PAH associated with SSc is worse than idiopathic pulmonary arterial hypertension.
Aspiration pneumonitis.
Pleural effusions, pleuritis.
Bronchiectasis.
Lung cancer.

Heart

Myocardial enzyme elevation, ECG abnormalities including abnormalities of cardiac rate and rhythm, diastolic or global dysfunction as a consequence of myocardial ischemia, fibrosis, and/or myocarditis.
Pericardial effusion.
Complications: left ventricular or global heart failure, myocardial infarction, sudden death.

Kidney

Indolent chronic renal involvement with slow reduction of glomerular filtration rate and proteinuria.
Glomerulonephritis in case of SSc-systemic lupus erythematosus overlap.
Complication: scleroderma renal crisis characterized by severe arterial hypertension, that can cause heart failure, stroke or encephalopathy with generalized seizures, flash pulmonary edema, and progressive or acute renal failure with increased creatinine serum levels, proteinuria, microscopic hematuria, and sometimes microangiopathic haemolytic anemia and thrombocytopenia, can evolve into end stage renal disease requiring long-term dialysis or renal transplantation, early mortality in approximately 10%.

Classification:

The hallmark of SSc is induration and thickening of the skin ("scleroderma"), but also many internal organs can be involved in SSc. The two major clinical subsets are differentiated by the pattern of cutaneous involvement and additional associated clinical and laboratory features (Table 4). The CREST syndrome (acronym derived from calcinosis cutis, Raynaud's phenomenon, esophageal dysmotility, sclerodactyly, telangiectasias) has been individualized based on a combination of clinical features but may be classified as lcSSC. SSc can have features of other connective tissue diseases or fulfil their criteria. SSc without skin involvement ("scleroderma sine scleroderma") is rare and usually diagnosed late in the course due to absent skin signs. SSc in childhood and adolescence is extremely rare. Further classifications can be found in the section titled "Diagnosis and Symptoms".

TABLE 4

Key clinical features of SSc subsets

Diffuse cutaneous systemic sclerosis (dcSSc)

Proximal skin thickening involving the trunk, upper arms and thighs, in addition to symmetrical involvement of the fingers, hands, arms, face/neck.
Rapid onset of disease following the appearance of Raynaud's phenomenon.
Significant visceral disease: lungs, heart, gastrointestinal, and/or kidneys.
Absence of anti-centromere antibodies.
Variable disease course but overall poor prognosis, with survival of 40% to 60% at 10 years.
Limited cutaneous systemic sclerosis (lcSSc)

Symmetrical skin thickening limited to the areas below the elbows and knees and involving the face/neck.
Progression if disease typically months or years after the onset of Raynaud's phenomenon.
Later and less severe development of visceral disease.
Late development of pulmonary arterial hypertension.
Association with anti-centromere antibodies.
Relatively good prognosis with survival >70% at 10 years.
Overlap syndromes Diffuse or limited systemic sclerosis with typical features of one or more of the other defined connective tissue diseases.
Mixed connective tissue disease: features of systemic lupus erythematosus, systemic sclerosis and polymyositis in the presence of anti-U1 RNP antibodies.
CREST syndrome Subset of lcSSc with prominent calcinosis, Raynaud's phenomenon, esophageal dysmotility, sclerodactyly, and teleangiectasis (CREST).
Scleroderma sine scleroderma (SSc without skin involvement)

Raynaud's phenomenon, characteristic internal organ complications, and serologic abnormalities of SSc, but no apparent skin thickening and stiffening.

Diagnosis and Symptoms:

The diagnosis of SSc is usually made based on clinical manifestations, in particular the pattern of skin involvement. The American College of Rheumatology (ACR) has proposed diagnostic criteria to classify patients. Either one major criterion (i.e. proximal scleroderma) or two or more of the minor criteria (i.e. [1] sclerodactyly, [2] digital pitting scars of fingertips or loss of substance of the distal finger pad, [3] bilateral basilar pulmonary fibrosis) are required to classify patients as SSc.

When applied to case and disease comparison cohorts, the criteria had 97% sensitivity for definitive SSc and 98% specificity. These criteria appear not to include all patients with SSc. In the EUSTAR (EULAR Scleroderma Trials and Research group) cohort only 83.5% of patients fulfilled the 1980 ACR criteria, patients with early disease and overlap syndromes comprising the largest proportion of excluded group.

To overcome this issue, the ACR and the European League Against Rheumatism (EULAR) have agreed on revised criteria for SSc that should be published in the course of 2013. The revised criteria are given in FIG. 1.

A tissue biopsy is preferably not required for the diagnosis of SSc.

TABLE 5

The ACR-EULAR Criteria for the classification of Systemic Sclerosis

| Items | Sub-items | Weight/Score |
|---|---|---|
| Skin thickening of the fingers of both hands extending proximal to the metacarpophalangeal joints | | 9 |
| Skin thickening of the fingers (only count the highest score) | Puffy fingers | 2 |
| | Whole Finger, distal to MCP | 4 |
| Finger tip lesions (only count the highest score) | Digital Tip Ulcers | 2 |
| | Pitting Scars | 3 |
| Telangiectasia | | 2 |
| Abnormal nailfold capillaries | | 2 |
| Pulmonary arterial hypertension and/or Interstitial lung Disease | | 2 |
| Raynauds's phenomenon | | 3 |
| Scleroderma related antibodies (any of anti-centromere, anti-topoisomerasel [anti-ScL 70], anti-RNA polymerase III) | | 3 |
| TOTAL SCORE^: | | |

Patients having a total score of 9 or more are being classified as having definite systemic sclerosis. ^Add the maximum weight (score) in each category to calculate the total score.
1. These criteria are applicable to any patient considered for inclusion in a SSc study.
2. These criteria are not applicable to patients having a systemic sclerosis-like disorder better explaining their manifestations, such as: nephrogenic sclerosing fibrosis, scleredema diabeticorum, scleromyxedema, erythromyalgia, porphyria, lichen sclerosis, graft versus host disease, and diabetic chierarthropathy. Patients with "Skin thickening sparing the fingers" also are notclassified as having SSc.

Typical symptoms of SSc are given below in tabulated form (Table 6).

TABLE 6

Symptoms of SSc (clinical signs and other clinical features see Tables 2 and 3)

General

Fatigue, lethargy
Skin

Skin sclerosis: sensation of swollen hands or fingers, sometimes pain, sometimes pruritus, impaired manual dexterity/disability in daily private and professional life due to joint contractures and pain, impaired movement in other than finger and hand joints, decreased skin sensitivity due nerve compression, dry skin from loss of skin appendices.
Raynaud's phenomenon: usually painful, sometimes followed by tingling sensation.
Skin ulcers and digital gangrene: prolonged episodes of pain, sometimes severe pain.
Gastrointestinal tract Mouth: disfigurement.
Esophagus: retrosternal discomfort or pain, dysphagia, burning pain/heartburn,
regurgitation of gastric material in particular at night, bleeding from intestinal telangiectasias.
Stomach, small/large bowel, and rectum: early satiety, bloating, pain, symptoms of intestinal obstruction, constipation, fecal soiling.

TABLE 6-continued

Symptoms of SSc (clinical signs and other clinical features see Tables 2 and 3)

Musculoskeletal system

Pain due to synovitis and tendosynovitis.
Lung

Breathlessness/dyspnea, disability from breathlessness upon exertion or at rest, cough (typically dry), pain from pleuritis, multiple symptoms due to oxygen therapy and lung transplantation.
Heart Symptoms of myocardial ischemia including retrosternal pain, palpitations from abnormalities of heart rhythm, symptoms of heart failure.
Kidney Headache and blurred vision from severe hypertension, neurological symptoms from stroke and seizures, dyspnea from pulmonary edema, multiple symptoms from renal replacement (dialysis, transplantation).
Other Symptoms of depression from relentless disease, disfigurement and disability, low self-esteem, concerns with physical appearance and feelings about uncertainty about the future.

The average survival time from diagnosis of all SSc patients is reported to be approximately 13 years, whereas the 5-year survival rate of patients with SSc-ILD is reported to be 40-60%, showing the higher mortality rate in patients with SSc-ILD compared to overall SSc.

Death in SSc is typically due to SSc-organ involvement (~53%), cancer (~15%) or atherosclerosis. Death from SSc-organ involvement is more common in patients with diffuse skin involvement, older age at onset, and males.

Recently, the causes and risk factors for death in SSc were reported by the European League against Rheumatism (EULAR) Scleroderma Trials and Research (EUSTAR) database). The database included 5,860 SSc patients who fulfilled the ACR 1980 classification criteria. Causes of death and comorbidity data were available from 234 of 284 fatalities. They reported that 55% of deaths were directly related to SSc and 41% to non-SSc causes with the remaining 4% of cases considered nonclassifiable. Among the 284 deceased patients, 54.6% had diffuse cutaneous disease (dcSSc) and 40.5% had limited cutaneous disease (lcSSc). The median disease duration was 7.1 years for dcSSc and 15 years for lcSSc. 19% died of pulmonary fibrosis and 14% of pulmonary arterial hypertension. SSc-related myocardial disease death was 14% with most causes being related to arrhythmias. Renal causes of death only accounted for 4%, all of which were related to scleroderma renal crisis. Three percent of patients died from gastrointestinal-related causes. With respect to the non-SSc-related deaths, causes were as follows: infections (13% of all deaths), neoplasia (13%), and cardiovascular disease (12%). Patients with non-SSc-related deaths were then analyzed for SSc-related comorbidities. A significant number of patients who died from pneumonia also had presence of gastroesophageal reflux with or without documented aspiration. Of the fourteen patients who died from lung cancer, nine had concomitant pulmonary fibrosis. In this study, independent predictors of reduced survival included presence of proteinuria, pulmonary arterial hypertension, pulmonary restriction with a forced vital capacity of less than 80% predicted, presence of dyspnea greater than New York Heart Association Class II, higher age at onset of Raynaud's phenomenon, lower diffusion capacity for carbon monoxyde, and a modified Rodman skin score greater than 10. As 35% of all SSc related deaths were directly attributable to ILD, and 26% to PAH, this report reinforced the previous finding that ILD and PAH are the leading causes of SSc-related deaths and likely contribute to non-SSc-related deaths. In a recent systematic review and meta-analysis of 18 studies comprising 12,829 patients, the risk of death with cardiac, ILD, pulmonary hypertension and renal manifestations was elevated).

Presence of ILD is significantly associated with mortality in SSc. Decreased FVC is associated with mortality (VIRGINIA D. STEEN and THOMAS A. MEDSGER, JR., ARTHRITIS & RHEUMATISM, Vol. 43, No. 11, November 2000, pp 2437-2444, Assassi et al., Arthritis Rheum. 2009 Oct. 15; 61(10): 1403-1411).<70% FVC predicted higher mortality than >70% in SSc-ILD (Goh et al., ARTHRITIS & RHEUMATISM, Vol. 56, No. 6, June 2007, pp 2005-2012). Decline in FVC in the preceding 12, 18 and 24 months is believed to predict mortality.

In a retrospective study of 953 patients with SSc, patients with severe ILD had a 9-year survival rate of approximately 30%, whereas patients with SSc who did not have severe involvement of an organ system had a 9-year survival rate of 72%

Disability is a likewise threatening problem with fibrotic diseases and especially with SSc. For example, dyspnea is common in SSc (up to 50%). Principal contributing factors include ILD and PAH but bronchiectasis, alveolar hemorrhage, gastroesphageal reflux with aspiration due to esophageal dysmotility, arthritis, obesity, anemia and deconditioning due to physical inactivity may also contribute.

Dyspnea is a very important and independent predictor of function and health-related quality of life (HRQoL). FVC and pulmonary artery systolic pressure were significant independent predictors of dyspnea.

The disability index (DI) of the modified Health Assessment Questionnaire (HAQ) correlates with scleroderma heart, kidney disease, tendon friction rubs, hand contractures, and proximal muscle strength. An increased HAQ-DI is predictive of mortality and correlates with reduced first closure, reduced hand spread, and presence of tender joints. Disability in SSc worsens over time, with dyspnea and disease type being the strongest predictor of disability. Patients with digital ulcers have significantly higher global disability, hand disability, and anxiety. Most patients with SSc have limitation in daily activities and have an increased need for help at home. Skin involvement assessed by the modified Rodnan Skin Score (mRSS) is strongly associated with disability and pain. Comparing patients with SSc, psoriatic arthritis and rheumatoid arthritis joint involvement was more disabling in SSc than psoriatic arthritis and SSc patients experienced more pain than patients with rheumatoid arthritis. SSc is associated with a high prevalence of depression and anxiety. Depression is associated with ILD. Health related quality of life is reduced in SSc patients and similar to rheumatoid arthritis patients. Raynaud's phenomenon has impact on disability (overall, grip, eating dressing), pain, and mood. Pain and depressive symptoms are significant determinants of physical functioning and social adjustment.

Working disability and productivity loss is substantial in patients with SSc as concluded in a recent meta-analysis of work status. Standardized employment ratios reported were between 0.70 and 0.77 and the proportion of patients being employed ranged between 11.3% and 82%. Full and part-time sick leave rates are also increased as well as estimated lost productivity of paid labour. Work disability in SSc is reported to greater than in rheumatoid arthritis.

Thus, there is a very high unmet medical need for treatment options in the field of fibrosis, fibrotic diseases and especially so in SSc and related indications. Furthermore, there is a very high unmet medical need for prophylaxis options in order to prevent fibrosis, fibrotic diseases and especially so in SSc and related indications in subjects, preferably human subjects that are likely to develop it.

SUMMARY OF THE INVENTION

It has been found by the inventors that the known monoclonal anti-alpha v antibody DI17E6 (designated also as DI-17E, DI17e6, Abituzumab, abituzumab, EMR62242 or EMD 525797) is highly effective in interfering with cell signalling processes relevant for the development, occurrence and/or manifestation of fibrosis and especially of fibrotic disorders. Moreover, it has been found by the inventors that said anti-alpha v antibody DI17E6 is highly effective in interfering with cell signalling processes relevant for the development, occurrence and/or manifestation of systemic sclerosis. Evidence therefore is shown in the Experimental Section given herein and as discussed above and below. Thus, a subject of the instant invention is the monoclonal anti-alpha αv antibody DI17E6 and/or a biologically active variant or modification thereof, for use in the treatment of fibrosis and/or fibrotic disorders. A preferred subject of the instant invention is the monoclonal anti-alpha αv antibody DI17E6 and/or a biologically active variant or modification thereof, for use in the treatment of systemic sclerosis. A further subject of the instant invention is thus the use of the monoclonal anti-alpha αv antibody DI17E6 and/or a biologically active variant or modification thereof, for the manufacture of a medicament for the treatment of fibrosis and/or fibrotic disorders, and especially for the treatment of systemic sclerosis, and/or a method for the treatment of fibrosis and/or fibrotic disorders, and especially for the treatment of systemic sclerosis, comprising administering to a patient the monoclonal anti-alpha αv antibody DI17E6 and/or a biologically active variant or modification thereof. Due to its favorable safety profile, the monoclonal anti-alpha αv antibody DI17E6 and/or a biologically active variant or modification thereof are deemed suitable also for the prophylaxis of said disorders.

BRIEF DESCRIPTION OF FIGURES

FIG. 1: Abituzumab Blocks Abituzumab Blocks Elevated aSMA Expression in H358-Fibroblast and Calu3-Fibroblast Co-cultures FIG. 2 Abituzumab Blocks Elevated Expression of FMT-Related Genes in H358-Fibroblast Co-cultures FIG. 3 TGF-β Increases Integrins Expression in Human Lung Fibroblast FIG. 4 TGF-β Increases aSMA, IL-6 and other Myofibroblast Marker Gene Expression in Lung Fibroblast FIG. 5 Abituzumab Treatment of Fibroblast Cultures Reduces the TGF-β induced Increase in aSMA and IL-6

FIG. 6 Abituzumab Treatment Reduces TGFb-induced Collagen Gel Contraction

FIG. 7 Inhibition of αvβ6 6 binding to LAP by Abituzumab in comparison to anti-HEL-AB MSB0011523H-1 and 10D5, respectively FIG. 8 Strategie chart for finding the fibrosis/SSc signature FIG. 9 RGS5 expression by SSc and normal skin in GSE45485 with respective results of the moderated t-test comparing expression of RGS5 in SSc and normal skin FIG. 10 COL15A1 expression by early IPF, advanced IPF and normal lung in GSE24206 with respective results of the early IPF and healthy lung and advanced IPF and healthy lung, respectively FIG. 11 COL1A1 expression by early IPF, advanced IPF and normal lung in GSE24206 with respective results of the moderated t-test comparing expression of COL1A1 in early IPF and healthy lung and advanced IPF and healthy lung, respectively FIG. 12 COMP expression by IPAH (PPH), IPF, SSc-PAH, SSc-PF and normal lung (NL) in GSE48149 with respective results of the moderated t-test comparing expression of COMP in early IPF and normal lung and SSc-PF and normal lung, respectively FIG. 13 IGFBP2 expression by IPAH (PPH), IPF, SSc-PAH, SSc-PF and normal lung (NL) in GSE48149 with respective results of the moderated t-test comparing expression of IGFBP2 in early IPF and normal lung and SSc-PF and normal lung, respectively FIG. 14a SSP1 expression by IPAH (PPH), IPF, SSc-PAH, SSc-PF and normal lung (NL) in GSE48149 with respective results of the moderated t-test comparing expression of SSP1 in early IPF and normal lung and SSc-PF and normal lung, respectively FIG. 14b Signature Score of 19-gene fibrosis/SSc signature by SSc and normal skin in GSE45485 with results of the one-sided t-test comparing 19-gene Signature Score in SSc and normal skin FIG. 15a Signature Score of 19-gene fibrosis/SSc signature by SSc and normal skin in GSE32413 with results of the one-sided t-test comparing 19-gene Signature Score in SSc and normal skin FIG. 15b Signature Score of 9-gene TUAD signature by SSc and normal skin in GSE32413 with results of the one-sided t-test comparing 9-gene Signature Score in SSc and normal skin FIG. 16a Signature Score of 19-gene fibrosis/SSc signature by SSc and normal skin in GSE9285 with results of the one-sided t-test comparing 19-gene Signature Score in SSc and normal skin FIG. 16b Signature Score of 9-gene TUAD signature by SSc and normal skin in GSE9285 with results of the one-sided t-test comparing 9-gene Signature Score in SSc and normal skin FIG. 17a Signature Score of 19-gene fibrosis/SSc signature by early IPF, advanced IPF and healthy lung in GSE24206 with results of the one-sided t-test comparing 19-gene Signature Score in early IPF and normal lung and advanced IPF and normal lung, respectively FIG. 17b Signature Score of 9-gene TUAD signature by early IPF, advanced IPF and healthy lung in GSE24206 with results of the one-sided t-test comparing 9-gene Signature Score in early IPF and normal lung and advanced IPF and normal lung, respectively FIG. 18a Signature Score of 19-gene fibrosis/SSc signature by IPAH (PPH), IPF, SSc-PAH, SSc-PF and normal lung (NL) in GSE48149 with results of the one-sided t-test comparing 19-gene Signature Score in IPF and normal lung and SSc-PF and normal lung, respectively FIG. 18b Signature Score of 9-gene TUAD signature by IPAH (PPH), IPF, SSc-PAH, SSc-PF and normal lung in GSE48149 with results of the one-sided t-test comparing 9-gene Signature Score in IPF and normal lung and SSc-PF and normal lung, respectively FIG. 19a Signature Score of 19-gene SSc/fibrosis signature by Nash), steatosis, healthy obese and normal liver in GSE48452 with results of the one-sided t-test comparing 19-gene Signature Score in Nash, steatosis and heathy obese against control liver tissue, respectively FIG. 19b Signature Score of 9-gene TUAD signature by Nash, steatosis, heathy obese and normal liver in GSE48452 with results of the one-sided t-test comparing 9-gene Signature Score in Nash, steatosis and heathy obese against control liver tissue, respectively FIG. 20a Signature Score of 19-gene SSc/fibrosis signature mild and advanced stage liver fibrosis in GSE49541 with results of the one-sided t-test FIG. 20b Signature Score of 9-gene TUAD signature mild and advanced stage liver fibrosis in GSE49541 with results of the one-sided t-test FIG. 21a Signature Score of 19-gene SSc/fibrosis signature by Nash (Non-alcoholic fatty liver disease), PBC (primary biliary cholangitis), NAFLD (Non-alcoholic fatty liver disease), healthy obese and normal liver in GSE61260 with results of the one-sided t-test comparing 19-gene Signature Score in Nash, PSC, PBC and NAFLD against control liver tissue, respectively FIG. 21b Signature Score of 9-gene TUAD signature by Nash (Non-alcoholic fatty liver disease), PSC (Primary sclerosing cholangitis), PBC (primary biliary cholangitis), NAFLD (Non-alcoholic fatty liver disease), healthy obese and normal liver in GSE61260 with results of the one-sided t-test comparing 9-gene Signature Score in Nash, PSC, PBC and NAFLD against control liver tissue, respectively FIG. 22a Signature Score of 19-gene SSc/fibrosis signature by primary myelofibrosis and normal bone marrow in GSE44426 with the results of the one-sided t-test FIG. 22b Signature Score of 9-gene TUAD signature by primary myelofibrosis and normal bone marrow in GSE44426 with the results of the one-sided t-test

DETAILED DESCRIPTION OF THE INVENTION

The known monoclonal anti-alpha v antibody DI17E6 (designated herein also as Abituzumab, abituzumab, EMR62242 or EMD 525797) is found to be highly effective in interfering with cell signalling processes relevant for the development, occurrence and/or manifestation of fibrosis and especially of fibrotic disorders.

Without being bound by the mechanisms discussed in detail above and/or below and especially discussed below, it is strongly believed and sufficiently evidenced in the examples and data contained herein that due to the unique combination of the targeted site, the binding affinities/binding properties, and selectivity profile of antibody DI17E6, and preferably its biologically active variants or modifications thereof as discussed herein, the interaction of the antibody DI17E6, and preferably also its biologically active variants or modifications thereof as discussed herein, with the signalling pathways is crucial in the development of fibrosis and especially the pathways crucial for treating fibrosis and/or fibrotic disorders, especially the fibrotic disorders as described herein. In the light of our understanding of the results and data underlying the instant invention, the relevant pathways are discussed in more detail below.

In general, fibrotic diseases are characterized by excessive scarring due to production, deposition and contraction of extracellular matrix, which is believed to be driven by myofibroblast proliferation and activation. Fibrotic diseases represent one of the largest groups of diseases for which there is no effective therapy to date. The fibrotic processes are regulated by complex set of interactions within a network of profibrotic and antifibrotic mediators. TGF-β (i.e. Tranforming Groth Factor beta, often also referred to as TGFb, TGF b, TGFB, TGF B, TGF-b, TGF-B, TGFbeta, TGF beta or TGF-beta) signaling is believed to play an important role in fibroblast to myofibroblast transition (FMT) which contributes to increased extracellular matrix deposition, and thus is believed to be a main driver of disease.

TGF-β isoforms are synthesized as latent precursors complexed with latent TGF-β binding proteins, which contains a Latency Associated Peptide (LAP) region. There is substantial evidence for crosstalk between αv integrins and TGF-β during these processes. The LAP of TGF-β1 contains an RGD motif which interacts with the integrins αvβ1, αvβ3, αvβ5, αvβ6 and αvβ8 resulting in activation of TGF-β1. Abituzumab is a pan-αv integrin antibody that was found to allosterically to the ligand-binding αv subunit and thus prevents ligand from binding to all αvβ heterodimers and therefore inhibits αv integrin-dependent activation of latent TGF-p and thus blocks acquisition of the myofibroblast phenotype by fibroblasts and other precursors.

The obtained data demonstrate that the monoclonal anti-alpha αv antibody DI17E6 and/or a biologically active variant or modification thereof is capable of blocking multiple functions of αv integrins, including binding to RGD containing sequences in αv-integrin ligands, such as vitronectin, fibronection and the latency associated protein of TGF-β1 (LAP-β1).

Thus, one of the prominent functions of αv integrins is found to be the control of the activation of TGF-p. Therefore, based on the data discussed herein, it is believed that cytokine TGF-β is the main regulator of physiologic fibrogenesis and pathologic fibrosis, including SSc as described herein, and that the anti-αv integrin antibody DI17E6, or a biologically active variant or modification thereof, is able to control the activation of TGF-β in a manner that appears to be advantageous for the treatment of fibrosis, fibrotic diseases and/or systemic sclerosis.

Aside from this role, TGF-β has many other functions in tissue repair, angiogenesis, immunoregulation, and cell proliferation and differentiation. TGF-β can be secreted by platelets, monocytes/macrophages, T cells, and fibroblasts. Its signalling and cell regulation is highly complex.

Most TGF-β producing cells generate it as a biologically inactive precursor molecule that resides as a latent complex in the ECM reservoir and is unable to interact with its receptors. The conversion of latent TGF-β to its active form capable of binding its cell surface receptors is mediated by molecules such as thrombospondin-1, certain αvβx integrin heterodimers (FIG. 1), and various proteases, and is tightly regulated. Activated TGF-β binds to the type II TGF-β receptor, triggering of an intracellular signal transduction cascade that leads to induction of target genes. So far there is evidence for αvβ3, αvβ3, αvβ6 and αvβ8 can control the activation of TGF-β. This is described and discussed in more detail above and/or below.

The cytokine TGF-β is considered to be the main regulator of physiologic fibrogenesis and pathologic fibrosis, including SSc (see also the section relating to "Histopathological and pathophysiological characteristics"). The numerous cellular effects of TGF-β are described herein, and some of the most pertinent roles of TGF-β, including its connection and/or its association with integrins, are given in Table 7 (below).

TABLE 7

Fibrogenic activities of TGF-β

Recruits monocytes
Stimulates synthesis of collagens, fibronectin, proteoglycans, elastin, tissue inhibitor of metalloproteinases, inhibits matrix metalloproteinases
Stimulates fibroblast proliferation, chemotaxis
Induces fibrogenic cytokine production (CTGF), autoinduction, blocks synthesis and activity of interferon-gamma (IFN-γ)
Stimulates production of endothelin-1
Stimulates expression of surface receptors for TGF-β, PDGF
Induces fibroblast mitogenic responses to PDGF-AA
Promotes fibroblast-myofibroblast differentiation, monocyte-fibrocyte differentiation
Promotes epithelial-to mesenchymal transition (EMT)
Inhibits fibroblast apoptosis
Induces expression of αv integrins Thus, a preferred subject of the instant invention relates to the anti-αv integrin antibody DI17E6, or a biologically active variant or modification thereof, for use in the treatment of patients suffering from fibrotic diseases and especially systemic sclerosis (SSc). Preferably, the terms "fibrotic diseases" and/or "systemic sclerosis" have the meaning and characteristics as is known in the art. More preferably, the terms fibrotic diseases", and/or "systemic sclerosis" have the meanings and characteristics as described above and/or below.

Thus, a preferred subject of the instant invention relates to the anti-αv integrin antibody DI17E6, or a biologically active variant or modification thereof, for use in systemic sclerosis, wherein the systemic sclerosis comprises systemic sclerosis of the lung, liver, kidney, cardiovascular system and/or or skin. More preferably, the disease to be treated according to the invention is selected from systemic sclerosis of the lung, the liver and the kidney. Especially preferably, the disease to be treated according to the invention is the systemic sclerosis of the lung or comprises the systemic sclerosis of the lung.

Likewise preferred is the anti-αv integrin antibody DI17E6, or a biologically active variant or modification thereof, for use in systemic sclerosis, preferably for use in systemic sclerosis as described above and/or below in more detail, preferably wherein the systemic sclerosis affects one or more organs selected from the group consisting of lung, liver, kidney, heart and skin, more preferably lung, liver, kidney and/or heart, and especially lung or heart.

Also likewise preferred is the anti-αv integrin antibody DI17E6, or a biologically active variant or modification thereof, for use in the treatment of systemic sclerosis, preferably for use in the treatment of systemic sclerosis as described above and/or below in more detail, wherein the systemic sclerosis affects the cardiovascular system, the blood vessels and/or the blood. Thus, the disease to be treated according to the invention is preferably selected from diastolic dysfunction and myelofibrosis.

Thus, even more preferred is the anti-αv integrin antibody DI17E6, or a biologically active variant or modification thereof, for use, preferably for use as described in more detail above and/or below, wherein the systemic sclerosis comprises one or more indications selected from the group consisting of idiopathic pulmonary fibrosis, primary sclerosing cholangitis, non-alcoholic steatohepatitis (NASH), primary focal glomerulosclerosis, primary segmental glomerulosclerosis, diabetic nephropathy, diastolic dysfunction and myelofibrosis.

Thus, even more preferred is the anti-αv integrin antibody DI17E6, or a biologically active variant or modification thereof, for use, preferably for use as described in more detail above and/or below, wherein the systemic sclerosis comprises an indication or disease, wherein one or more of the clinical pictures or manifestations of both focal glomerulosclerosis, or primary focal glomerulosclerosis, and segmental glomerulosclerosis, or primary focal glomerulosclerosis, are present. Accordingly, even more preferred is the anti-αv integrin antibody DI17E6, or a biologically active variant or modification thereof, for use, preferably for use as described in more detail above and/or below, in the treatment of focal segmental glomerulosclerosis (FSGS).

Especially preferred is thus the anti-αv integrin antibody DI17E6, or a biologically active variant or modification thereof, for use, preferably for use as described in more detail above and/or below, wherein said treatment comprises patients suffering from pulmonary fibrosis and/or alveolitis (interstitial lung disease, ILD).

Alternatively preferred is the anti-αv integrin antibody DI17E6, or a biologically active variant or modification thereof, for use according to claim 1, wherein the disease to be treated is systemic sclerosis of the skin.

Preferably, the systemic sclerosis of the skin is selected from the group consisting of diffuse cutaneous systemic sclerosis (dcSSc) and limited cutaneous systemic sclerosis (lcSSc).

Especially preferred subjects of the invention include:

The anti-αv integrin antibody DI17E6 or a biologically active variant or modification thereof, preferably the anti-αv integrin antibody DI17E6, for use in the treatment of pulmonary fibrosis, alveolitis (interstitial lung disease, ILD), and/or sclerodermal interstitial lung disease (SSc-ILD).

The anti-αv integrin antibody DI17E6 or a biologically active variant or modification thereof, preferably the anti-αv integrin antibody DI17E6, for use in the treatment as described above and/or below, wherein said treatment comprises the administration of a dose, preferably an effective dose, of said antibody, or biologically active variant or modification thereof, in an amount of 10 mg-1000 mg per week or per two weeks.

The anti-αv integrin antibody DI17E6 or a biologically active variant or modification thereof, preferably the anti-αv integrin antibody DI17E6, for use in the treatment as described above and/or below, wherein said treatment comprises the administration of a dose, preferably an effective dose, of said antibody, or biologically active variant or modification thereof, in an amount of about 500 mg, about 1000 mg or about 1500 mg within 4 weeks or within a month. Preferably, the administration of said dose is repeated several times every 4 weeks or every month, respectively.

The anti-αv integrin antibody DI17E6 or a biologically active variant or modification thereof, preferably the anti-αv integrin antibody DI17E6, for use in the treatment as described above and/or below, wherein said treatment comprises the administration of a dose, preferably an effective dose, of said antibody, or biologically active variant or modification thereof, in an amount of about 500 mg every 4 weeks.

The anti-αv integrin antibody DI17E6 or a biologically active variant or modification thereof, preferably the anti-αv integrin antibody DI17E6, for use in the treatment as described above and/or below, wherein said treatment comprises the administration of a dose, preferably an effective dose, of said antibody, or biologically active variant or modification thereof, in an amount of about 1000 mg every 4 weeks.

The anti-αv integrin antibody DI17E6 or a biologically active variant or modification thereof, preferably the anti-αv integrin antibody DI17E6, for use in the treatment as described above and/or below, wherein said treatment comprises the administration of a dose, preferably an effective dose, of said antibody, or biologically active variant or modification thereof, in an amount of about 1500 mg every 4 weeks.

Preferably, said administration of said dose every 4 weeks or every month, respectively, is repeated at least 4 times, more preferably at least 8 times, even more preferably at least 16 times and especially at least 24 times.

Typically, said administration of said dose every 4 weeks or every month is repeated for about one year, for about one and a half year, for about 2 years, or for about two and a half or for about three years.

Thus, said administration of said dose every 4 weeks or every month, respectively, is preferably repeated not more than about 36 times, more preferably not more than about 28 times, even more preferably not more than about 24 times and especially not more than about 16 times or about 12 times.

Accordingly, preferred ranges for the duration of said repeated administrations are 4 to 36 months, 8 to 36 months, 12 to 36 months, 8 to 28 months, 12 to 28 months, or 16 to 28 months.

However, in principle, there is no upper limit for said repeated administration. However, it may be reasonable to stop said repeated administration, at least temporarily, after about half a year, after about one year, after about one and a half year, after about 2 years or after about two and a half years, e.g. in order to see how the patient's state evolved and to decide whether or not a new repeated administration shall be started. The above described repeated administration is especially preferred with regard to Abituzumab.

The anti-αv integrin antibody DI17E6 or a biologically active variant or modification thereof, preferably the anti-αv integrin antibody DI17E6, for use in the treatment as described above and/or below, and preferably for use as described in the paragraph directly above wherein the dose, preferably the effective dose, is administered in a single dose.

The anti-αv integrin antibody DI17E6 or a biologically active variant or modification thereof, preferably the anti-αv integrin antibody DI17E6, for use in the treatment as described above and/or below, and preferably for use as described in at least one of the two paragraphs directly above, wherein said antibody or said biologically active variant or modification thereof is administered as monotherapy.

The anti-αv integrin antibody DI17E6 or a biologically active variant or modification thereof, preferably the anti-αv integrin antibody DI17E6, for use as described above and/or below, wherein said biological active variant or modification comprises the CDR regions and heavy and light chain variable regions of DI17E6, which are at least 80% identical in amino acid sequence compared to the variable regions of DI17E6, preferably at least 90% identical in amino acid sequence compared to the variable regions of DI17E6, more preferably at least 95% identical in amino acid sequence compared to the variable regions of DI17E6, even more preferably at least 98% identical in amino acid sequence compared to the variable regions of DI17E6, and especially at least 99% identical in amino acid sequence compared to the variable regions of DI17E6.

The DI17E6 antibody for use as described above and/or below, and especially as described in the paragraph directly above, comprising one or more modifications within the heavy chain framework regions

```
FR1:
QVQLQQSGAELAEPGASVKMSCKASGYTFS      (SEQ ID No. 16)

FR2:
WVKQRPGQGLEWIG                      (SEQ ID No. 17)

FR3:
KATMTADTSSSTAYMQLSGLTSEDSAVYYCAS    (SEQ ID No. 18)

FR4:
WGQGTSVTVSS,                        (SEQ ID No. 19)
wherein one or more of the bold and underlined
positions are mutated and are different compared
to the original respective sequence.
```

The DI17E6 antibody and/or or a biologically active variant or modification thereof for use as described above and/or below, wherein the biological active variant or modification comprises a constant region, which is at least 80% identical in amino acid sequence compared to the constant region of DI17E6, preferably which is at least 90% identical in amino acid sequence compared to the constant region of DI17E6, more preferably which is at least 95% identical in amino acid sequence compared to the constant region of DI17E6, even more preferably which is at least 98% identical in amino acid sequence compared to the constant region of DI17E6, and especially which is which is at least 99% identical in amino acid sequence compared to the constant region of DI17E6.

The DI17E6 antibody and/or or a biologically active variant or modification thereof for use as described above and/or below, comprising a human IgG1 constant region instead of human IgG2, or a human IgG2 hinge region instead of the human IgG1 hinge.

Further especially preferred subjects of the instant invention include:

A method of treating fibrotic diseases, preferably systemic sclerosis and especially systemic sclerosis as described above and/or below, comprising administering to a patient the DI17E6 antibody and/or a biologically active variant or modification thereof, wherein the biologically active variant or modification comprises the CDR regions and heavy and light chain variable regions, which are 80%-95% identical in amino acid sequence compared to the variable regions of DI17E6.

A method of treating fibrotic diseases, preferably systemic sclerosis and especially systemic sclerosis as described above and/or below, comprising administering to a patient the DI17E6 antibody and/or a biologically active variant or modification thereof, wherein the biological active variant or modification comprises a constant region, which is at least 80%-98% identical with the amino acid sequence compared to the constant region of DI17E6.

A method of treating fibrotic diseases, preferably systemic sclerosis and especially systemic sclerosis as described above and/or below, comprising administering to a patient the DI17E6 antibody and/or a biologically active variant or modification thereof, comprising one or more modifications within the heavy chain framework regions

```
FR1:
QVQLQQSGAELAEPGASVKMSCKASGYTFS      (SEQ ID No. 16)

FR2:
WVKQRPGQGLEWIG                      (SEQ ID No. 17)
```

-continued

```
FR3:
KATMTADTSSSTAYMQLSGLTSEDSAVYYCAS   (SEQ ID No. 18)

FR4:
WGQGTSVTVSS,                        (SEQ ID No. 19)
wherein one or more of the bold and underlined
positions are mutated and are different compared
to the original respective sequence.
```

The respective method as described above and/or below, preferably as described directly above, comprising the administration of a modified DI17E6 antibody comprising a human IgG1 constant region instead of human IgG2, or a human IgG2 hinge region instead of the human IgG1 hinge region.

The safety results of the phase 1, open-label study showed that repeated infusions of single-agent DI17E6 (EMD 525797) at each of four dose levels are generally well tolerated and appear to be safe in patients. There are no dose-limiting toxicities (DLT) and no infusion reactions. With regard to dose, no trends in the distribution of TEAEs, NCI-CTCAE (version 3.0) grade or drug relationship are observed. In addition, there is no evidence of accumulation of any specific event within individual cohorts. Eleven patients experienced TEAEs that are considered to be drug-related. In this regard, skin symptoms such as pruritus, erythema and rash, which are reported in a total of four patients, are predictable adverse events associated with DI17E6 (EMD 525797) given that integrins are responsible for the maintenance of the epithelial phenotype. Symptoms of mucosal inflammation and swollen tongue may also be characteristic of the mechanism of action of EMD 525797, but together with fatigue, might also be signs of the underlying disease. The hematologic and biochemical toxicity shifts observed in eight patients could also be explained by underlying disease, as well as concomitant medications.

PK assessment after single and multiple doses of study drug suggest that DI17E6 (EMD 525797) behaved in accordance with a receptor-mediated clearance model as described for other antibodies targeting membrane-associated receptors. Consistent with the findings of an earlier study in healthy volunteers, PKs of DI17E6 (EMD 525797) in mCRPC patients are dose-dependent with clearance determined predominantly by the availability of unbound receptors. At the doses used in the present study, it can be assumed that at doses of 1000 mg or higher, almost all receptors are saturated and have a minor contribution to drug clearance. Immunologically triggered antibodies directed against DI17E6 can be detected in some (16%) patients; however, no impact on PKs or safety could be found.

In conclusion, single-agent EMD 525797 given as single and multiple doses is shown to be well tolerated in patients. No safety concern can be identified and there is to preliminary evidence of clinical benefit in numerous patients. Due to its target and safety profile, DI17E6 (EMD 525797) is a promising agent for single agent and/or combination therapy.

Thus, preferred subjects of the instant invention thus are:
The DI17E6 antibody as described above and/or below for use in the treatment of disorders as described above and/or below, wherein the dose, preferably the effective dose, of the antibody is 500 mg-1500 mg per two weeks or 1000-3000 mg per month, preferably 500-1000 mg per two weeks or 1000-2000 mg per month.

The DI17E6 antibody as described above and/or below for use in the treatment of disorders as described above and/or below, wherein the dose, preferably the effective dose, of the antibody is about 500 mg per month, about 1000 mg per month, about 1500 mg per month or about 2000 mg per month.

The DI17E6 antibody as described above and/or below for use in the treatment of disorders as described above and/or below, wherein the dose, preferably the effective dose, of 500-1000 mg is administered by a single infusion.

The DI17E6 antibody as described above and/or below for use in the treatment of disorders as described above and/or below, wherein the dose, preferably the effective dose, of 1000-2000 mg is administered by a single infusion.

The DI17E6 antibody as described above and/or below for use in the treatment of disorders as described above and/or below, wherein the dose, preferably the effective dose, of 500-1000 mg is administered by a single infusion once a month.

The DI17E6 antibody as described above and/or below for use in the treatment of disorders as described above and/or below, wherein the dose, preferably the effective dose, of 1000-2000 mg is administered by a single infusion once a month.

The DI17E6 antibody as described above and/or below for use in the treatment of disorders as described above and/or below, wherein the dose, preferably the effective dose, of about 500 mg is administered by a single infusion.

The DI17E6 antibody as described above and/or below for use in the treatment of disorders as described above and/or below, wherein the dose, preferably the effective dose, of about 1000 mg is administered by a single infusion.

The DI17E6 antibody as described above and/or below for use in the treatment of disorders as described above and/or below, wherein the dose, preferably the effective dose, of about 1500 mg is administered by a single infusion.

The DI17E6 antibody as described above and/or below for use in the treatment of disorders as described above and/or below, wherein the dose, preferably the effective dose, of about 1500 mg is administered by a single infusion once a month.

The DI17E6 antibody as described above and/or below for use in the treatment of disorders as described above and/or below, wherein the dose, preferably the effective dose, of about 1500 mg is administered by a single infusion once every 4 weeks.

The DI17E6 antibody as described above and/or below for use in the treatment of disorders as described above and/or below, wherein the antibody is administered in a monotherapy setting without additional cotherapeutic agents.

The DI17E6 antibody as described above and/or below for use in the treatment of disorders as described above and/or below, wherein the antibody is administered in an combination therapy setting in combination with additional cotherapeutic agents.

The DI17E6 antibody as described above and/or below for use in the treatment of disorders as described above and/or below, wherein the antibody is administered in an combination therapy setting in combination with MMF (Mycophenolat or Mycophenolate).

The DI17E6 antibody as described above and/or below for use in the treatment of patients with SSc-ILD, wherein the antibody is administered in a combination therapy setting in combination with MMF (Mycophenolat or Mycophenlate).

The DI17E6 antibody as described above and/or below for use in the treatment of patients with SSc-ILD, wherein the antibody is administered in an amount of about 500 mg per month, preferably in an amount of about 500 mg as a single administration once a month, in an combination therapy setting in combination with MMF (Mycophenolat or Mycophenolate).

The DI17E6 antibody as described above and/or below for use in the treatment of patients with SSc-ILD, wherein the antibody is administered in an amount of about 1.000 mg per month, preferably in an amount of about 1.000 mg as a single administration once a month, in an combination therapy setting in combination with MMF (Mycophenolat or Mycophenolate).

The DI17E6 antibody as described above and/or below for use in the treatment of patients with SSc-ILD, wherein the antibody is administered in an amount of about 1.500 mg per month, preferably in an amount of about 1.500 mg as a single administration once a month, in an combination therapy setting in combination with MMF (Mycophenolat or Mycophenolate).

The DI17E6 antibody as described above and/or below for use in the treatment of fibrosis, preferably excessive and/or pathological fibrosis, preferably in a manner as described above and/or below.

The DI17E6 antibody as described above and/or below for use in the treatment of fibrotic disorders, preferably fibrotic disorders as described above and/or below, preferably in a manner as described above and/or below.

The DI17E6 antibody as described above and/or below for use in the treatment of systemic sclerosis (SSc), preferably in a manner as described above and/or below.

The DI17E6 antibody as described above and/or below for use in the treatment of disorders as described above and/or below, wherein the organs affected by said disorders are selected from the group consisting of lung, liver, kidney, cardiovascular system or skin.

The DI17E6 antibody as described above and/or below for use in the treatment of fibrosis, preferably excessive and/or pathological fibrosis, preferably in a manner as described above and/or below, wherein the fibrosis, excessive fibrosis and/or pathological fibrosis affects one or more organs selected from the group consisting of lung, liver, kidney, heart and skin.

The DI17E6 antibody as described above and/or below for use in the treatment of fibrotic disorders, preferably fibrotic disorders as described above and/or below, preferably in a manner as described above and/or below, wherein said fibrotic disorder affects one or more organs selected from the group consisting of lung, liver, kidney, heart and skin.

The DI17E6 antibody as described above and/or below for use in the treatment of systemic sclerosis (SSc), wherein the systemic sclerosis comprises systemic sclerosis of the lung, liver, kidney, cardiovascular system and/or skin.

The DI17E6 antibody as described above and/or below for use in the treatment of systemic sclerosis (SSc), wherein said systemic sclerosis affects one or more organs selected from the group consisting of lung, liver, kidney, heart and skin.

The DI17E6 antibody as described above and/or below for use in the treatment of systemic sclerosis (SSc), wherein the systemic sclerosis affects the cardiovascular system, the blood vessels and/or the blood.

The DI17E6 antibody as described above and/or below for use in the treatment of systemic sclerosis (SSc), wherein said systemic sclerosis affects the lung and/or the skin.

The DI17E6 antibody as described above and/or below for use in the treatment of systemic sclerosis (SSc), wherein said systemic sclerosis affects the lung.

The DI17E6 antibody as described above and/or below for use in the treatment of systemic sclerosis (SSc), wherein said systemic sclerosis affects the skin.

The DI17E6 antibody as described above and/or below for use in the treatment of systemic sclerosis (SSc), wherein said systemic sclerosis affects the liver.

The DI17E6 antibody as described above and/or below for use in the treatment of systemic sclerosis (SSc), wherein said systemic sclerosis affects the kidneys.

The DI17E6 antibody as described above and/or below for use in the treatment of systemic sclerosis (SSc), wherein said systemic sclerosis affects the heart.

The DI17E6 antibody as described above and/or below for use in the treatment of systemic sclerosis (SSc), wherein the systemic sclerosis comprises one or more indications selected from the group consisting of idiopathic pulmonary fibrosis, primary sclerosing cholangitis, non-alcoholic steatohepatitis (NASH), primary focal glomerulosclerosis, primary segmental glomerulosclerosis, diabetic nephropathy, diastolic dysfunction and myelofibrosis.

The DI17E6 antibody as described above and/or below for use in the treatment of systemic sclerosis (SSc), wherein said systemic sclerosis comprises pulmonary fibrosis and/or alveolitis (interstitial lung disease, ILD).

The DI17E6 antibody as described above and/or below for use in the treatment of pulmonary fibrosis and/or alveolitis (interstitial lung disease, ILD).

The DI17E6 antibody as described above and/or below for use in the treatment of SSc-ILD or scleroderma-ILD.

The DI17E6 antibody as described above and/or below for use in the treatment of patients suffering from SSc-ILD.

The DI17E6 antibody as described above and/or below for use in the treatment of patients suffering from scleroderma-ILD.

The DI17E6 antibody as described above and/or below for use in the treatment of cutaneous systemic sclerosis (dcSSc) or limited cutaneous systemic sclerosis (lcSSc).

The DI17E6 antibody as described above and/or below for use in the treatment of subjects, preferably human subjects, with systemic sclerosis-associated interstitial lung disease (SSc-ILD).

Abituzumab for use in the treatment of subjects, preferably human subjects, with systemic sclerosis-associated interstitial lung disease (SSc-ILD).

The DI17E6 antibody as described above and/or below for use in the treatment of subjects, preferably human subjects, with SSc-ILD who already receive mycophenolate.

The DI17E6 antibody as described above and/or below for use in the treatment of subjects, preferably human subjects, with SSc-ILD who already receive mycophenolate, preferably constant doses of mycophenolate.

Abituzumab for use in the treatment of subjects, preferably human subjects, with SSc-ILD who already receive mycophenolate.

The biologically active variant or modification of said anti-αv integrin antibody DI17E6 as described above and/or below for use in the treatment of fibrosis and/or fibrotic disorders, wherein said biological active variant or modification comprises the CDR regions and heavy and light chain variable regions of DI17E6, which are at least 80% identical, at least 90% identical, at least 95% identical, at least 98% identical or at least 99% identical in amino acid sequence compared to the variable regions of DI17E6.

The biologically active variant or modification of said anti-αv integrin antibody DI17E6 as described above and/or below for use in the treatment of fibrosis and/or fibrotic disorders, wherein said biological active variant or modification comprises the heavy and/or light chain variable regions of DI17E6, which are at least 90% identical, at least 95% identical, at least 98% identical, at least 99% identical, or at least 99.5% identical in amino acid sequence compared to the respective heavy and/or light chain variable regions of DI17E6.

The biologically active variant or modification of said anti-αv integrin antibody DI17E6 as described above and/or below for use in the treatment of fibrosis and/or fibrotic disorders, wherein said biological active variant or modification comprises the heavy and/or light chain CDR regions of DI17E6, which are at least 90% identical, at least 92% identical, at least 94% identical, at least 96% identical, at least 98% or at least 99% identical in amino acid sequence compared to the respective heavy and/or light chain CDR regions of DI17E6.

The biologically active variant or modification of said anti-αv integrin antibody DI17E6 as described above and/or below, comprising one or more modifications within the heavy chain framework regions

```
FR1:
QVQLQQSGAELAEPGASVKMSCKASGYTFS    (SEQ ID No. 16)

FR2:
WVKQRPGQGLEWIG                    (SEQ ID No. 17)

FR3:
KATMTADTSSSTAYMQLSGLTSEDSAVYYCAS  (SEQ ID No. 18)

FR4:
WGQGTSVTVSS,                      (SEQ ID No. 19)
wherein one or more of the bold and underlined
positions are mutated and are different compared
to the original respective sequence of DI17E6,
for use in the treatment of fibrosis and/or
fibrotic disorders as described above and/or
below.
```

The biologically active variant or modification of said anti-αv integrin antibody DI17E6 as described above and/or below for use in the treatment of fibrotic disorders, preferably fibrotic disorders as described above and/or below, preferably in a manner as described above and/or below, wherein said fibrotic disorder affects one or more organs selected from the group consisting of lung, liver, kidney, heart and skin.

The biologically active variant or modification of said anti-αv integrin antibody DI17E6 as described above and/or below for use in the treatment of systemic sclerosis (SSc), wherein the systemic sclerosis comprises systemic sclerosis of the lung, liver, kidney, cardiovascular system and/or skin.

The biologically active variant or modification of said anti-αv integrin antibody DI17E6 as described above and/or below for use in the treatment of systemic sclerosis (SSc), wherein said systemic sclerosis affects one or more organs selected from the group consisting of lung, liver, kidney, heart and skin.

The biologically active variant or modification of said anti-αv integrin antibody DI17E6 as described above and/or below for use in the treatment of systemic sclerosis (SSc), wherein the systemic sclerosis affects the cardiovascular system, the blood vessels and/or the blood.

The biologically active variant or modification of said anti-αv integrin antibody DI17E6 as described above and/or below for use in the treatment of systemic sclerosis (SSc), wherein said systemic sclerosis affects the lung and/or the skin.

The biologically active variant or modification of said anti-αv integrin antibody DI17E6 as described above and/or below for use in the treatment of systemic sclerosis (SSc), wherein the systemic sclerosis comprises one or more indications selected from the group consisting of idiopathic pulmonary fibrosis, primary sclerosing cholangitis, non-alcoholic steatohepatitis (NASH or Nash), primary focal glomerulosclerosis, primary segmental glomerulosclerosis, diabetic nephropathy, diastolic dysfunction and myelofibrosis.

The biologically active variant or modification of said anti-αv integrin antibody DI17E6 as described above and/or below for use in the treatment of systemic sclerosis (SSc), wherein said systemic sclerosis comprises pulmonary fibrosis and/or alveolitis (interstitial lung disease, ILD).

The biologically active variant or modification of said anti-αv integrin antibody DI17E6 as described above and/or below for use in the treatment of pulmonary fibrosis and/or alveolitis (interstitial lung disease, ILD).

The biologically active variant or modification of said anti-αv integrin antibody DI17E6 as described above and/or below for use in the treatment of SSc-ILD or scleroderma-ILD.

A method of treating fibrosis and/or fibrotic diseases in a subject by administering the anti-αv integrin antibody DI17E6, or a biologically active variant or modification thereof, wherein said subject is characterized by a higher-than-threshold score calculated from a multi-gene signature comprising 2 or more, preferably 5 or more, more preferably 9 or more, even more preferably 15 or more and especially 16, 17, 18 or 19 genes, selected from the group consisting of the genes COL15A1 (NM_001855), COL1A1 (NM_000088), COMP (NM_000095), RGS5 (NM_003617), COL10A1 (NM_000493), COL5A1 (NM_000093), IGFBP2 (NM_000597), NM_005576, MOXD1 (NM_015529), ADRA2A (NM_000681), COL5A2 (NM_000393), MMP10 (NM_002425), TNFRSF21 (NM_014452), ITGA7 (NM_002206), TGF-β3 (NM_003239), MMP11 (NM_005940), SPP1 (NM_000582), CCL2 (NM_002982), and TNC (NM_002160), in particular the 9-gene signature based on the genes COL15A1 (NM_001855), COL1A1 (NM_000088), COMP (NM_000095), COL10A1 (NM_000493), COL5A1 (NM_000093), COL5A2 (NM_000393), ITGA7 (NM_002206), MMP11

(NM_005940), and TNC (NM_002160) hereafter also referred to as TUAD signature.

A method of monitoring the severity of fibrosis in fibrotic diseases and/or the emergence of fibrosis in diseases with potential to develop fibrosis in a subject by tracking the changes of a score calculated from a multi-gene signature comprising 2 or more, preferably 5 or more, more preferably 9 or more, even more preferably 15 or more and especially 16, 17, 18 or 19 genes, selected from the group consisting of the genes COL15A1 (NM_001855), COL1A1 (NM_000088), COMP (NM_000095), RGS5 (NM_003617), COL10A1 (NM_000493), COL5A1 (NM_000093), IGFBP2 (NM_000597), NM_005576, MOXD1 (NM_015529), ADRA2A (NM_000681), COL5A2 (NM_000393), MMP10 (NM_002425), TNFRSF21 (NM_014452), ITGA7 (NM_002206), TGF-β3 (NM_003239), MMP11 (NM_005940), SPP1 (NM_000582), CCL2 (NM_002982), and TNC (NM_002160), in particular the 9-gene signature based on the genes COL15A1 (NM_001855), COL1A1 (NM_000088), COMP (NM_000095), COL10A1 (NM_000493), COL5A1 (NM_000093), COL5A2 (NM_000393), ITGA7 (NM_002206), MMP11 (NM_005940), and TNC (NM_002160) hereafter also referred to as TUAD signature.

A method of treating fibrosis and/or fibrotic diseases in a subject by administering the anti-αv integrin antibody DI17E6, or a biologically active variant or modification thereof, wherein said subject is characterized by a gene signature comprising 2 or more, preferably 5 or more, more preferably 10 or more, even more preferably 15 or more and especially 16, 17, 18 or 19 genes, selected from the group consisting of the genes COL15A1 (NM_001855), COL1A1 (NM_000088), COMP (NM_000095), RGS5 (NM_003617), COL10A1 (NM_000493), COL5A1 (NM_000093), IGFBP2 (NM_000597), NM_005576, MOXD1 (NM_015529), ADRA2A (NM_000681), COL5A2 (NM_000393), MMP10 (NM_002425), TNFRSF21 (NM_014452), ITGA7 (NM_002206), TGF-β3 (NM_003239), MMP11 (NM_005940), SPP1 (NM_000582), CCL2 (NM_002982), and TNC (NM_002160), in particular the 9-gene signature based on the genes COL15A1 (NM_001855), COL1A1 (NM_000088), COMP (NM_000095), COL10A1 (NM_000493), COL5A1 (NM_000093), COL5A2 (NM_000393), ITGA7 (NM_002206), MMP11 (NM_005940), and TNC (NM_002160) hereafter also referred to as TUAD signature.

Use of DI17E6, or a biologically active variant or modification thereof, preferably a biologically active variant or modification thereof according as described herein, and especially abituzumab, for the manufacture of a medicament for the prophylaxis and/or treatment of fibrosis and/or fibrotic disorders.

Use of DI17E6, or a biologically active variant or modification thereof, preferably a biologically active variant or modification thereof according as described herein, and especially abituzumab, for the manufacture of a medicament for the prophylaxis and/or treatment of fibrosis and/or fibrotic disorders as described herein, and especially the prophylaxis and/or treatment of one or more indications selected from the group consisting of idiopathic pulmonary fibrosis, primary sclerosing cholangitis, non-alcoholic steatohepatitis (NASH), primary focal glomerulosclerosis, primary segmental glomerulosclerosis, diabetic nephropathy, diastolic dysfunction and myelofibrosis.

Use of abituzumab for the manufacture of a medicament for the prophylaxis and/or treatment of fibrosis and/or fibrotic disorders as described herein, and especially the prophylaxis and/or treatment of one or more indications selected from the group consisting of idiopathic pulmonary fibrosis, primary sclerosing cholangitis, non-alcoholic steatohepatitis (NASH), primary focal glomerulosclerosis, primary segmental glomerulosclerosis, diabetic nephropathy, diastolic dysfunction and myelofibrosis.

Use of abituzumab for the manufacture of a medicament for the prophylaxis and/or treatment of systemic sclerosis, preferably comprising pulmonary fibrosis, alveolitis (interstitial lung disease, ILD), and/or sclerodermal interstitial lung disease (SSc-ILD).

Use of abituzumab for the manufacture of a medicament for the prophylaxis and/or treatment of focal segmental glomerulosclerosis (FSGS).

Use of DI17E6, or a biologically active variant or modification thereof, preferably a biologically active variant or modification thereof according as described herein, and especially abituzumab, for the manufacture of a medicament for the prophylaxis and/or treatment of fibrosis and/or fibrotic disorders as described herein, wherein the treatment additionally comprises the administration of one or more active ingredients, selected from the group consisting of mycophenolic acid, mycophenolate, mycophenolate mofetil, mycophenolate sodium, methotrexate, amethopterin and prednisone.

Use of abituzumab for the manufacture of a medicament for the prophylaxis and/or treatment of fibrosis and/or fibrotic disorders as described herein, wherein the treatment additionally comprises the administration of mycophenolic acid, mycophenolate, mycophenolate mofetil and/or mycophenolate sodium.

Use of abituzumab for the manufacture of a medicament for the prophylaxis and/or treatment of fibrosis and/or fibrotic disorders as described herein, wherein the treatment additionally comprises the administration of methotrexate and/or amethopterin.

Use of abituzumab for the manufacture of a medicament for the prophylaxis and/or treatment of fibrosis and/or fibrotic disorders as described herein, wherein the treatment additionally comprises the administration of prednisone.

Due to its uniquely different mode of action, DI17E6, or a biologically active variant or modification thereof, preferably a biologically active variant or modification thereof according as described herein, and especially abituzumab, is deemed to be applicable in combination with basically all treatment options applied in the prophylaxis and/or treatment of fibrosis and/or fibrotic disorders, especially fibrosis and/or fibrotic disorders as described herein.

Thus, the addition of DI17E6, or a biologically active variant or modification thereof, preferably a biologically active variant or modification thereof according as described herein, and especially abituzumab, to treatment regimen that include the administration of a typical standard medicament in the treatment of fibrosis and/or fibrotic disorders, including, but not limited to one or more active ingredients, selected from the group consisting of mycophenolic acid, mycophenolate, mycophenolate mofetil, mycophenolate sodium, methotrexate, amethopterin and prednisone.

Thus, especially preferred is the anti-αv integrin antibody DI17E6, or the biologically active variant or modification thereof, for use as described above and/or below, preferably as described above, wherein said antibody, or said modification thereof, is the antibody with the registered International Non-proprietary Name (INN) Abituzumab. Likewise, especially preferred is a method as described above and/or below, preferably as described above, wherein said antibody, or said modification thereof, is the antibody with the registered International Non-proprietary Name (INN) Abituzumab. Likewise, especially preferred is the use of the anti-αv integrin antibody DI17E6, or the biologically active variant or modification thereof, for the manufacture of a medicament for the prophylaxis and/or treatment of fibrosis and/or fibrotic disorders, preferably as described above and/or below, and especially preferably as described above, wherein said antibody, or said modification thereof, is the antibody with the registered International Non-proprietary Name (INN) Abituzumab.

According to the instant invention, the anti-αv integrin antibody DI17E6, preferably also referred to herein as Abituzumab or abituzumab, is an engineered specifically tailored IgG2 hybrid monoclonal antibody directed to alpha-v integrin (receptor). This antibody is described in detail in WO 2009/010290, the disclosure of which is incorporated herein in its entirety.

Its hypervariable regions (CDRs) derive from murine mAb 17E6 (EMD 73034). This parent mouse IgG1 antibody is described, for example by Mitjans et al. (1995; J. Cell Sci. 108, 2825) and patents U.S. Pat. No. 5,985,278 and EP 719 859. Mouse mAb 17E6 is produced by hybridoma cell line 272-17E6 and deposited under accession number DSM ACC2160.

Its light chain domains derive from humanized monoclonal anti-EGFR antibody 425 (matuzumab). This antibody is described in detail for example in EP 0 531 472B1, and derives from its murine counterpart 425 (mouse MAb 425, ATCC HB9629), The antibody was raised against the human A431 carcinoma cell line and found to bind to a polypeptide epitope on the external domain of the human epidermal growth factor receptor (EGFR). Matuzumab has shown in clinical trials high efficacy.

Generally, the anti-αv integrin antibody DI17E6 as used according to the invention comprises:
(i) a CDR light and a heavy chain region deriving from mouse monoclonal anti-αv integrin antibody 17E6
(ii) a light chain framework region which is taken from humanized monoclonal anti-EGFR antibody 425,
(iii) a heavy chain framework region deriving from mouse monoclonal anti-αv integrin antibody 17E6, optionally comprising one or more mutations of amino acids at specific positions, and
(iv) a heavy chain constant region deriving from human IgG2 and a human constant kappa light chain region, wherein in said IgG2 domain the IgG2 hinge region was replaced by the human IgG1 hinge domain, and;
  wherein optionally one or more mutations within the IgG2 has been carried out.

Specifically, DI17E6 (designated as "DI17E6γ2h (N297Q)" or "EMD 525797") as used for the treatment as claimed and in the clinical trials as described above and below, has the following amino acid sequence:

(i) variable and constant light chain sequences (SEQ ID No. 1):
DIQMTQSPSSLSASVGDRVTITCRASQDISNYLAWYQQKPGKAPKLLIYY

TSKIHSGVPSRFSGSGSGTDYTFTISSLQPEDIATYYCQQGNTFPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
and (ii) variable and constant heavy chain sequences (SEQ ID No. 2):
QVQLQQSGGELAKPGASVKVSCKASGYTFSSFWMHWVRQAPGQGLEWIGY

INPRSGYTEYNEIFRDKATMTTDTSTSTAYMELSSLRSEDTAVYYCASFL

GRGAMDYWGQGTTVTVSSASTKGPSVFPLAPCSRSTSESTAALGCLVKDY

FPEPVTVSWNSGALTSGVHTFPAVLQSSGLYSLSSVVTVPSSNFGTQTYT

CNVDHKPSNTKVDKTVEPKSSDKTHTCPPCPAPPVAGPSVFLFPPKPKDT

LMISRTPEVTCVVVDVSHEDPEVQFNWYVDGVEVHNAKTKPREEQAQSTF

RVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK, wherein the underlined sequences represent the variable regions with the CDRs (in bold, identical with the parent mouse antibody). The modified IgG1 hinge region is represented by EPKSSDKTHTCPPCP (SEQ ID No. 3), and AQ is a substitution within the IgG2 domain.

However, as it was shown in WO 2009/010290, also variants of DI17E6 can be used according to the teaching of this invention. Thus, DI17E6 variants comprising one or more modifications within the heavy chain framework regions FR1:
QVQLQQSG<u>A</u>ELA<u>E</u>PGASVK<u>M</u>SCKASGYTFS    (SEQ ID No. 16)

FR2:
WVK<u>QR</u>PGQGLEWIG    (SEQ ID No. 17)

FR3:
KATMT<u>A</u>DTS<u>S</u>STAYMQ<u>L</u>S<u>GLT</u>SED<u>S</u>AVYYCAS    (SEQ ID No. 18)

FR4:
WGQGT<u>S</u>VTVSS,    (SEQ ID No. 19)

wherein one or more of the bold and underlined positions are mutated, can be used in the treatment of prostate cancer patients as described. In more detail, the following position heavy chain framework region is mutated at one, more or all of the following positions can be mutated: A9, E13, M20, K38, R40, A72, S76, Q82, G85, T87, S91 and S113. These variants show the same or very similar biological activity and efficacy as compared to DI17E6 defined by its sequences above.

In general, the invention as described includes also modifications and variants of the DI17E6 antibody that are functionally and/or pharmaceutically identical or similar to unmodified DI17E6, and wherein the CDR regions and heavy and light chain variable regions are at least 80%, at least 85%, at least 90%, at least 95%, at least 98%, or at least 99% identical in their amino acid sequence compared to the respective variable regions of DI17E6. In addition, the invention also includes modifications and variants of the DI17E6 antibody that are functionally and/or pharmaceutically identical or similar to unmodified DI17E6, and wherein the constant regions are at least 80%, or at least 85%, or at least 90%, or at least 95%, or at least 98%, or at least 99%, identical in their amino acid sequence compared to the respective constant regions of DI17E6. Changes in the constant regions of the IgG chains of the antibody may improve specific properties like immunogenicity, ADCC, and so on.

Preferably, the invention as described includes also modifications and variants of the DI17E6 antibody that are functionally and/or pharmaceutically identical or similar to (unmodified) DI17E6 or abituzumab, and wherein the heavy and light chain variable regions are at least 95%, at least 98%, at least 99% or at least 99.5% identical in their amino acid sequence compared to the respective heavy and light chain variable regions of DI17E6. In addition, the invention also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6. Changes in the constant regions of the IgG chains of the antibody may improve specific properties like immunogenicity, ADCC, and so on.

Even more preferably, the invention as described includes also modifications and variants of the DI17E6 antibody that are functionally and/or pharmaceutically identical or similar to (unmodified) DI17E6 or abituzumab, and wherein the CDR regions on the variable heavy and/or light chain are at least 90%, at least 92%, at least 94%, at least 96% or at least 98% identical in their amino acid sequence compared to the respective CDR regions on the variable heavy and/or light chain regions of DI17E6. In addition, the invention also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6.

Especially preferably, the invention as described includes also modifications and variants of the DI17E6 antibody that are functionally and/or pharmaceutically identical or similar to (unmodified) DI17E6 or abituzumab, wherein the heavy and light chain CDR regions are 100% identical to (unmodified) DI17E6 or abituzumab, but wherein the heavy and light chain variable regions other than said CDR regions are at least 95%, at least 98%, at least 99% or at least 99.5% identical in their amino acid sequence compared to the respective heavy and light chain variable regions of DI17E6. In addition, the invention preferably also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6.

Especially preferably, the invention as described includes also modifications and variants of the DI17E6 antibody that are functionally and/or pharmaceutically identical or similar to (unmodified) DI17E6 or abituzumab, wherein the CDR regions on the variable heavy and/or light chain are at least 90%, at least 92%, at least 94%, at least 96% or at least 98% identical in their amino acid sequence compared to the respective CDR regions on the variable heavy and/or light chain regions of DI17E6, and wherein the heavy and light chain variable regions other than said CDR regions are at least 95%, at least 98%, at least 99% or at least 99.5% identical in their amino acid sequence compared to the respective heavy and light chain variable regions of DI17E6. In addition, the invention preferably also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6.

Especially preferably, the DI17E6 antibody or abituzumab is a recombinant, de-immunized monoclonal antibody of the IgG2 subclass as described above and below which targets and inhibits ligand binding to human $\alpha v$-integrins. Especially preferably, the carbohydrate structures normally present in the Fc region of said DI17E6 antibody or abituzumab have been removed by genetically altering the amino acid residue that normally serves as the point of attachment rendering the molecule aglycosylated. The antibody is especially preferably composed of 4 polypeptide chains, 2 identical heavy chains consisting of 447 amino acids each and 2 identical light chains consisting of 214 amino acids each. Typically, the 4 chains are held together by a combination of covalent (disulfide) and non-covalent bonds. The approximate molecular weight of the molecule is 145 kDa.

More specifically, the DI17E6 antibody as described herein and especially abituzumab or EMD 525797 is characterized as a high affinity pan-$\alpha v$-integrin inhibitor, which has been shown in vitro to inhibit integrin-dependent activation of latent TGF-$\beta$, to inhibit FMT, to prevent upregulation of integrins on myofibroblasts, and to block contraction of myofibroblasts. Thus, it specifically binds to a unique epitope that is specific for the human $\alpha v$-integrin chain. Furthermore, it does not crossreact with other integrins such as the $\alpha 4\beta 1$ and the platelet fibrinogen receptor $\alpha IIb\beta 3$ and preferably does not trigger ADCC and CDC.

According to the invention, DI17E6 is believed to be highly effective in patients suffering from fibrotic diseases, more preferably systemic sclerosis and especially in one or more of the indications of systemic sclerosis described herein. More specifically, abituzumabis believed to be highly effective in patients suffering from fibrotic diseases, more preferably systemic sclerosis and especially in one or more of the indications of systemic sclerosis described herein.

Furthermore, it is believed that DI17E6 as described herein, and especially abituzumab, is suitable to provide a more effective and/or safer therapy of fibrotic diseases as described herein, will be better tolerated and can provoke better immune response than seen with the therapies previously known. Preferably, treatment with abituzumab is believed to be more effective, safer, will be better tolerated and can provoke better immune responses in the treatment of patients with SSc-ILD, preferably also patients who already receive constant doses of mycophenolate.

As described in the instant invention, TGF-$\beta$ is shown to be the master mediator of tissue fibrosis. Together with the findings that in patients with SSc, the TGF-$\beta$ signalling pathways are activated, and that some of the $\alpha v\beta x$ integrins heterodimers control the activation of TGF-$\beta$, the anti-$\alpha v$ integrin antibody DI17E6, or a biologically active variant or modification thereof, is believed to have a beneficial effect in SSc due to its shown interference with TGF-β activation, and additionally due its TGF-independent functions on αv integrins that are found to be involved in fibrosis. Therefore, EMD 525797 may be beneficial in patients with SSc through multiple modes of action. This is described in more detail above and/or below. However, DI17E6 cannot be directly tested in rodent models of fibrosis because of lacking cross-reactivity (see section A3.1.3 Mode of action). Preclinical models of fibrosis in nonhuman primates for SSc or SSc-ILD are deemed difficult, if not unfeasible. Preclinical experiments with blocking αv antibodies other than DI17E6 have been performed with human cells but contradicting results from in vivo experiments limit their relevance. Thus, herein we describe i.a. the effect of genetic or surrogate antibody mediated αv integrin blockade in preclinical fibrosis models in rodents, and, additionally, that there is more evidence for αv integrin blockade to support the SSc-ILD disease indication (acute lung injury responses, aberrant epithelial wound closure response, EMT) than SSc manifestations in other organs.

Although antibody mediated blockade of αvβ3 and αvβ5 integrins in vitro was shown to inhibit TGF-β dependent responses in human fibroblasts taken from tissue samples of either SSc or idiopathic pulmonary fibrosis (IPF) patients (Asano et al., American Journal of Pathology, Vol. 168, No. 2, February 2006, The Journal of Immunology, 2005, 175: 7708-7718, ARTHRITIS & RHEUMATISM, Vol. 52, No. 9, September 2005, pp 2897-2905, Journal of Investigative Dermatology (2006) 126, 1761-1769, Scotton et al., J. Clin. Invest. 119:2550-2563 (2009), so far, there is no convincing evidence that these integrins activate TGF-β in vivo. For example, the genetic deletion of αvβ3 and αvβ5 does not have an effect in bleomycin-induced lung fibrosis (Atabai et al., J. Clin. Invest. 119:3713-3722 (2009). However, the combination of genetic ablation of 138 integrin (Itgb8) with antibody inhibition of αvβ6 was shown to result in a more severe phenotype than in Itgb8−/− animals but a similar phenotype as seen in Tgfb1 null mice (Aluwihare et al., Journal of Cell Science 122, 2009, 227-232), discussing whether either or both integrins may play a role in the activation of TGF-β in in the biological development of in mice in the different states of differentiation from embryo to adult mice in vivo.

Takahashi et al. (Am. J. Respir. Cell Mol. Biol. Vol. 24, pp. 264-271, 2001) investigated the role of osteopontin in the pathogenesis of bleomycin-induced pulmonary fibrosis in mice. Osteopontin (OPN) is reported to be one of the cytokines produced by activated macrophages and mediates various functions, including cell attachment and migration, by interacting with av integrin.

These effects of OPN on fibroblasts were significantly suppressed by addition of antimouse av integrin monoclonal antibody (RMV-7) in this model.

Transforming growth factor beta (TGF-β) is an important driver of pulmonary fibrosis and therapeutic strategies to inhibit its actions are sought. However, TGF-β has other homeostatic roles that could make therapeutic inhibition problematic. Horan et al. (Am J Respir Crit Care Med Vol 177. pp 56-65, 2008) thus investigated Inhibition of the integrin avb6, a key activator of TGF-β in lung, using a monoclonal pSmad2/3 primary antibody that blocks avb6-mediated TGF-β activation, in murine bleomycin-induced lung fibrosis model. The partial inhibition of TGF-β using said avb6 integrin antibody was described as effective in blocking murine pulmonary fibrosis without exacerbating inflammation in said murine model.

Synthetic peptides containing the RGD sequence described to be able to inhibit integrin-related function in different cell systems. Moon et al. (Respiratory Research 2009, 10:18) investigated the effects of synthetic Arg-Gly-Asp-Ser (RGDS) peptide (SEQ ID NO: 20) on key inflammatory responses to intratracheal (i.t.) lipopolysaccharide (LPS) treatment and on the integrin signaled mitogen-activated protein (MAP) kinase pathway during the development of acute lung injury in mice. A pretreatment with RGDS SEQ ID NO: 20) inhibited LPS-induced increases in neutrophil and macrophage numbers, total protein levels and TNF-α and MIP-2 levels, and matrix metalloproteinase-9 activity in bronchoalveolar lavage (BAL) fluid at 4 or 24 h post-LPS treatment. Importantly, the inhibition of the inflammatory responses and the kinase pathways were still evident when this peptide was administered 2 h after LPS treatment. Similarly, a blocking antibody against αv integrin significantly inhibited LPS-induced inflammatory cell migration into the lung, protein accumulation and proinflammatory mediator production in BAL fluid, at 4 or 24 h post-LPS. These results suggest that RGDS (SEQ ID NO: 20) with high specificity for αvintegrins attenuates inflammatory cascade during LPS-induced development of acute lung injury in this murine model.

Activation of latent TGF-β by the αvβ6 integrin has been reported to be one critical step in the development of acute lung injury. Jenkins et al. (J. Clin. Invest. 116:1606-1614 (2006) show that thrombin, and other agonists of protease-activated receptor 1 (PAR1), activate TGF-β in an αvβ6 integrin-specific manner. This effect is PAR1 specific and is believed to be mediated by RhoA and Rho kinase. Intratracheal instillation of the PAR1-specific peptide TFLLRN (SEQ ID NO: 21) increases lung edema during high-tidal-volume ventilation, and this effect is described to be completely inhibited by a blocking antibody against the αvβ6 integrin. However, activation of TGF-β by αvβ6 probably requires more than simply binding to LAP, as we have identified cytoplasmic mutants that bind LAP but do not activate TGF-β. Furthermore, the αvβ1 and α8β1 integrins are both able to bind LAP but do not activate TGF-β. The PAR1-mediated enhancement of αvβ6-dependent TGF-β activation found in these in vitro experiments might be interpreted as one mechanism by which activation of the coagulation cascade contributes to the development of acute lung injury.

Transforming growth factor (TGF)-β family members regulate multiple aspects of wound repair through effects on cell proliferation, matrix production, and tissue inflammation, but the effects of TGF-β on wound closure itself have been controversial. Neuohr et al (Am. J. Respir. Cell. Mol. Biol. Vol. 35, pp 252-259, 2006) report that the used blocking antibodies to TGF-β enhanced the degree of closure of scratch wounds in primary airway epithelial monolayers in this airway epithelial cell culture model, while addition of exogenous TGF-1β inhibited the degree of closure, suggesting that endogenous activation of TGF-β might serve as a brake on the degree of wound closure. Blockade of TGF-β1 enhanced the degree of wound closure, whereas blockade of TGF-β2 had no effect in this cell culture model. Here, TGF-β1 (but not TGF-β2) could be activated by two members of the integrin family, αvβ6 and αvβ8, which both were found to be expressed on said airway epithelial cells. In the described model, wounding of the cell layer induced activation of TGF-β through effects of both integrins, but the chosen mouse monoclonal antibody against human αvβ8 (37E1) enhanced the degree of wound closure, whereas the chosen mouse monoclonal antibodies against human αvβ6 (anti-HEL-AB MSB0011523H-1, 10D5) did not.

Transforming growth factor-b1 (TGF-β1) is a potent mediator of the differentiation of fibroblasts into myofibroblasts, which is characterized by the appearance of the cytoskeletal protein a-smooth muscle actin. Lygoe et al. (Wound Rep. Reg. 2004; 12:461-470) describe that blockade of the αv and/or β1 integrins with selected monoclonal mouse anti-human antibodies (LM609 against αvβ3, P4C10 against β1, P1F6 against αvβ5, A11B2 against β1, L230 against αv) prevented the TGF-β1-induced myofibroblast differentiation, seen by the increased expression of a-smooth muscle actin and enhanced collagen gel contraction in three human fibroblast cell lines (from the mouth, skin, and kidney). Further, blockade of αv specific integrins αvβ5 and αvβ3 suppressed myofibroblast differentiation in fibroblasts from the mouth and skin; however, in the kidney cells, the prevention of differentiation was seen only with blockade of αvβ5 integrin but not αvβ3. These data indicate a role for αv integrins in the differentiation of human fibroblasts from the mouth, skin, and kidney into myofibroblasts and suggest that there might be a common differentiation pathway.

αv integrins might also participate in the optimal function of the angiogenesis through interaction with various growth factors such as Platelet Derived Growth Factor (PDGF), Vascular Endothelial Growth Factor (VEGF) and Fibroblast Growth Factor (FGF) factor. As BIBF-1120, a new chemical entity (NCE) from Boehringer Ingelheim, targets the tyrosine kinase of these receptors and has shown preliminary efficacy in a PoC trial in idiopathic pulmonary fibrosis (IPF), another form of lung fibrosis with features in common with SSc-ILD, DI17E6 is expected to have a potential beneficial effect through inhibition of these receptors. This is in line with inhibition of VEGF-induced ERK phosphorylation by DI17E6 observed with human cells.

Without being bound by the below discussed mechanism, based on the results underlying the instant invention, we believe that Epithelial-to-mesenchymal transition (EMT) contributes to fibrosis, fibrotic disorders and/or fibrosing lung disorders. TGF-β and αvβx integrins are believed to be involved in this transdifferentiation process and that blocking of the function of these integrins by the anti-αv integrin antibody DI17E6, or a biologically active variant or modification thereof downregulates EMT and thus become beneficial in fibrosis, fibrotic disorders and/or fibrosing lung disorders.

Oxidative stress is believed to play a role in fibrotic diseases. Cells expressing αvβx integrins are believed to be protected from oxidative stress induced apoptosis. It appears therefore to be possible that agents blocking the function of these integrins might increase apoptosis of fibroblasts and myofibroblasts.

Some of the αvβx integrins are found to be overexpressed in SSc-ILD and other forms of lung fibrosis, and the respiratory epithelium in lung biopsies from patients with SSc-ILD and IPF expresses increased levels of αvβ6 by immunohistochemistry. Increased numbers of αvβ3, αvβ5 and β6 expressing T cells are found in the bronchoalveolar lavage fluid from patients with SSc compared to normal controls (Luzina et al., Am J Respir Crit Care Med Vol 177. pp 56-65, 2008. However, it has been shown that 136 integrin knockout mice develop lung inflammation, but do not proceed to develop pulmonary fibrosis, after bleomycin exposure (Luzina et al., ARTHRITIS & RHEUMATISM, Vol. 48, No. 8, August 2003, pp 2262-2274).

Dermal fibroblasts from patients with SSc display enhanced expression of αvβ3 and αvβ5, and elevated TGF-β activation, which is inhibited by blocking antibody P1F6 directed against αvβ5 (Asano et al., ARTHRITIS & RHEUMATISM Vol. 52, No. 9, September 2005, pp 2897-2905; Journal of Immunology, 2005, 175: 7708-7718; American Journal of Pathology, Vol. 168, No. 2, February 2006; Journal of Investigative Dermatology (2006) 126, 1761-1769). Increased immunostaining with an anti-αvβ5 antibody is found in fibroblastic foci in lungs of patients with IPF (Scotton et al., J. Clin. Invest. 119:2550-2563 (2009)).

Cartilage oligomeric protein (COMP) is an extracellular matrix (ECM) protein that resides in cartilage, tendon, and other connective tissue. COMP is overexpressed in skin biopsies from patients with SSc. In SSc, serum COMP levels are elevated, predict mortality, and correlate with lung function decline and skin fibrosis as measured with the modified Rodnan Skin Score (mRSS). COMP is also one of the four signature RNAs in SSc skin that predict severity of skin involvement.

Yang et al. describe that Periostin facilitates skin sclerosis via PI3K/Akt dependent mechanism in a mouse model of scleroderma (Yang L, Serada S, Fujimoto M, Terao M, Kotobuki Y, et al. (2012) PLoS ONE 7(7): e41994 doi: 10.1371/journal.pone.0041994). Using skin from patients and healthy donors, also the expression of periostin was assessed by immunohistochemistry and immunoblotting analyses. Furthermore, it was found that recombinant mouse periostin directly induced Col1a1 expression in vitro, and this effect was inhibited by blocking the av integrin-mediated PI3K/Akt signaling either with anti-av functional blocking antibody or with the PI3K/Akt kinase inhibitor LY294002. As a result, it is concluded that Periostin plays an essential role in the pathogenesis of Bleomycin-induced scleroderma in mice and that Periostin may represent a potential therapeutic target for human scleroderma.

Wu et al. (Journal of Investigative Dermatology (2012) 132, 1605-1614) investigated the role of osteopontin (OPN), a matricellular protein with proinflammatory and profibrotic properties, in systemic sclerosis and dermal fibrosis in mice in the bleomycin-induced fibrosis model. According to that, OPN-deficient mice developed less dermal fibrosis compared with wild-type (WT) mice in said fibrosis model. Finally, they found TGF-β production by OPN-deficient macrophages to be reduced compared with WT. In conclusion, OPN levels are reported to be increased in SSc patients, and the data obtained are deemed to suggest that OPN might play an important role in the development of dermal fibrosis in mice, and that OPN thus might be a therapeutic target in SSc.

Plasma of a total of 70 patients with SSc was analysed by Lorenzen et al. (Rheumatology 2010; 49:1989-1991 doi: 10.1093/rheumatology/keq223 Advance Access publication 20 Jul. 2010), with twenty age-matched healthy volunteers and 59 patients with idiopathic pulmonary hypertension as controls. The results may indicate the possibility of using OPN inhibitors as a novel therapeutic target of T-cell chemotaxis, since monoclonal OPN antibodies have been used in collagen-induced arthritis models. In conclusion, OPN levels were described to parallel the development of pulmonary fibrosis in SSc and thus might be an attractive biomarker of this complication.

In summary, based on the results and data underlying the instant invention, we strongly believe that the specific interaction of DI17E6, and preferably also the biologically active variants or modifications thereof as described herein, with the αvβx integrins controls the activation of TGF-β and multiple additional mechanisms in a specifically advantageous manner that addresses the pathogenesis of fibrosis, fibrotic disorders, including SSc. Therefore, an advantageously beneficial effect of said interaction with the signalling in fibrosis, fibrotic disorders, preferably SSc, and in particular in SSc-ILD, is expected.

The excellent safety and tolerability of EMD 525797 in various cancer indications is expected to be similar in fibrotic diseases, including SSc and especially including SSc-ILD. Together with the expected benefit of EMD 52579, the benefit/risk ratio of EMD 525797 in SSc-ILD should be positive in SSc-ILD and greater than for CYC. EMD 525797 is thus believed to be also beneficial on other manifestations of SSc.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; mouse gonadotropin-associated peptide; inhibin; activin; vascular endothelial growth factor (VEGF); integrin; thrombopoietin (TPO); nerve growth factors such as NGFβ; platelet-growth factor; transforming growth factors (TGFs) such as TGF-α and TGF-β; erythropoietin (EPO); interferons such as IFNα, IFNβ, and IFNγ, colony stimulating factors such as M-CSF, GM-CSF and G-CSF; interleukins such as IL-1, IL-1a, IL-2, IL-3, IL-4, IL-5, IL-6, IL-7, IL-8, IL-9, IL-10, IL-11, IL-12, and TNFα or TNFβ. Preferred cytokines according to the invention are interferons and TNFa.

An "anti-angiogenic agent" refers to a natural or synthetic compound which blocks, or interferes with to some degree, the development of blood vessels. The anti-angiogenic molecule may, for instance, be a biological molecule that binds to and blocks an angiogenic growth factor or growth factor receptor. The preferred anti-angiogenic molecule herein binds to a receptor, preferably to an integrin receptor or to VEGF receptor. The term includes according to the invention also integrin (receptor) inhibitors.

The term "integrin inhibitors" or "integrin receptor inhibitors" refers to a natural or synthetic molecule that blocks and inhibit an integrin receptor. In some cases, the term includes antagonists directed to the ligands of said integrin receptors (such as for $\alpha_v\beta_5$: vitronectin, fibrin, fibrinogen, von Willebrand's factor, thrombospondin, laminin; for $\alpha_v\beta_5$: vitronectin; for $\alpha_v\beta_1$: fibronectin and vitronectin; for $\alpha_v\beta_6$: fibronectin). Antagonists directed to the integrin receptors are preferred according to the invention. Integrin (receptor) antagonists may be natural or synthetic peptides, non-peptides, peptidomimetica, immunoglobulins, such as antibodies or functional fragments thereof, or immunoconjugates (fusion proteins). Preferred integrin inhibitors of the invention are directed to receptor of $\alpha_v$ integrins (e.g. $\alpha_v\beta_3$, $\alpha_v\beta_5$, $\alpha_v\beta_6$ and sub-classes). Preferred integrin inhibitors are $\alpha_v$ antagonists, and in particular $\alpha_v\beta_3$ antagonists. Preferred $\alpha_v$ antagonists according to the invention are RGD peptides, peptidomimetic (non-peptide) antagonists and anti-integrin receptor antibodies such as antibodies blocking $\alpha_v$ receptors. Exemplary, non-immunological $\alpha_v\beta_3$ antagonists are described in the teachings of U.S. Pat. Nos. 5,753,230 and 5,766,591. Preferred antagonists are linear and cyclic RGD-containing peptides. Cyclic peptides are, as a rule, more stable and elicit an enhanced serum half-life. A preferred further integrin antagonist of the invention is, however, cyclo-(Arg-Gly-Asp-DPhe-NMeVal) (EMD 121974, Cilengitide®, Merck KGaA, Germany; EP 0770 622) which is efficacious in blocking the integrin receptors $\alpha_v\beta_3$ and $\alpha_v\beta_5$, and to a lesser extend $\alpha_v\beta_1$, $\alpha_v\beta_6$, $\alpha_v\beta_8$, $\alpha_{IIb}\beta_3$. A combination therapy of DI17E6 together with Cilengitide in fibrotic disease patients can be effective according to the invention.

DI17E6 is administered usually by intravenous injection, however other administration forms convenient in the art for antibody/protein drugs are applicable. All standard infusion solutions and formulation are applicable, such as described in WO 2005/077414 or WO 2003/053465, including liposomal formulations. It is, in addition, favorable to provide human serum albumin nanoparticles loaded with DI17E6 and optionally (to increase cytotoxicity) chemotherapeutic drugs (Biomaterials 2010, 8, 2388-98; Wagner et al.).

Especially preferred as the anti-αv integrin antibody DI17E6, or DI17E6, according to the instant invention is the antibody with the registered International Non-Proprietary Name (INN) Abituzumab.

In connection with the instant invention, Abituzumab is a recombinant, de-immunized monoclonal antibody of the IgG2 subclass that targets and blocks ligand binding to the human αv-integrins. In addition, the carbohydrate structures normally present in the Fc region have been removed by genetically altering the amino acid residue that normally serves as the point of attachment rendering the molecule aglycosylated. Accordingly, the antibody Abituzumab is preferably composed of four polypeptide chains, two preferably identical heavy chains consisting of 447 amino acids each and two preferably identical light chains consisting of 214 amino acids each. The four chains are held together by a combination of covalent (disulfide) and non-covalent bonds. The approximate molecular weight of the molecule is 145 kDa.

The antibody Abituzumab can be produced by mammalian cell culture in a serum-free growth medium. The antibody be purified by affinity and ion-exchange chromatography. The process may also include specific viral inactivation and removal steps. The antibody Abituzumab may be then transferred into formulation buffer and brought to the desired concentration.

Description and Composition of a Preferred Medicinal Product:

Abituzumab, e.g. in the concentration of 250 mg/10 mL can be used as the final drug product as a sterile solution intended for intravenous (i.v.) administration. Abituzumab drug product can be supplied in a 30 R type I glass vial, e.g. closed with a grey butyl rubber stopper and for example sealed with an aluminum/red polypropylene flip-off seal. Such vials can be used as single-use vial contains, e.g. containing 250 mg of Abituzumab as a 25 mg/mL preservative-free citrate buffered saline solution, for example containing polysorbate 80 (Tween® 80) as stabilizer. Such vials may contain a sufficient overage to remove a 10 mL volume of Abituzumab final drug product. Generally, for such a final drug product of Abituzumab, only excipients are used that are regarded as safe and conform to current European Pharmacopeia (EP) or United States Pharmacopeia (USP) or both.

Especially preferably, Abituzumab is a humanized IgG2 antibody that is genetically modified not to induce antibody-dependent cell cytotoxicity (ADCC) or complement-dependent cytotoxicity (CDC). Said Abituzumab antibody binds to the human αv-integrin receptor subunit with high specificity, thereby inhibiting ligand binding to the αv heterodimers (αvβ1, αvβ3, αvβ5, αvβ6, αvβ8). It specifically inhibits αv-integrins and blocks αv-integrin-mediated cell attachment and migration. It does not cross-react with other integrins, including the platelet fibrinogen receptor αIIbβ3, and recognizes only human and monkey αv-integrins. Abituzumab recognizes an epitope on the αv-integrin receptor subunit that is not located in or close to the ligand pocket. Therefore, its mechanism of action differs from that described for pure ligand-competing antagonists such as cyclic RGD peptides. The integrins αvβ3 and αvβ5 are selectively expressed on activated endothelial cells (EC), on resting platelets, smooth muscle cells, in the thyroid, on some kidney endothelia and epithelia, on the fallopian tube endothelium, and on osteoclasts. Furthermore, αv-integrins are expressed to a variable extent on malignant cells from different tumor entities, including those from colorectal cancer and prostate cancer. Accordingly, the binding of Abituzumab to its target preferably functionally blocks the integrin receptor and thus inhibits its binding to the corresponding extracellular matrix (ECM) ligand (i.e. vitronectin).

Immunohistochemical (IHC) examinations in humans and in different animal species showed that Abituzumab is highly species-specific: Abituzumab binds only to human and cynomolgus monkey αv-integrins, with comparable cross-reactivity between human and monkey tissues. Abituzumab has been shown in vitro to interfere with several aspects involved in tumor angiogenesis, such as EC attachment to ECM, destabilization of focal contacts, EC migration, transmission of angiogenic growth factor signaling (VEGF-induced ERK phosphorylation) and EC viability. Abituzumab also directly affects the tumor cells. In vitro experiments revealed that Abituzumab can affect cell adhesion to the ligands of αv-integrins and proliferation of tumor cells.

In vivo, the anti-tumor effect of Abituzumab was evaluated using different αv-integrin expressing tumor cell lines for tumor xenograft models (e.g., melanoma, NSCLC, CRC, prostate cancer). As Abituzumab is specific for human and monkey αv-integrins, its anti-angiogenic activity cannot be studied in conventional rodent xenograft tumor models. Therefore, the xenograft tumor experiments in mice demonstrated solely the potential anti-tumor activity of Abituzumab. Abituzumab was able to inhibit the growth in in vivo tumor experiments using cancer cell lines or primary explants of different indications (e.g., melanoma, NSCLC, prostate cancer and CRC).

The anti-angiogenic mechanism of action of Abituzumab was evaluated in a human skin xenograft/tumor cell line experiment in the absence of the target αv-integrins on the malignant cells. Abituzumab inhibited the growth of human αv-integrin-deficient melanoma cells injected into human skin that had been transplanted onto SCID mice. Because of the absence of the target on the tumor cells themselves, Abituzumab can target only the human endothelial cells, and tumor growth reduction is most likely caused by inhibition of tumor angiogenesis. Systemic administration of Abituzumab in cynomolgus monkeys blocked the induction of angiogenesis in subcutaneously implanted Matrigel plugs containing angiogenic growth factors to stimulate angiogenesis.

Especially preferred according to the invention are subjects as described herein, wherein the characteristics of two or more preferred, more preferred and/or especially preferred embodiments, aspects and/or subjects are combined into one embodiment, aspect and/or subject. Preferably, according to this invention, preferred subjects or embodiments can be combined with other preferred subjects or embodiments; more preferred subjects or embodiments can be combined with other less preferred or even more preferred subjects or embodiments; especially preferred subjects or embodiments can be combined with other just preferred or just even more preferred subjects or embodiments, and the like.

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

In any case, the term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of at least plus/minus 5%.

The terms "disorder(s)" and "disease(s)" as used herein are well-known and understood in the art. In the context of the present invention they are preferably used as synonyms and thus are preferably interchangeable, if the context they are used herein does not strongly implicate otherwise. Accordingly, the terms "fibrotic disorder(s)" and "fibrotic disease(s)" as used herein are also well-known and understood in the art. In the context of the present invention they are preferably used as synonyms and thus are preferably interchangeable, if the context they are used herein does not strongly implicate otherwise.

In the medical context, including, but not limited to treatment regimens, dosing schedules and clinical trial designs, for convenience and/or ease of use by patients, medical staff and/or physicians, as well as reliability and/or reproducibility of results etc., the terms "week"/"a week", "month"/"a month" and/or "year"/"a year" can used with slight deviations from the definitions of the Gregorian calendar. For example, in said medical context, a month is often referred to as 28 days, and a year is often referred to 48 weeks.

Thus, in the context of the instant invention, the term "week" or "a week" preferably refers to a period of time of about 5, about 6 or about 7 days, more preferably about 7 days.

In the medical context, the term "month" or "a month" preferably refers to a period of time of about 28, about 29, about 30 or about 31 days, more preferably about 28, about 30 or about 31 days.

In the medical context, the term "year" or "a year" preferably refers to a period of time of about 12 months or to a period of time of about 48, about 50, or about 52 weeks, more preferably 12 months, or about 48 or about 52 weeks.

The invention is explained in greater detail below by means of examples. The invention preferably can be carried out throughout the range claimed and is not restricted to the examples given here.

Moreover, the following examples are given in order to assist the skilled artisan to better understand the present invention by way of exemplification. The examples are not intended to limit the scope of protection conferred by the claims. The features, properties and advantages exemplified for the processes, compounds, compositions and/or uses defined in the examples may be assigned to other processes, compounds, compositions and/or uses not specifically described and/or defined in the examples, but falling under the scope of what is defined in the claims.

Thus, the following examples describe the invention in more detail but do not limit the invention and its scope as claimed.

EXAMPLES

Example 1

Myofibroblast Differentiation is Induced in Epithelial-Fibroblast Co-Cultures and is Inhibited by Abituzumab

LIST OF ABBREVIATIONS

αSMA: Alpha Smooth Muscle Actin
BSA: Bovine Serum Albumin
Cy5: Cyanine 5
DAPI: 4′,6-Diamidnino-2-Phenylindole
ECM: Extracellular Matrix
FGM: Fibroblast Growth Medium
FMT: Fibroblast to Myofibroblast Transition
FITC: Fluorescence Isothiocyanate
IXM: Image Xpress Micro Screening System
ug: Micgrogram
mg: Milligram
mL: Milliliter
ng: Nanogram
NHDF: Normal Human Dermal Fibroblasts
NHLF: Normal Human Lung Fibroblasts
PBS: Phosphate-Buffered Saline
TGF-β1: Transforming Growth Factor-Beta 1
ELISA: Enzyme-Linked Immunosorbent Assay
FBS: Fetal Bovine Serum
IL Interleukin Summary TGF-$\beta$1 is a potent mediator of fibroblast to myofibroblast transition (FMT) which contributes to increased extracellular matrix deposition and is main driver of fibrotic diseases. There is substantial evidence for crosstalk between $\alpha$v integrins and TGF-$\beta$ during these processes. TGF-$\beta$ is secreted in a latent form which contains a Latency Associated Peptide (LAP) region. The LAP of TGF-$\beta$1 contains an RGD motif which interacts with the integrins $\alpha$v$\beta$1, $\alpha$v$\beta$3, $\alpha$v$\beta$5, $\alpha$v$\beta$6 and $\alpha$v$\beta$8 resulting in activation of TGF-$\beta$1. Abituzumab is a human antibody specific for $\alpha$v and therefore inhibits $\alpha$v$\beta$1, $\alpha$v$\beta$3, $\alpha$v$\beta$5, $\alpha$v$\beta$6 and $\alpha$v$\beta$8.

The ability of abituzumab to block FMT was examined using an epithelial cell/fibroblast co-culture, mimicking the potential interaction of epithelial cells and fibroblasts in tissues undergoing fibrosis. Co-culture of NCI-H358 or Calu3 cells with fibroblasts resulted in induction of aSMA and multiple mRNA transcripts that are markers for FMT and also increased IL-6 production. In this system these markers were reduced by abituzumab treatment, demonstrating that $\alpha$v integrins play a role in FMT.

Introduction

Fibrotic diseases are characterized by excessive scarring due to production, deposition and contraction of extracellular matrix and is believed to be driven by myofibroblast proliferation and activation. Fibrotic diseases represent one of the largest groups of diseases for which there is no effective therapy. The fibrotic processes is regulated by complex set of interactions within a network of profibrotic and antifibrotic mediators. TGF-$\beta$ signaling is believed to play an important role in fibroblast to myofibroblast transition (FMT) which contributes to increased extracellular matrix deposition and is main driver of disease.

TGF-$\beta$ isoforms are synthesized as latent precursers complexed with latent TGF-$\beta$ binding proteins, which contains a Latency Associated Peptide (LAP) region. There is substantial evidence for crosstalk between $\alpha$v integrins and TGF-$\beta$ during these processes. The LAP of TGF-$\beta$1 contains an RGD motif which interacts with the integrins $\alpha$v$\beta$1, $\alpha$v$\beta$3, $\alpha$v$\beta$5, $\alpha$v$\beta$6 and $\alpha$v$\beta$8 resulting in activation of TGF-$\beta$1. Abituzumab is a pan-$\alpha$v integrin antibody that binds allosterically to the ligand-binding $\alpha$v subunit and thus prevents ligand from binding to all $\alpha$v$\beta$ heterodimers and therefore inhibits $\alpha$v integrin-dependent activation of latent TGF-$\beta$ and thus blocks acquisition of the myofibroblast phenotype by fibroblasts and other precursors.

Nature and Purpose of Study

The purpose of the present study was to determine the ability of abituzumab to block TGF-$\beta$ activation and FMT in vitro and thus showing its potential as a therapeutic agent for fibrotic diseases.

Materials and Methods

Test Systems

The test system is epithelial cell/fibroblast co-culture, mimicking the potential interaction of epithelial cells and fibroblasts in tissues undergoing fibrosis. Normal human lung fibroblast (NHLF) or Normal human dermal fibroblast (NHDF) from healthy donors were cocultured with NCI-H358 or Calu 3 cell line.

| Description | Company | Cat # | Lot# | Tissue # |
|---|---|---|---|---|
| Normal human lung fibroblasts | Lonza/clonetics | CC-2512 | 0000374386 | 26789 |
| Normal human lung fibroblasts | Lonza/clonetics | CC-2512 | 0000343490 | 25745 |
| Normal human lung fibroblasts | Lonza/clonetics | CC-2512 | 0000369145 | 26646 |
| Normal human dermal fibroblasts | Lonza/clonetics | CC-2511 | 0000399829 | 27240 |
| Normal human dermal fibroblasts | Lonza/clonetics | CC-2511 | 0000352805 | 26086 |
| Normal human dermal fibroblasts | Lonza/clonetics | CC-2511 | 0000281135 | 23920 |
| NCI-H358 bronchioalveolar cell line; From human, non-small cell lung carcinoma | Merck KGaA, Cell Culture Strain Collection, So-ABB4 | ATCC-CRL-5807 | NCI-H358 P4 WCB Aug. 7, 2013 | N/A |
| Calu-3 airway epithelial cell line; From human lung adenocarcinoma | Merck KGaA, Cell Culture Strain Collection, So-ABB4 | ATCC HTB 55 | Calu-3/10 Feb. 4, 2008 | N/A |

Test Material and Stimulus

| Antibodies | Company | Lot/Accession# |
|---|---|---|
| Abituzumab (DI17E6) | EMD Serono | 402499 |
| Anti-HEL IgG2 | EMD Serono | A12-145-2 |

Supplies and Instruments

| Material/Reagent | Provider | Cat. # | Lot # |
|---|---|---|---|
| FGM Fibroblast Growth Medium and Bullet Kit (include Cat#CC-3131 & CC-4126) | Lonza/clonetics | CC-3132 | 354178 |
| Fibroblast Growth Medium | Lonza/clonetics | CC-3131 | 409065 |
| Fibroblast Bullet Kit | Lonza/clonetics | CC-4126 | 417247 |
| Gentamicin-Sulfate | Lonza/clonetics | CC-4081J | 417245 |
| Insulin | Lonza/clonetics | CC-4021J | 417243 |
| rhFGF | Lonza/clonetics | CC-4065J | 417244 |
| FBS | Lonza/clonetics | CC-4101J | 417246 |
| RPMI medium 1640 | Life Technology | 11875-093 | 1627680 |
| Heat Inactivated Fetal Bovine Serum | Corning | 35-076-CV | 35076102 |
| Sodium Pyruvate | Life Technology | 11360-070 | 1585688 |
| DMEM | Life Technology | 11965-092 | 1621394 |
| Reagent Pack/Subculture Reagents | Lonza/clonetics | CC-5034 | 409088 |
| Hepes Buffered Saline | Lonza/clonetics | CC-5022 | 362157 |
| Trypsin | Lonza/clonetics | CC-5012 | 372708 |
| Trypsin Neutralizing Solution | Lonza/clonetics | CC-5002 | 385562 |
| T 150 cm2 flasks | Corning | 430825 | 19514018 |
| UltraPure Distilled Water | Invitrogen | 10977-015 | 1607416 |
| PBS | Invitrogen | 20012-027 | 1457916 |
| Collagen 1 Cell ware 96-well Black/Clear Plate | BD Biosciences | 356700 | 2136233 |
| 24 well plates | Falcon | 353047 | N/A |
| Odyssey Blocking Buffer (500 mL) | Li-COR | 927-40000 | T1752 |
| BD Cytofix/Cytoperm Fixation/Permeabilization kit | BD Biosciences | 554714 | 3099684 |
| Fixation Solution | BD Biosciences | 554722 | 3231840 |
| Permeabilization (Perm) Wash Buffer | BD Biosciences | 554723 | 4174605 |
| Anti-actin, smooth muscle, clone ASM-1 | Millipore | CBL171 | 2377949 |
| Goat Anti-mouse IgG Alexa Fluor488: Invitrogen Corp | Invitrogen | A11001 | 1503602 |
| Goat Anti-rabbit IgG Alexa Fluor647: Invitrogen Corp | Invitrogen | A21245 | 1623067 |
| DAPI, dilactate | Sigma Aldrich | D9564-10MG | 042M4005 |
| RNeasy 96 kit | Qiagen | 74181 | 148019008 |
| RT2 First Strand kit | Qiagen | 330401 | N/A |
| RT2 Profiler PCR Array (Custom) | Qiagen | 12473 | N/A |

| Equipment: | Company | Serial # |
|---|---|---|
| Allegra X-14R Centrifuge | Beckman Coulter | B34604-AA |
| Laminar hood model 1395, 1300 SeriesA2 | Thermo Fisher | 114627-128 |
| Incubator at 37 C. with humidified 5% CO2 | Thermo Fisher | 313910-5441 |
| Spectramax M5e | Molecular Devices | MVE06101 |
| Biotek 405LS microplate washer | Perkin Elmer | 1306126 |
| Microscope, Nikon TMS | DSC Optical Services | 11345 |
| Water Bath | Equipnet | 35933-2-2 |
| Image Xpress Micro Imaging Microscope | Molecular Devices | 12264 |
| Optiplex 990 Image Analysis Computer | Dell | X16-96076 |
| QuantStudio 12K Flex | Applied Biosystems by Life Technologies | 285880466 |

Experimental Design
Outline Study Design

Fibroblast culture media (FGM with 2% FBS): FGM™-2 BulletKit™ (CC-3132) contains one 500 ml bottle of Fibroblast Cell Basal Medium (CC-3131) and Fibroblast Bullet Kit (CC-4126) with the following growth supplements: 0.5 ml hFGF-B (CC-4065J); 0.5 ml Insulin (CC-4021J); 10 ml FBS (CC-4101J); 0.5 ml GA-1000 (CC-4081J).

Fibroblast culture media for FMT assays (FGM with 0.1% FBS): FGM™-2 BulletKit™ (CC-3132) contains one 500 ml bottle of Fibroblast Cell Basal Medium (CC-3131) and Fibroblast Bullet Kit (CC-4126) with the following growth supplements: 0.5 ml hFGF-B (CC-4065J); 0.5 ml Insulin (CC-4021J), 0.5 ml FBS (CC-4101J), 0.5 ml GA-1000 (CC-4081J).

NCI-H358 medium: 500 ml RPMI with 55 ml of heat inactivated FBS+5 ml of sodium pyruvate Calu-3 media: 500 ml DMEM with 55 ml of heat inactivated FBS NHLF and NHDF were grown in T150 tissue culture flasks in FGM with 2% FBS until they were 70-80% confluent on the day of the assay. The cells were rinsed with 6 ml HEPES buffered saline solution (Lonza Cat #CC-5022), trypsinized with 6 ml trypsin/EDTA (Lonza Cat #CC-5012) for 5 min at room temperature. The trypsin was inactivated with 6 ml trypsin neutralizing solution (Lonza Cat #CC-5002), spun down at 400 g for 4 min and washed once with FGM with 2% FBS.

For imaging studies, fibroblasts (NHLF or NHDF) were seeded at 10,000 cells/well in Collagen 1 Cellware 96-well Black/Clear Plate. Cells were cultured for 8 hours in FGM with 2% FBS. Media were aspirated and cells were starved overnight in FGM containing 0.1% FBS. Media were aspirated and 100 ul of FGM with 0.1% FBS containing abituzumab or anti-HEL IgG at a conc of 20 ng/ml were added and incubated for 30 min. For coculture: NCI-H358 or Calu-3 were plated into the wells containing fibroblast at a density of 2,000 cells in 100 ul of NCI-H358 or Calu-3 media. 5 days later, media were collected and stored at −80 C for IL-6 detection. Cells were fixed and stained according to the alpha smooth muscle actin (αSMA) staining procedure.

For gene expression studies, fibroblasts (NHLF or NHDF) were seeded at 200,000 cells/well in 24 wells culture plates. Cells were cultured for 8 hours in FGM with 2% FBS. Media were aspirated and cells were starved overnight in FGM containing 0.1% FBS. Media were aspirated and 300 ul of FGM with 0.1% FBS containing abituzumab or anti-HEL IgG at a conc of 20 ng/ml were added and incubated for 30 min. For coculture: NCI-H358 or Calu-3 were plated into the wells containing fibroblast at a density of 40,000 cells in 300 ul of NCI-H358 or Calu-3 media. 7 days later, media were collected and stored at −80 C for IL-6 detection. Cells were stored at −80 C until ready for RNA isolation and RT-PCR.

aSMA immunofluorescence staining: Cells were washed 2 times with PBS (200 ul in 96 well plates), and then fixed with Fixation/Permeabilization Solution for 45 mins at room temperature (50 uL in 96 well plate). Cell were then washed 3 times with 5 min incubation using 1×BD perm wash buffer (diluted in distilled water at 1:10 dilution). The cells were blocked with Odyssey block buffer (50 ul in 96 well plates) for 60 min at room temperature. The plates were washed 2 times with 5 min incubation between each wash using 1×BD perm wash buffer (200 ul in 96 well plates). Anti-SMA antibody were added at 1:100 dilution in wash buffer and incubated for 3 h at room temperature. Plates were then washed 2 times with 1×BD perm wash buffer (200 ul in 96 well plate). Secondary Ab Goat Anti-mouse IgG conjugated with Alexa Fluor 488 were used at 1:200 dilution in perm wash buffer in a final volume of 100 ul and incubated for 1 h at room temperature. Cells were washed 2 times using 200 ul 1×BD perm wash buffer with 5 minutes incubation between each washes. DAPI were added to wash buffer at 1:1000 dilution and 200 ul were added to the plated, incubated for 5 min at room temperature, solution were aspirated and replaced with 200 ul of 1×BD perm wash buffer.

For gene expression analysis. RNA were extracted according to the "RNeasy 96 Protocol for Isolation of Cytoplasmic RNA from Animal Cells-using Vaccum Technology" included in the RNeasy 96 Kit (Qiagen). cDNA Synthesis was done using the RT2 First Strand Kit and Real-Time PCR for RT2 profiler PCR arrays with cycling conditions for Applied Biosystems cyclers according to the procedures described in the RT2 Profiler PCR Array Handbook (Qiagen).

Read-Outs

Plate Reading Procedure for Imaging

Image Xpress Micro (IXM) machine and the MetaXpress software program were used for image acquisition and analysis. For 2 color staining: DAPI and FITC staining, plate acquisition imaging protocol: "2014-YW-SMA488-DAPI-10x" were used. For data analysis, multi wavelength cell scoring analysis parameter protocol "2014-5-7-YW-SMA488-DAPI-4x-2 para a" were used to quantify the amount of SMA fiber induction due to FMT. Images of individual well were downloaded as BMP files.

IL-6 ELISA

Levels of human IL-6 were determined using a commercial IL-6 ELISA assay (Human Duoset IL-6, R & D Systems) following the manufacturer's instructions. Optical density reading (OD) at 450 nm are performed using Spectramax M5e reader (Molecular Devices) and IL-6 concentration for each sample extrapolated from a four-parameter logistic curve fit calculated using OD reading from the internal IL-6 standard.

Gene Expression Analysis

After RT-PCR has completed the run in the QuantStudio 12k flex Applied Biosystem cycler, CT values for all wells were downloaded to Excel spreadsheet for calculation of relative expression.

Computer Programs Used

| Program | Version | Supplier |
|---|---|---|
| Microsoft Office | 2007/2013 | Microsoft |
| GraphPad Prism | 5.02 | GraphPad |
| QuantStudio 12k flex Real time PCR system | 1.2.2 | Applied Biosystem |
| MetaXpress Image Analysis Software | 3.1.0.97 | Molecular Devices |
| Adobe Photoshop CS6 | 13.0 X32 | Adobe |

Relative Gene Expression (Basal Level) and Fold Change Calculations $C_T$ Threshold cycle. The $C_T$ is the cycle number at which the fluorescence generated within a reaction crosses the threshold line. $C_T$ values are logarithmic and are used either directly for quantitative analyses.

For Relative Gene Expression (Basal Level):

Calculate the $\Delta C_T$ value. $\Delta C_T = C_{T\ target} - C_{T\ reference\ (GAPDH)}$ Calculate the $2^{-\Delta C_T}$ as relative gene expression at basal level.

For Relative Gene Expression (Fold Change after Treatment):

Calculate the $\Delta C_T$ value. $\Delta C_T = C_{T\ target} - C_{T\ reference\ (GAPDH)}$ Calculate the $\Delta\Delta C_T$ value. $\Delta\Delta C_T = \Delta C_T$ test sample(treatment)−$\Delta C_T$ calibrator sample(without treatment)

The amount of target, normalized to an endogenous reference (e.g. GAPDH) and relative to a calibrator (before treatment or control), is given by: $2^{-\Delta\Delta C_T}$ Results Abituzumab Blocks Elevated aSMA Expression in H358-Fibroblast and Calu3-Fibroblast Co-Cultures (See Also FIG. 1)

The study produced substantial evidence for the hypothesized crosstalk between av integrins and TGF-β during fibrotic processes. Tumor epithelial cell/fibroblast co-culture systems were used to mimic the potential interaction of epithelial cells and fibroblasts in tissues undergoing fibrosis. After 7 days of coculture basal level of aSMA were low in lung fibroblast or dermal fibroblast mono-cultures. NCI-H358 and Calu-3 induced aSMA expression the fibroblast layer (FIG. 1). Addition of Abituzumab to NHLF+NCI-H358; NHLF+Calu-3; NHDF+NCI-H358; NHDF+Calu-3 cocultures inhibited induction of aSMA expression in fibroblast.

Abituzumab Blocks Elevated Expression of FMT-Related Genes in H358-Fibroblast Co-Cultures (See Also FIG. 2)

Coculture of NHLF+NCI-H358; NHDF+NCI-H358; induced multiple mRNA transcripts that are markers for FMT and also increased IL-6 production. In this system these markers were reduced by abituzumab treatment, demonstrating that av integrins play a substantial role in FMT.

BIBLIOGRAPHY

Buscemi L, Ramonet D, Klingberg F, Formey A, Smith-Clerc J, Meister J and Hinz B. The Single-Molecule Mechanics of the Latent TGF-β Complex. Current Biology. 2009. 21: 2046-2054

Eberlein C, Rooney C, Ross S J, Farren M, Weir H M, Barry S T. E-Cadherin and EpCAM expression by NSCLC tumour cells associate with normal fibroblast activation through a pathway initiated by integrin αvβ6 and maintained through TGF-β signalling. Oncogene. 2015. 34:704-716.

Eberlein C, Kendrew J, McDaid K, Alfred A, Kang J S, Jacobs V N, Ross S J, Rooney C, Smith N R, Rinkenberger J, Cao A, Churchman A, Marshall J F, Weir H M, Bedian V, Blakey D C, Foltz I N, Barry S T. A human monoclonal antibody 264RAD targeting αvβ6 integrin reduces tumour growth and metastasis, and modulates key biomarkers in vivo. Oncogene. 2013. 32:4406-4416.

Hata S, Okamura K, Hatta M, Ishikawa H, Yamazaki J. Proteolytic and non-proteolytic activation of keratinocyte-derived latent TGF-β1 induces fibroblast differentiation in a wound-healing model using rat skin. J Pharmacol Sci. 2014. 124: 230-243

Mukhopadhyay A, Tan E K, Khoo Y T, Chan S Y, Lim I J, Phan T T. Conditioned medium from keloid keratinocyte/keloid fibroblast coculture induces contraction of fibroblast-populated collagen lattices. Br J Dermatol. 2005. 152:639-645.

Shephard P, Martin G, Smola-Hess S, Brunner G, Krieg T, Smola H. Myofibroblast differentiation is induced in keratinocyte-fibroblast co-cultures and is antagonistically regulated by endogenous transforming growth factor-beta and interleukin-1. Am J Pathol. 2004. 164:2055-2066.

Renzoni E A, Abraham D J, Howat S, Shi-Wen X, Sestini P, Bou-Gharios G, Wells A U, Veeraraghavan S, Nicholson A G, Denton C P, Leask A, Pearson J D, Black C M, Welsh K I, du Bois R M. Gene expression profiling reveals novel TGF-β targets in adult lung fibroblasts. Respir Res. 2004. 5:24.

Lygoe K A, Wall I, Stephens P, Lewis M P. Role of vitronectin and fibronectin receptors in oral mucosal and dermal myofibroblast differentiation. Biol Cell. 2007. 99:601-614

Lygoe K A, Norman J T, Marshall J F, Lewis M P. AlphaV integrins play an important role in myofibroblast differentiation. Wound Repair Regen. 2004. 12:461-470.

Gardner H, Strehlow D, Bradley L, Widom R, Farina A, de Fougerolles A, Peyman J, Koteliansky V, Korn J H. Global expression analysis of the fibroblast transcriptional response to TGF-β. Clin Exp Rheumatol. 2004. 22(Suppl 33):S47-57

Example 2

Effect of Abituzumab on TGF-β Induced FMT in Human Lung Fibroblast

Table of Figures

FIG. 3: TGF-β Increases Integrins Expression in Human Lung Fibroblast

FIG. 4: TGF-β Increases aSMA, IL-6 and other Myofibroblast Marker Gene Expression in Lung Fibroblast FIG. 5: Abituzumab Treatment of Fibroblast Cultures Reduces the TGF-β induced Increase in aSMA and IL-6

FIG. 6: Abituzumab Treatment Reduces TGF-β-induced Collagen Gel Contraction

LIST OF ABBREVIATIONS

αSMA: Alpha Smooth Muscle Actin
BSA: Bovine Serum Albumin
Cy5: Cyanine 5
DAPI: 4',6-Diamidnino-2-Phenylindole
ECM: Extracellular Matrix
FGM: Fibroblast Growth Medium
FMT: Fibroblast to Myofibroblast Transition
FITC: Fluorescence Isothiocyanate
IXM: Image Xpress Micro Screening System
ug: Micgrogram
mg: Milligram
mL: Milliliter
ng: Nanogram
NHDF: Normal Human Dermal Fibroblasts
NHLF: Normal Human Lung Fibroblasts
PBS: Phosphate-Buffered Saline
TGF-β1: Transforming Growth Factor-Beta 1
ELISA Enzyme-Linked Immunosorbent Assay
FBS Fetal Bovine Serum
h Human
IL Interleukin Summary TGF-β1 is shown here to be a potent mediator of fibroblast to myofibroblast transition (FMT) which contributes to increased extracellular matrix deposition and is main driver of fibrotic diseases. Furthermore, there is substantial evidence shown for crosstalk between aV integrins and TGF-β during these processes. TGF-β is secreted in a latent form which contains a Latency Associated Peptide (LAP) region. The LAP of TGF-β1 contains an RGD motif which interacts with the integrins avβ1, avβ3, avβ5, avβ6 and avβ8 resulting in activation of TGF-β1. Abituzumab is a human antibody specific for aV and therefore inhibits avβ1, avβ3, avβ5, avβ6 and avβ8. This study shows and determines the effect of TGF-β on the aV integrin and fibrotic gene expression and that abituzumab can block TGF-β induced gene expression in vitro.

Expression of integrins was analyzed by RT-PCR and it was found that human lung fibroblasts express ITGB1>ITGB5>ITGB8>ITGB3. TGF-β-induced FMT caused increased in the expression of ITGB5 and to a lesser extent ITGB1 and ITGB3. TGF-β treatment increased myofibroblast marker genes in lung fibroblasts and immunofluorescence staining revealed increased in αvβ5 expression. Abituzumab treatment reduced the increased expression of aSMA, production of IL-6 and collagen gel contraction and thus demonstrated an ability to block TGF-β induced FMT.

Introduction

Fibrotic diseases are characterized by excessive scarring due to production, deposition and contraction of extracellular matrix and is believed to be driven by myofibroblast proliferation and activation. Fibrotic diseases represent one of the largest groups of diseases for which there is no effective therapy. The fibrotic processes is regulated by complex set of interactions within a network of profibrotic and antifibrotic mediators. TGF-β signaling is believed to play an important role in fibroblast to myofibroblast transition (FMT) which contributes to increased extracellular matrix deposition and is main driver of disease.

TGF-β isoforms are synthesized as latent precursers complexed with latent TGF-β binding proteins, which contains a Latency Associated Peptide (LAP) region. There is substantial evidence for crosstalk between aV integrins and TGF-β during these processes. The LAP of TGF-β1 contains an RGD motif which interacts with the integrins $\alpha v\beta 1$, $\alpha v\beta 3$, $\alpha v\beta 5$, $\alpha v\beta 6$ and $\alpha v\beta 8$ resulting in activation of TGF-β1. Abituzumab is a pan-αv integrin antibody that binds allosterically to the ligand-binding aV subunit and thus prevents ligand from binding to all αvβ heterodimers and therefore inhibits αv integrin-dependent activation of latent TGF-β and thus blocks acquisition of the myofibroblast phenotype by fibroblasts and other precursors. The present study provided strong evidence of the effect of TGF-β on the aV integrin and fibrotic gene expression and that abituzumab blocks TGF-β induced gene expression in normal human lung fibroblasts (NHLF).

Materials and Methods

Test Systems

The test system is the NHLF from healthy donors stimulated with TGF-β1 with or without Latent TGF-β. Primary NHLF upregulate alpha smooth muscle actin (primary readout) after TGF-β stimulation.

| Description | Company | Cat # | Lot# | Tissue # |
|---|---|---|---|---|
| Normal human lung fibroblasts | Lonza/clonetics | CC-2512 | 0000374386 | 26789 |
| Normal human lung fibroblasts | Lonza/clonetics | CC-2512 | 0000343490 | 25745 |
| Normal human lung fibroblasts | Lonza/clonetics | CC-2512 | 0000369145 | 26646 |

Test Material and Stimulus

| Stimuli/Cytokine | Company | Cat # | Lot# |
|---|---|---|---|
| Recombinant human TGF-β1 | R & D Systems | 240-B-010 | AV5513121 |
| Recombinant human TGF-β1 latent | R & D Systems | 299-LT-005 | FY1914031 |

| Antibodies | Company | Lot/Accession# |
|---|---|---|
| Abituzumab (DI17E6) | EMD Serono | 402499 |
| Anti-HEL IgG2 | EMD Serono | A12-145-2 |

| Antibodies/Dye for staining | Company | Lot # | EMD Serono ID # |
|---|---|---|---|
| αv Integrin antibody | Merck KGaA | 20100224 | EM 013-09 |
| αvB3 Integrin antibody | Merck KGaA | 20091125 | EM 277-03 |
| αvB5 Integrin antibody | Merck KGaA | 20091125 | EM 099-02 |
| αvB6 Integrin antibody | Merck KGaA | 20100224 | EM 052-01 |
| αvB8 Integrin antibody | Merck KGaA | 20100224 | EM 133-09 |

Supplies and Instruments

| Material/Reagent | Provider | Cat. # | Lot # |
|---|---|---|---|
| FGM Fibroblast Growth Medium and Bullet Kit (include Cat#CC-3131 & CC-4126) | Lonza/clonetics | CC-3132 | 354178 |
| Fibroblast Growth Medium | Lonza/clonetics | CC-3131 | 409065 |
| Fibroblast Bullet Kit | Lonza/clonetics | CC-4126 | 417247 |
| Gentamicin-Sulfate | Lonza/clonetics | CC-4081J | 417245 |
| Insulin | Lonza/clonetics | CC-4021J | 417243 |
| rhFGF | Lonza/clonetics | CC-4065J | 417244 |
| FBS | Lonza/clonetics | CC-4101J | 417246 |
| Reagent Pack/Subculture Reagents | Lonza/clonetics | CC-5034 | 409088 |
| Hepes Buffered Saline | Lonza/clonetics | CC-5022 | 362157 |
| Trypsin | Lonza/clonetics | CC-5012 | 372708 |
| Trypsin Neutralizing Solution | Lonza/clonetics | CC-5002 | 385562 |
| T 150 cm2 flasks | Corning | 430825 | 19514018 |
| UltraPure Distilled Water | Invitrogen | 10977-015 | 1607416 |
| PBS | Invitrogen | 20012-027 | 1457916 |
| Collagen 1 Cell ware 96-well Black/Clear Plate | BD Biosciences | 356700 | 2136233 |
| 24 well plates | Falcon | 353047 | N/A |
| Odyssey Blocking Buffer (500 mL) | Li-COR | 927-40000 | T1752 |
| BD Cytofix/Cytoperm Fixation/Permeabilization kit | BD Biosciences | 554714 | 3099684 |
| Fixation Solution | BD Biosciences | 554722 | 3231840 |
| Permeabilization (Perm) Wash Buffer | BD Biosciences | 554723 | 4174605 |
| Anti-actin, smooth muscle, clone ASM-1 | Millipore | CBL171 | 2377949 |
| Goat Anti-mouse IgG Alexa Fluor488: Invitrogen Corp | Invitrogen | A11001 | 1503602 |
| Goat Anti-rabbit IgG Alexa Fluor647: Invitrogen Corp | Invitrogen | A21245 | 1623067 |
| DAPI, dilactate | Sigma Aldrich | D9564-10MG | 042M4005 |
| RNeasy 96 kit | Qiagen | 74181 | 148019008 |
| RT2 First Strand kit | Qiagen | 330401 | N/A |
| RT2 Profiler PCR Array (Custom) | Qiagen | 12473 | N/A |
| Cell Contraction assay kit | Cell BioLabs, Inc | CBA-201 | N/A |

| Equipment: | Company | Serial # |
| --- | --- | --- |
| Allegra X-14R Centrifuge | Beckman Coulter | B34604-AA |
| Laminar hood model 1395, 1300 SeriesA2 | Thermo Fisher | 114627-128 |
| Incubator at 37 C. with humidified 5% CO2 | Thermo Fisher | 313910-5441 |
| Spectramax M5e | Molecular Devices | MVE06101 |
| Biotek 405LS microplate washer | Perkin Elmer | 1306126 |
| Microscope, Nikon TMS | DSC Optical Services | 11345 |
| Water Bath | Equipnet | 35933-2-2 |
| Image Xpress Micro Imaging Microscope | Molecular Devices | 12264 |
| Optiplex 990 Image Analysis Computer | Dell | X16-96076 |
| QuantStudio 12K Flex | Applied Biosystems by Life Technologies | 285880466 |

Design
Outline Study Design

NHLF culture media (FGM with 2% FBS): FGM™-2 BulletKit™ (CC-3132) contains one 500 ml bottle of Fibroblast Cell Basal Medium (CC-3131) and Fibroblast Bullet Kit (CC-4126) with the following growth supplements: 0.5 ml hFGF-B (CC-4065J); 0.5 ml Insulin (CC-4021J); 10 ml FBS (CC-4101J); 0.5 ml GA-1000 (CC-4081J).

NHLF culture media for FMT assays (FGM with 0.1% FBS): FGM™-2 BulletKit™ (CC-3132) contains one 500 ml bottle of Fibroblast Cell Basal Medium (CC-3131) and Fibroblast Bullet Kit (CC-4126) with the following growth supplements: 0.5 ml hFGF-B (CC-4065J); 0.5 ml Insulin (CC-4021J), 0.5 ml FBS (CC-4101J), 0.5 ml GA-1000 (CC-4081J).

NHLF were grown in T150 tissue culture flasks in FGM with 2% FBS until they were 70-80% confluent on the day of the assay. The cells were rinsed with 6 ml HEPES buffered saline solution (Lonza Cat #CC-5022), trypsinized with 6 ml trypsin/EDTA (Lonza Cat #CC-5012) for 5 min at room temperature. The trypsin was inactivated with 6 ml trypsin neutralizing solution (Lonza Cat #CC-5002), spun down at 400 g for 4 min and washed once with FGM with 2% FBS. For imaging studies, cells were seeded at 7500 cells/well in Collagen 1 Cellware 96-well Black/Clear Plate. For gene expression studies, cells were seeded at 50,000 cells/well in 24 wells culture plates. Cells were cultured for 8 hours in FGM with 2% FBS. Media were aspirated and cells were starved overnight in FGM containing 0.1% FBS.

To investigate the effect of TGF-β on the aV integrins, aSMA and gene expression: Media were aspirated and 100 ul of FGM containing 0.1% FBS were added, TGF-β were added at 2× (20 ng/ml) of desired concentration in 100 ul of FGM containing 0.1% FBS. 72 hours later, media were collected and stored at −80 C for IL-6 detection.

To investigate the effect of Abituzumab on TGF-β induced fibroblast myofibroblast transition (FMT), NHLF were seeded at 7500 cells/well in Collagen 1 Cellware 96-well Black/Clear Plate, cultured for 8 hours in FGM with 2% FBS. Media were aspirated and cells were starved overnight in FGM containing 0.1% FBS. Media were aspirated and 100 ul of FGM with 0.1% FBS containing abituzumab or anti-HEL IgG at a conc of 25 ng/ml were added and incubated for 30 min. TGF-β were added at 2× (Latent TGF-β1=40 ng/ml, TGF-β=0.312 ng/ml) of desired concentration in 100 ul of FGM containing 0.1% FBS. 72 hours later, media were collected and stored at −80 C for IL-6 detection.

For aV integrins, aSMA expression studies using immunofluorescence, cells were fixed and stained according to the alpha smooth muscle actin (αSMA) and aV Integrin staining procedure. For FMT related gene expression analysis, cells were stored at −80 C until ready for RNA isolation and RT-PCR.

Alpha smooth muscle actin and aV Integrins immunofluorescence staining: Cells were washed 2 times with PBS (200 ul in 96 well plates), and then fixed with Fixation/Permeabilization Solution for 45 mins at room temperature (50 uL in 96 well plate). Cell were then washed 3 times with 5 min incubation using 1×BD perm wash buffer (diluted in distilled water at 1:10 dilution). The cells were blocked with Odyssey block buffer (50 ul in 96 well plates) for 60 min at room temperature. The plates were washed 2 times with 5 min incubation between each wash using 1×BD perm wash buffer (200 ul in 96 well plates). Anti-SMA antibody were added at 1:100 dilution in wash buffer. Anti-Integrin Ab were used at 1 ug/ml in perm buffer as final concentration and incubated for 3 h at room temperature. Plates were then washed 2 times with 1×BD perm wash buffer (200 ul in 96 well plate). Secondary Ab Goat Anti-mouse IgG conjugated with Alexa Fluor 488 were used at 1:200 dilution and Secondary Ab Goat Anti-rabbit IgG conjugated with Alexa Fluor 647 were used at 1:100 dilution in perm wash buffer in a final volume of 100 ul and incubated for 1 h at room temperature. Cells were washed 2 times using 200 ul 1×BD perm wash buffer with 5 minutes incubation between each washes. DAPI were added to wash buffer at 1:1000 dilution and 200 ul were added to the plated, incubated for 5 min at room temperature, solution were aspirated and replaced with 200 ul of 1×BD perm wash buffer.

For gene expression analysis. RNA were extracted according to the "RNeasy 96 Protocol for Isolation of Cytoplasmic RNA from Animal Cells-using Vaccum Technology" included in the RNeasy 96 Kit (Qiagen). cDNA Synthesis was done using the RT2 First Strand Kit and Real-Time PCR for RT2 profiler PCR arrays with cycling conditions for Applied Biosystems cyclers according to the procedures described in the RT2 Profiler PCR Array Handbook (Qiagen).

For gel contraction assay: Human Fibroblasts grown in T150 were rinsed once with HEPES and supernatants were removed and 6 ml of trypsin were added to each flask for 5 min at room temperature, 6 ml of trypsin neutralizing solution were added and cells were collected by centrifugation at 400 g. Cells were resuspended in FGM with 2% FBS and at 2×106 cells/ml. Cells were treated with 10 ug/ml Abituzumab or anti-HELIgG for 15 mins. Collagen lattice were formed by mixing 2 parts (120 ul) of 'treated' cell suspension and 8 parts (480 ul) of cold collagen gel solution with or without TGF-β (10 ng/ml). 500 ul of the cell-collagen mixture were transferred to each well in a 24 well plate, incubate 1 h at 37 C. After collagen polymerization, 1 ml of culture medium was added on top of each collagen gel lattice. Collagen gel is gently lifted up using a sterile spatula, the gel is allowed to float in the media. Collagen gel size was monitored for 5 days and pictures were taken on day 5.

Read-Outs
Plate Reading Procedure for Imaging

Image Xpress Micro (IXM) machine and the MetaXpress software program were used for image acquisition and analysis. For 3 color staining: DAPI, FITC, and Cy5, plate acquisition imaging protocol: "2014-YW-SMA-Int-DAPI-647-10x" were used. For 2 color staining: DAPI and FITC staining, plate acquisition imaging protocol: "2014-YW-SMA488-DAPI-10x" were used. For data analysis, multi wavelength cell scoring analysis parameter protocol "2014-5-7-YW-SMA488-DAPI-4x-2 para a" were used to quantify the amount of SMA fiber induction due to FMT. Images of individual well were downloaded as BMP files.

IL-6 ELISA

Levels of human IL-6 were determined using a commercial IL-6 ELISA assay (Human Duoset IL-6, R & D Systems) following the manufacturer's instructions. Optical density reading (OD) at 450 nm are performed using Spectramax M5e reader (Molecular Devices) and IL-6 concentration for each sample extrapolated from a four-parameter logistic curve fit calculated using OD reading from the internal IL-6 standard.

Gene Expression Analysis

After RT-PCR has completed the run in the QuantStudio 12k flex Applied Biosystem cycler, CT values for all wells were downloaded to Excel spreadsheet for calculation of relative expression.

Computer Programs Used

| Program | Version | Supplier |
| --- | --- | --- |
| Microsoft Office | 2007/2013 | Microsoft |
| GraphPad Prism | 5.02 | GraphPad |
| QuantStudio 12k flex Real time PCR system | 1.2.2 | Applied Biosystem |
| MetaXpress Image Analysis Software | 3.1.0.97 | Molecular Devices |
| Adobe Photoshop C56 | 13.0 X32 | Adobe |

Relative Gene Expression (Basal Level) and Fold Change Calculations $C_T$ Threshold cycle. The $C_T$ is the cycle number at which the fluorescence generated within a reaction crosses the threshold line. $C_T$ values are logarithmic and are used either directly for quantitative analyses.

For Relative Gene Expression (Basal Level):

Calculate the $\Delta C_T$ value. $\Delta C_T = C_{T\ target} - C_{T\ reference(GAPDH)}$ Calculate the $2^{-\Delta C_T}$ as relative gene expression at basal level.

For Relative Gene Expression (Fold Change after Treatment):

Calculate the $\Delta C_T$ value. $\Delta C_T = C_{T\ target} - C_{T\ reference(GAPDH)}$ Calculate the $\Delta\Delta C_T$ value. $\Delta\Delta C_T = \Delta C_T$ test sample(treatment) $- \Delta C_T$ calibrator sample(without treatment)

The amount of target, normalized to an endogenous reference (e.g. GAPDH) and relative to a calibrator (before treatment or control), is given by: $2^{-\Delta\Delta C_T}$ Results TGF-β Increases Integrins Expression in Human Lung Fibroblast (See Also FIG. 3)

Expression of integrins in NHLF were analyzed by RT-PCR and it was found that NHLFs express integrins at steady state and expression level in the order ITGB1>ITGB5>ITGAV>ITGB8>ITGB3. It has been hypothesized that there is crosstalk between aV integrins and TGF-β, therefore, we looked at the effect of TGF-β in Integrins expression in FMT assays. We found that TGF-β-induced FMT caused increased in the expression of ITGB5 and to a lesser extent ITGB1 and ITGB3 Immunofluorescence staining revealed increased in αvβ5 expression (see FIG. 3: TGF-β Increases Integrins Expression in Human Lung Fibroblast)

TGF-β Increases aSMA, IL-6 and Other Myofibroblast Marker Gene Expression in Lung Fibroblast (See Also FIG. 4)

TGF-β treatment increased IL6 production and alpha smooth muscle expression as detected by immunofluorescence and RT-PCR. TGF-β treatment increased myofibroblast marker gene such as alpha smooth muscle, collagen, fibronectin, SERPINE1, SNAI1, periostin, N-Caherin expression in lung fibroblasts (see FIG. 4: TGF-β Increases aSMA, IL-6 and other Myofibroblast Marker Gene Expression in Lung Fibroblast).

Abituzumab Treatment of Fibroblast Cultures Reduces the TGF-β-Induced Increase in aSMA and IL-6 (See Also FIG. 5)

As shown in FIG. 1, TGF-β increase expression of Integrins, in this experiments we treated NHLF with sub-optimal dose of active TGF-β to increase expression of integrin together with high dose of Latent form TGF-β. Combination of Latent and active TGF-β1 induced higher number of cells that expressed aSMA compared to Latent or active form alone. Abituzumab treatment reduced the expression of aSMA, production of IL-6 and FMT gene expression caused by TGF-β activation (see FIG. 5: Abituzumab Treatment of Fibroblast Cultures Reduces the TGF-β-induced Increase in aSMA and IL-6).

Abituzumab Treatment Reduces TGF-β-Induced Collagen Gel Contraction (See Also FIG. 6)

3 dimensional collagen gel assays were used in fibroblast contraction studies. To determine whether the changes in aSMA protein by TGF-β1 and blockade of aV integrins but Abituzumab had a functional consequence, collagen gel contraction assays were performed. When Abituzumab was added to the cells, it reduced the degree of contraction caused by the addition of TGF-β (see FIG. 6: Abituzumab Treatment Reduces TGF-β-induced Collagen Gel Contraction).

Discussion

In this report, we showed that TGF-β increases aV integrins, aSMA, and other FMT genes such as collagen, fibronectin, SERPINE1, SNAI1, periostin, N-Caherin expression in human lung fibroblast. Abituzumab treatment of fibroblast cultures reduces the TGF-β-induced increases in aSMA, IL6, CTGF, SERPINE, PLOD.

Abituzumab is been shown to block αv integrin-dependent activation of latent TGF-β at sites of extracellular matrix overproduction. Here we showed, using in vitro culture systems, abituzumab blocks fibroblast myofibroblast transition. TGF-β upregulates aV integrins, blocking αv Integrin-dependent activation of latent TGF-β, blocks local upregulation of integrins on myofibroblast cell membranes, and thus is able to break the vicious cycle of TGF-β activation and myofibroblast accumulation.

LITERATURE

Buscemi L, Ramonet D, Klingberg F, Formey A, Smith-Clerc J, Meister J and Hinz B. The Single-Molecule Mechanics of the Latent TGF-β Complex. Current Biology. 2009. 21: 2046-2054

Goodman S L, Grote H J, Wilm C. Matched rabbit monoclonal antibodies against αv-series integrins reveal a novel αvβ3-LIBS epitope, and permit routine staining of archival paraffin samples of human tumors. Biol Open. 2012. 1(4):329-340.

Scaffidi A K, Petrovic N, Moodley Y P, Fogel-Petrovic M, Kroeger K M, Seeber R M, Eidne K A, Thompson P J, Knight D A. alpha(v)beta(3) Integrin interacts with the transforming growth factor beta (TGF-β) type II receptor to potentiate the proliferative effects of TGF-β1 in living human lung fibroblasts. J Biol Chem. 2004. 279(36): 37726-37733

Renzoni E A, Abraham D J, Howat S, Shi-Wen X, Sestini P, Bou-Gharios G, Wells A U, Veeraraghavan S, Nicholson A G, Denton C P, Leask A, Pearson J D, Black C M, Welsh K I, du Bois R M. Gene expression profiling reveals novel TGF-β targets in adult lung fibroblasts. Respir Res. 2004. 5:24.

Lygoe K A, Wall I, Stephens P, Lewis M P. Role of vitronectin and fibronectin receptors in oral mucosal and dermal myofibroblast differentiation. Biol Cell. 2007. 99(11):601-614

Lygoe K A, Norman J T, Marshall J F, Lewis M P. AlphaV integrins play an important role in myofibroblast differentiation. Wound Repair Regen. 2004. 12(4):461-470.

Gardner H, Strehlow D, Bradley L, Widom R, Farina A, de Fougerolles A, Peyman J, Koteliansky V, Korn J H. Global expression analysis of the fibroblast transcriptional response to TGF-β. Clin Exp Rheumatol. 2004. 22(Suppl 33):S47-57

Appendix

Gene List for RT-PCR

| Gene Symbol | Alias | Refseq # | Official Full Name | RT2 Catalog Number |
|---|---|---|---|---|
| ITGAV | CD51/MSK8/VNRA/VTNR | NM_002210 | Integrin, alpha V (vitronectin receptor, alpha polypeptide, antigen CD51) | PPH00628 |
| ITGB1 | CD29/FNRB/GPIIA/MDF2/MSK12/VLA-BETA/VLAB | NM_002211 | Integrin, beta 1 (fibronectin receptor, beta polypeptide, antigen CD29 includes MDF2, MSK12) | PPH00650 |
| ITGB3 | BDPLT16/BDPLT2/CD61/GP3A/GPIIIa/GT | NM_000212 | Integrin, beta 3 (platelet glycoprotein IIIa, antigen CD61) | PPH00178 |
| ITGB5 | — | NM_002213 | Integrin, beta 5 | PPH00634 |
| ITGB6 | — | NM_000888 | Integrin, beta 6 | PPH00630 |
| ITGB8 | — | NM_002214 | Integrin, beta 8 | PPH00647 |
| POSTN | OSF-2/OSF2/PDLPOSTN/PN/periostin | NM_006475 | Periostin, osteoblast specific factor | PPH12343 |
| TNC | 150-225/DFNA56/GMEM/GP/HXB/JI/TN/TN-C | NM_002160 | Tenascin C | PPH02442 |
| VTN | V75/VN/VNT | NM_000638 | Vitronectin | PPH00253 |
| CDH1 | Arc-1/CD324/CDHE/ECAD/LCAM/UVO | NM_004360 | Cadherin 1, type 1, E-cadherin (epithelial) | PPH00135 |
| CDH2 | CD325/CDHN/CDw325/NCAD | NM_001792 | Cadherin 2, type 1, N-cadherin (neuronal) | PPH00636 |
| CLDN1 | CLD1/ILVASC/SEMP1 | NM_021101 | Claudin 1 | PPH02779 |
| OCLN | BLCPMG | NM_002538 | Occludin | PPH02571 |
| TJP1 | ZO-1 | NM_175610 | Tight junction protein 1 (zona occludens 1) | PPH09919 |
| VIM | CTRCT30/HEL113 | NM_000338 | Vimentin | PPH00417 |
| KRT5 | CK5/DDD/DDD1/EBS2/K5/KRT5A | NM_000424 | Keratin 5 | PPH02625 |
| CTNNB1 | CTNNB/MRD19/armadillo | NM_001904 | Catenin (cadherin-associated protein), beta 1, 88 kDa | PPH00643 |
| ACTA2 | AAT6/ACTSA/MYMY5 | NM_001613 | Actin, alpha 2, smooth muscle, aorta | PPH01300 |
| COL1A1 | OI4 | NM_000088 | Collagen, type I, alpha 1 | PPH01299 |
| COL1A2 | OI4 | NM_000089 | Collagen, type I, alpha 2 | PPH01918 |
| FN1 | CIG/ED-B/FINC/FN/FNZ/GFND/GFND2/LETS/MSF | NM_002026 | Fibronectin 1 | PPH00143 |
| KLF4 | EZF/GKLF | NM_004235 | Kruppel-like factor 4 (gut) | PPH18388 |
| ZEB1 | AREB6/BZP/DELTAEF1/FECD6/NIL2A/PPCD3/TCF8/ZFHEP/ZFHX1A | NM_030751 | Zinc finger E-box binding homeobox 1 | PPH01922 |

| Gene Symbol | Alias | Refseq # | Official Full Name |
|---|---|---|---|
| CCL2 | GDCF-2/HC11/HSMCR30/MCAF/MCP-1/MCP1/SCYA2/SMC-CF | NM_002982 | Chemokine (C-C motif) ligand 2 |
| CCL3 | G0S19-1/LD78ALPHA/MIP-1-alpha/MIP1A/SCYA3 | NM_002983 | Chemokine (C-C motif) ligand 3 |
| SERPINE1 | PAI/PAI-1/PAI1/PLANH1 | NM_000602 | Serpin peptidase inhibitor, clade E (nexin, plasminogen activator inhibitor type 1), member 1 |
| SNAI1 | SLUGH2/SNA/SNAH/SNAIL/SNAIL1/dJ710H13.1 | NM_005985 | Snail homolog 1 (*Drosophila*) |
| ACTB | BRWS1/PS1TP5BP1 | NM_001101 | Actin, beta |
| GAPDH | G3PD/GAPD | NM_002046 | Glyceraldehyde-3-phosphate dehydrogenase |
| HGDC | HIGX1A | SA_00105 | Human Genomic DNA Contamination |
| RTC | RTC | SA_00104 | Reverse Transcription Control |
| PPC | PPC | SA_00103 | Positive PCR Control |
| PLOD2 | LH2/TLH | NM_182943 | Procollagen-lysine, 2-oxoglutarate 5-dioxygenase 2 |
| CTGF | CCN2/HCS24/IGFBP8/NOV2 | NM_001901 | Connective tissue growth factor |

Example 3

Effect of Abituzumab on Binding of αvβ6 to Latency-Associated Peptide (LAP)

LIST OF ABBREVIATIONS

αSMA: Alpha Smooth Muscle Actin
ECM: Extracellular Matrix
ug: Microgram
mg: Milligram
mL: Millilitre
LAP: latency associated peptide (LAP)
LTBP: latent TGF-β binding protein
ng: Nanogram
TGF-β1: Transforming Growth Factor-Beta 1
ELISA: Enzyme-Linked Immunosorbent Assay
h: Human
IL: Interleukin Summary αvβ3, αvβ3, αvβ6 and αvβ8 can Control the Activation of TGF-β

TGF-β1 is a major pro-fibrotic cytokine that plays an important part in the development of tissue fibrosis in various organs. TGF-β1 contributes to fibrosis by promoting the differentiation of tissue fibroblasts into myofibroblasts. Myofibroblasts can produce extracellular matrix (ECM) proteins, and are the main drivers for ECM expansion and contraction during fibrosis. TGF-β1 is secreted in a latent complex, which in addition to TGF-β1, also contains a latency associated peptide (LAP) and latent TGF-β binding protein (LTBP). The complex can adopt an open conformation to release active TGF-β1 when LTBP is anchored to ECM and LAP binds one of the αv integrins, namely αvβ1, αvβ3, αvβ5, αvβ6 and αvβ8, on the αv subunit.

Abituzumab is a human antibody specific for the ligand-binding αv subunit of av integrins. Upon binding to the αv subunit, abituzumab can prevent αv integrins from binding to its ligands such as LAP. The goal of this study was to evaluate the ability of abituzumab to block binding of LAP to αvβ6.

Using an anti-αvβ6-based ELISA assay, we demonstrated that abituzumab was able to block the binding of αvβ6 to LAP precoated to ELISA plates in a dose-dependent manner. The finding clearly demonstrate the ability of abituzumab to block binding of αv integrins to LAP, a key step in the activation of TGF-β. This forms part of the scientific basis for developing abituzumab for treating fibrotic diseases.

Introduction

TGF-β1, a major pro-fibrotic cytokine, plays an important part in the development of tissue fibrosis in various organs. TGF-β1 contributes to fibrosis by promoting the differentiation of tissue fibroblasts into myofibroblasts. Myofibroblasts can produce extracellular matrix (ECM) proteins and contract. They are the main drivers for ECM expansion and contraction during fibrosis. TGF-β1 is secreted in a latent complex which in addition to TGF-β1, also contains a latency associated peptide (LAP) and latent TGF-β binding protein (LTBP). The complex can adopt an open conformation to release active TGF-β1 when LTBP is anchored to ECM and LAP binds one of the αv integrins, namely αvβ1, αvβ3, αvβ5, αvβ6 and αvβ8, on the αv subunit.

The purpose of the present study was to evaluate the ability of abituzumab to block binding of LAP to αvβ6.

Materials and Methods

Materials

Test Systems

The test system is a competitive binding assay in which a plate is coated with recombinant human LAP and then incubated with recombinant human αvβ6 in the presence or absence of abituzumab also termed DI17E6. The amount of αvβ6 bound to LAP is detected by ELISA using a rabbit anti αvβ6 antibody (capture antibody) and a goat anti-rabbit IgG (detecting antibody) conjugated with horse radish paraoxide (HRP).

Materials and Instruments
Key Materials

| Abbreviated name | Origin | Catalog/internal code # | Lot # |
|---|---|---|---|
| αvβ6 integrin | In house | 262Y08S1.INT | Pool B |
| DI17E6 | In house | EMD 525797 | 40350 |
| DI17E6 | In house | EMD 525797 | 13245 |
| LAP | R&D Systems | 246-LP-025/CP | IK2613061 |
| 17E6 | In house | 265Y08C2.G01 | 265Y08C2.G01/Pool A |
| anti-αvβ6 antibody | in house | MSB0011521H | 1 |
| Anti-HEL IgG | in house | MSB0011523H | 1 |
| 425(VL)/17E6(VH)g1 hinge IgG2 (FN->AQ) | In house | NA | A-10-118-2 |
| anti-αvβ6 antibody 10D5 | Millipore | Mab2077Z | 2430505 |
| anti-αvβ6 antibody LM609 | In house | NA | EMD84266'-02 |
| Rabbit anti-αvβ6 | In house | NA | EMD05201-1:#1/b:#1 |
| Goat anti-rabbit IgG | Biorad | 172-1019 | LS1/21019 |
| ELISA plates | Greiner | 07230103 | NA |

Key Equipment

| Equipment: | Company | EMD Serono ID # | Serial # |
|---|---|---|---|
| ELISA plate reader | Tecan ELISA Reader InfiniteM200 | 70160370 | 911007538 |

For other materials and equipment, see report SWE00174.

Coating Buffer (in Double Distilled Water):
200 mM Tris
150 mM NaCl
Adjust pH to 7.4 with HCl
+1 mM CaCl2; 1 mM MgCl2; 0.01 mM MnCl2
Blocking Buffer (in Double Distilled Water):
50 mM Tris
100 mM NaCl
Adjust pH to 7.4 with HCl
+5 mg/ml BSA
Wash and Dilution Buffer (in Double Distilled Water):
200 mM Tris
150 mM NaCl
Adjust pH to 7.4 with HCl
+1 mM CaCl2; 1 mM MgCl2; 0.01 mM MnCl2
+0.1 mg/kg BSA
Experimental Design
Outline Study Design
Coating of Plates with LAP.

Recombinant human LAP was added to a plate at a final concentration of 0.1 µg/ml and incubated overnight at 4° C. for coating the plate with LAP. The plate was then drained and incubated with 100 µl of blocking buffer for 2 hours at 37° C. to block non-specific binding of αvβ6 to the plates.
Addition αvβ6 and Abituzumab or Control Antibodies to LAP Coated Plates.

50 µl of pre-diluted abituzumab or control antibodies were added to each well from high to low concentrations in a serial dilution. Then 50 µl the αvβ6 solution was added to each well. The final concentrations for the antibodies were 2.5 µg/ml-0.16 ng/ml, and 0.25 µg/ml for αvβ6.

The effect of abituzumab was compared with two other anti-αvβ6 antibodies: MSB0011521H-1 and 10D5. IgG2a was used as isotype control IgG for abituzumab. Anti-HEL (MSB0011523H-1) is an antibody specific for the non-mammalian protein Hevein-like preproprotein from *Arabidopsis*, and was used as a negative control antibody for MSB0011521H-1. 17E6 is the original non-deimmunized mouse pan anti-αv antibody from which abituzumab or DI17E6 was derived. These antibodies were added at the same concentrations as abituzumab or DI17E6.

The plate was incubated for 60 min at 37° C. with αvβ6, and abituzumab or its control antibodies. The plates were then washed for addition of secondary antibodies.
Addition HRP-Conjugated Goat Anti-Rabbit IgG to Plates, Color Development and Reading.

The plate was added HRP-conjugated goat anti-rabbit IgG and incubated for 90 min at 37° C. The plate was then added R&D substrate reagent (Pack DY999) and incubated for 20 min to develop the color before the reaction was stopped with the addition of R&D stop solution DY994. The plate was then read at 450 nm on the Tecan ELISA Reader InfiniteM200.
Read-Outs
Binding of αvβ6 to LAP Measured by Using ELISA.

The amount of αvβ6 bound to LAP was determined by using the procedures described above in Study Design.
Results
Abituzumab Inhibits Binding of αvβ6 to LAP (See Also FIG. 7)

Binding of αvβ6 to precoated LAP was detected by a specific anti αvβ6 antibody-based ELISA. The binding was blocked in a concentration-dependent manner by DI17E6 when it was co-incubated with αvβ6 in a plate precoated with LAP. The anti-αvβ6 antibodies MSB0011521H-1 and 10D5 also inhibited the binding. In contrast, neither the isotype control IgG2 nor the negative control antibody (anti-HEL, MSB0011523H-1) displayed any inhibitory effects. Also the αvβ3 integrin specific inhibitory antibody LM609 did not inhibit αvβ6 binding to LAP. The findings indicate that DI17E6 specifically inhibit the binding of αvβ6 to LAP.
Binding of αvβ6 to LAP Measured by Using ELISA.

The amount of αvβ6 bound to LAP was determined by using the procedures described above in Study Design.
Results
Abituzumab Inhibits Binding of αvβ6 to LAP Binding of αvβ6 to precoated LAP was detected by a specific anti αvβ6 antibody-based ELISA. The binding was blocked in a concentration-dependent manner by DI17E6 when it was co-incubated with αvβ6 in a plate precoated with LAP. The anti-αvβ6 antibodies MSB0011521H-1 and 10D5 also inhibited the binding. In contrast, neither the isotype control IgG2 nor the negative control antibody (anti-HEL, MSB0011523H-1) displayed any inhibitory effects. Also the αvβ3 integrin specific inhibitory antibody LM609 did not inhibit αvβ6 binding to LAP. The findings indicate that DI17E6 specifically inhibit the binding of αvβ6 to LAP.

Tabulated Study Report

| | |
|---|---|
| Title of study: | Effect of abituzumab on Binding of αvβ6 to Latency-Associated Peptide (LAP) |
| Principle of test: | Competitive binding ELISA assay |
| Biological materials | αvβ6 |
| Experimental conditions/treatment schedule: | Binding of αvβ6 to pre-coated LAP/co-incubation of αvβ6 and abituzumab for competitive inhibition |
| Test Article: | Abituzumab |
| Treatment of controls: | Anti-HEL (MSB0011523H-1, negative control), IgG2a (isotype control) |
| Method of evaluation/Endpoints: | Precentage of αvβ6 binding to LAP detected by αvβ6 ELISA, with blank (no αvβ6) as 0% and αvβ6 alone as 100%. |
| Results: | Abituzumab inhibited αvβ6 binding to LAP in a concentration-dependent manner. |
| Conclusions: | Abituzumab specifically inhibits αvβ6 binding to LAP in a concentration dependant manner |

Discussion

In this study, we showed that abituzumab (DI17E6) specifically and concentration-dependently inhibited αvβ6 binding to LAP. The finding clearly demonstrate the ability of abituzumab to block binding of αv integrins to LAP, a key step in the activation of TGF-β. This evidence forms an important part of the scientific basis for using abituzumab for treating fibrosis and/or fibrotic diseases (see also FIG. 7: FIG. 7 shows the inhibition of αvβ6 binding to LAP by Abituzumab). Binding of αvβ6 to coated LAP was detected as an increase in the optical density in wells containing αvβ6 (untreated) over the blank (buffer with no αvβ6). The values were normalized with the former as a 100% and the latter as 0%. Both batches of DI17E6 (batch #40350 and 13245) reduced the binding of αvβ6 to LAP in a concentration-dependent manner, similarly to the anti-αvβ6 antibody MSB0011521H-1, but better than anti-αvβ6 antibody 10D5. In contrast, neither the isotype control IgG (IgG2) nor the negative control antibody (anti-HEL, MSB0011523H-1, data not shown) affected the binding at the same concentrations range. Also the αvβ3 specific inhibitory antibody LM609 did not inhibit αvβ6 binding to LAP.

Example 4

Fibrosis/Systemic Sclerosis Gene Signature
Summary

The goal of this study was to find a robust gene signature for diagnosing & monitoring the status of fibrosis in patients with systemic sclerosis (SSc).

Genes for the signature were identified using a dual strategy:

A list of literature-based genes was pre-defined and tested for up-regulation in SSc skin in published microarray-based gene expression data.

In an unbiased analysis of all genes, three public SSc data sets were used to find candidate genes up-regulated in SSc skin.

Further, the pre-final candidate gene list was filtered on two public genome-scale gene expression data sets for their association with pulmonary fibrosis.

Finally, the list of candidate genes was filtered for up-regulation in immune-related tissues compared to solid tissues.

In summary, we were able to find a robust signature of 19 non-immune-related genes up-regulated in SSc and pulmonary fibrotic tissue by analyzing five appropriate data sets.

In an experiment with human fibroblasts that were either supplemented with TGF-β or co-cultured with cells from the human epithelial H358 lung cell line a gene to be included in the TGF-β-up/Abituzumab-down signature (in the following termed TUAD signature) had to show an up-regulation after administration of TGF-β (median fold change across 3 repeated experiments).

Further, the final TUAD signature of 9 genes was subjected to an experiment with normal human lung fibroblast (NHFL) that were co-cultured with human H358 cells and treated either with anti-HEL (hen egg lysozyme) or abituzumab at two doses. The TUAD was to be accepted as TGF-β linked fibrosis signature that can be down-modulated by Abituzumab, because a) of a down-regulation of all genes in the 9-gene signature after Abituzumab treatment, and b) because of the down-regulation of the net TUAD 9-gene signature score.

Introduction

This study aims to was to find a robust gene signature for monitoring of fibrosis in patients with systemic sclerosis (SSc) using a two-tier process. Literature-based genes reported to be up-regulated in SSc and TGF-simulated fibroblasts as well as genes with strong evidence of up-regulation in patients with SSc/fibrosis in public data sets were to be subjected to further analysis to finally yield a robust gene signature for fibrosis in SSc and IPF.

In addition, we performed nanostring expression profiling experiments to identify another signature, termed TUAD signature, of genes that are up-regulated by TGF-β, thus representing a TGF-β dependent gene subgroup of the 19 gene signature. Finally, we subjected this TUAD signature to another experiment to test whether Abituzumab can down-regulate the TUAD signature.

Materials

For the assessment of up-regulated genes in SSc/fibrosis we use the following data sets. Data sets are available in the Gene Expression Omnibus (GEO) data base.

Gene expression is obtained by averaging probe set intensities per gene.

Systemic Sclerosis Data Sets

GSE9285 (Milano et al., 2008) contains 75 samples in total. Skin biopsies were taken from the forearm and back of 17 patients with diffuse SSc (dSSc), 7 with limited SSc (lSSc), 3 patients with morphea and 6 healthy controls.

Data set GSE32413 (Pendergrass et al., 2012) consists of 89 skin biopsy samples in total. Gene expression was measured of 22 patients with SSc and 9 healthy controls. 13 of the SSc patients were treated with rituximab, 9 were untreated. We use the baseline/pre-treatment samples for the assessment of differential expression between SSc skin and normal skin and exclude the biopsies taken 6 and 36 months after treatment.

GSE45485 (Hincliff et al., 2013) contains 83 skin biopsies in total from 12 SSc patients treated with mycophenolate motefil (MMF) and 10 healthy controls. Only baseline (pre-treatment) samples from SSc patients were included in the analysis, samples taken 6 and 12 months after MMF treatment were excluded.

Pulmonary Fibrosis Data Sets

GSE24206 (Meltzer et al., 2011) 17 lung samples from 11 patients with early/advanced Idiopathic Pulmonary Fibrosis (IPF). 6 patients provided a pair of samples from upper and lower lobes, 5 patients contributed singleton samples). 6 control specimens were obtained from routine lung volume reduction of healthy donor lungs at the time of lung transplantation.

Data set GSE48149 (unpublished) contains 53 lung samples in total. 8 patients with Idiopathic Pulmonary Arterial Hypertension (IPAH), 13 patients with IPF, 10 patients with Pulmonary Arterial Hypertension due to SSc (SSc-PAH) and 13 patients with Pulmonary Fibrosis due to SSc (SSc-PF) are included as well as 9 healthy controls. GSE21369 comprises 29 lung tissue samples of 23 subjects. Data of 11 patients diagnosed with Usual Interstitial Pneumonia/Idiopathic Pulmonary Fibrosis (UIP/IPF) and 6 controls were used, samples of patients with non-specific interstitial pneumonia were excluded.

Immune-Related Data Set

Gene expression of 28 immune-related tissues and 118 non-immune/non-cancer tissues included in data set GSE1133 (Su et al., 2004) were used in this study.

Validation Data Sets

Data set GSE22459 (Park et al., 2010) contains 65 renal transplant recipients with signs of fibrosis and inflammation on 1-year protocol biopsy.

Data set GSE61260 (Hovarth et al., 2014) contains 134 Nash (Non-alcoholic fatty liver disease), PSC (Primary sclerosing cholangitis), PBC (primary biliary cholangitis), NAFLD (Non-alcoholic fatty liver disease), heathy obese and normal liver samples.

Data set GSE48452 (Ahrens et al., 2013) contains 73 samples from Nash (Non-alcoholic fatty liver disease), steatosis, heathy obese and normal liver.

Data set GSE49541 (Moylan et al., 2014) contains 72 patients with NAFLD (40 with mild NAFLD, fibrosis stage 0-1 and 32 with advanced NAFLD, fibrosis stage 3-4).

Data set GSE39491 (Hyland et al., 2014) contains 120 samples of Barrett's metaplasia and matched normal mucosa from squamous esophagus (NE) and gastric cardia (NC) in 43 BE patients.

Data set GSE26886 (Wang et al., 2013) contains 20 specimens of Barrett's esophagus patients, 21 specimens of adenocarcinoma patients and 19 biopsies from patients with normal esophageal squamous epithelium, 9 specimens of squamous cell carcinoma.

Data set GSE37200 (Silvers et al., 2010) contains 31 Barrett's esophagus and 15 adenocarcinoma samples.

Data set GSE47460 (unpublished) contains 582 subjects in total, 254 have interstitial lung disease, 220 have COPD, and 108 are controls.

Data set GSE24988 (Mura et al., 2012) contains 116 samples from the recipients organs of PF patients undergoing lung transplantation.

Data set GSE17978 (Emblom-Callahan et al., 2010) contains 58 samples from 12 lungs of patients with end-stage idiopathic pulmonary fibrosis and 6 donors of normal lungs (controls).

Data set GSE53845 (DePianto et al., 2015) contains samples from 40 IPF patients and 8 healthy controls.

Data set GSE44426 (Desterke et al., 2015) contains 6 bone marrow samples from primary myelofibrosis and 6 control samples.

Two Data Sets of Normal Human Fibroblasts Treated with TGF-β or Abituzumab

The data set comprises expression data for 17 of 19 fibrosis signature genes. Expression for three of the 17 genes was below lower limit of quantification (LLOQ). The first data set (AB001) thus comprised expression levels for 14 genes, measured in 9 samples. The nine samples can be grouped in three sample groups: NHLF alone, NHLF+TGF-β, NHLF+H358. The second data set (AB002) comprises eleven samples: NHLF treated with 40 ng/ml anti-HEL (3 repeats), NHLF treated with 40 ng/ml Abituzumab (2 repeats), NHLF treated with 10 μg/ml anti-HEL (3 repeats), NHLF treated with 10 μg/ml Abituzumab (3 repeats).

Signature Scoring

We found that our 19-gene and 9-gene signatures can be scored in several ways to yield results that support our claims.

Expression raw intensities can be log.-transformed or not transformed.

Z-normalization: in data sets with multiple samples (>=9) each gene expression vector can be mean- or median-centered and standardized to yield expression Z scores.

Normalization using pre-treatment intensities as a reference: ratios can be calculated from expression intensities pre- and post-treatment. These ratios can be optionally log-scaled.

Summary scores for the signature per sample are calculated as sums, averages, or weighted averages across genes.

Literature-Based Gene List 143 genes associated with up-regulation in SSc and in TGF-stimulated fibroblasts have been proposed by Daigen Xu (TIP Immunology) including four genes from the "Lafyatis signature" that predicts skin disease in patients with diffuse SSc (Farina et al., 2010). 135 are measured in at least one of the three SSc data sets. A list of the 135 genes can be found in Table 9.

Computer Programs Used

| Program | Version | Supplier |
| --- | --- | --- |
| R | 3.0.2 | R Development Core Team |
| limma R package | 3.19.24 | Bioconductor |

Strategy for the Identification of the Desired Fibrosis/SSc Signature

In FIG. 8, the strategy for the identification of the desired fibrosis/SSc signature is outlined. We differ between literature derived and not-literature derived genes. Both gene sets were tested on the three SSc data sets, filtered on the pulmonary fibrosis data sets and finally validated on one more pulmonary fibrosis data set. The single steps are described in detail in the next sections.

Step 1: Towards a Pre-Final Gene List

To obtain a candidate list of fibrosis/SSc related genes we performed a moderated t-test for differential expression analysis as implemented in the R bioconductor package limma (Smyth, 2004) per gene on each SSc data set. Linear models were fitted to every gene with contrasts "SSc—normal" samples. Given the linear model fit, a moderated t-statistics was computed by empirical Bayes moderation of the standard errors towards a common value. p-values were adjusted for multiple testing by the Benjamini Hochberg procedure (Benjamini and Hochberg, 1995) controlling the False Discovery Rate (FDR).

Analysis of Literature-Based Genes

All genes were tested for differential expression between SSc and normal skin on the three SSc data sets as described above. Pre-defined genes from literature were included in the pre-final list of fibrosis genes if they fulfill the following criteria:

Genes have to be significantly up-regulated (adjusted p-value<0.05) in at least one of the three public SSc data sets and genes must not be significantly down-regulated in any of the three data sets.

None of the genes were excluded due to concurrent significant up- and down-regulation across the data sets. 40 of the 135 pre-defined genes from literature met these criteria.

Additional Fibrosis/SSc Genes Based on Public Data Mining

For all other genes not pre-defined from literature criteria were tightened. Genes were included in the pre-final list of up-regulated fibrosis/SSc genes if the following criteria are met:

Genes have to be significantly up-regulated (adjusted p-value<0.05) in (at least) two of the three public SSc data sets and genes must not be significantly down-regulated in any of the three data sets.

62 genes not-derived from literature were found to be up-regulated in SSc compared to healthy skin. Although two of 62 genes were excluded due to significant down-regulation in one SSc data set, resulting in 60 genes that were considered for further analyses.

In total, 100 genes were included in the pre-final list of up-regulated fibrosis/SSc genes.

Step 2: Filtering of Pre-Final Gene List for Differential Expression in Lung Fibrosis Two data sets, GSE24206 and GSE48149, were used to assess whether the genes found to be up-regulated in SSc were up-regulated in pulmonary fibrosis (PF), too. 96 of the 100 genes were present in at least of the two PF data sets. We tested the 96 genes in four comparisons for up-regulation in fibrotic lung tissue with moderated t-tests:

1. GSE24206: normal vs. early IPF
2. GSE24206: normal vs. advanced IPF
3. GSE48149: normal vs. IPF
4. GSE48149: normal vs. SSc-PF To pass this filtering step a gene needed to be significantly up-regulated (Benjamini Hochberg adjusted p-value<0.05) in at least two comparisons and not significantly down-regulated in any comparison. 20 candidate genes were left after step 2.

Step 3: Filtering of Pre-Final Gene List for Up-Regulation in Immune-Related Tissues For the remaining genes from the candidate list of fibrosis/SSc related genes we performed a moderated t-test for differential expression analysis as implemented in the R bioconductor package limma per gene on the normal tissue data set GSE1133. Linear models were fitted to every gene with contrasts "immune—other" samples. Given the linear model fit, a moderated t-statistics was computed by empirical Bayes moderation of the standard errors towards a common value. p-values were adjusted for multiple testing by the Benjamini Hochberg procedure controlling the False Discovery Rate (FDR). One gene (BIRC3) was excluded due to up-regulation in immune-related vs. other normal (non-cancer) tissue samples.

The Fibrosis/SSc 19-Gene Signature

By means of prior knowledge from literature and gene expression info publicly available data sets, we have composed a bona fide fibrosis/SSc signature consisting of 19 non-immune-related genes up-regulated in SSc and pulmonary fibrosis. The complete list of genes is shown in Table 9.

Expression data of 19 genes are normalized (per data set), i.e. mean centered and standardized across samples. Mean over 19 genes is used as Signature Score per sample.

The Fibrosis/SSc TGF-β-Up/Abituzumab-Down (TUAD) 9-Gene Signature

We aimed to select genes for the TGF-β-up/Abituzumab-down signature as a subset of genes of the 19 gene signature. Therefore, we conducted the following experiment. Normal human lung fibroblasts (NHLF) were supplemented with TGF-β and co-cultured with cells from the human epithelial H358 lung cell line. For 14 of 19 genes of the fibrosis signature we were able to yield expression signals. For a gene to be included in the TGF-β-up/Abituzumab-down signature (in the following termed TUAD signature) it had to show an up-regulation after administration of TGF-β (median fold change across 3 repeated experiments). Using this criterion, we selected 9 genes. These 9 genes constitute our 9-gene TUAD signature (see Table 9 denoted by *).

Further, the final TUAD signature of 9 genes was subjected to an experiment with normal human lung fibroblasts (NHFL) that were co-cultured with human H358 cells and treated either with anti-HEL (hen egg lysozyme) or Abituzumab at 40 ng/ml and 10 µg/ml (see description of data set above).

We found that each of the 9 genes (that were previously found to be up-regulated by TGF-β) could be down-regulated by Abituzumab when compared to the anti-HEL control. Thus, the TUAD 9-gene signature represents a TGF-β-inducible fibrosis signature that can be down-modulated by Abituzumab, demonstrated by a) down-regulation of all genes in the 9-gene signature after Abituzumab treatment compared to anti-HEL, and b) because of the down-regulation of the net TUAD 9-gene signature score after Abituzumab treatment compared to anti-HEL.

Differential expression analysis results of the 19 genes included in the Fibrosis/SSc signature are shown in Table 10, Table 11 and Table 12 for the comparisons of SSc to normal skin, in Table 13 for the comparison of SSc-PF to normal lung, in Table 14 for the comparison of UIP/IPF to normal lung, in Table 15 for the comparison of early IPF to normal lung, and in Table 16 for the comparison of advanced IPF to normal lung.

None of the 19 Fibrosis/SSc signature genes is up-regulated in immune-related vs. non-immune-related tissues (Table 17).

Performance of the 19-Gene Fibrosis/SSc and 9-Gene TUAD Signature

Although, single genes show up-regulated expression like RGS5 in SSc compared to normal skin (FIG. 9) and e.g. COL15A1, COL1A1, COMP, IGFBP2a and SSP1 in IPF and SSc-PF compared to normal lung (FIG. 10-FIG. 14a) in distinct data sets, the signature scores derived from the 19-gene Fibrosis/SSc signature and from the 9-gene TUAD signature provide a more robust signal for monitoring fibrosis in skin (FIG. 14b, FIG. 15a, FIG. 15b, FIG. 16a and FIG.

16b), lung (FIG. 17a, FIG. 17b, FIG. 18a and FIG. 18b), liver (FIG. 19a, FIG. 19b, FIG. 20a, FIG. 20b, FIG. 21a and FIG. 21b) and bone marrow (FIG. 22a and FIG. 22b).

For esophagus and kidney fibrosis, where no control tissue expression data is available, genes included in the 19-gene Fibrosis/SSc and 9-gene TUAD signature are coordinately expressed, denoted by a higher than randomly expected Coherence Score (Staub, 2012) obtained by 1000 iterations (Table 18).

In liver samples (GSE61260), the signature scores of the 19-gene Fibrosis/SSc and of the 9-gene TUAD signature correlate well with the Fibrosis score (as described in Hovarth et al., 2014) with Spearman correlation coefficients of 0.505 and 0.523, respectively (Table 19).

CONCLUSIONS

Because our TUAD multi-gene expression signature can be down-modulated by treatment with abituzumab, and because it is linked to disease severity and/or degree of fibrosis in various fibrotic diseases (as mentioned in the preceding paragraphs), the TUAD signature can be regarded as an indicator of high clinical need in fibrotic diseases. The TUAD signature can be used for patient selection for abituzumab therapy: high baseline/pre-treatment levels for the TUAD signature can be used to select patients for which abituzumab has highest potential to achieve therapy success, since we not only demonstrated that high TUAD signature status is linked to fibrotic disease status, but also that abituzumab can effectively down-modulate the TUAD signature. In addition, the TUAD signature can be used to monitor fibrosis—as we had demonstrated links to disease severity, and—because of the demonstrated ability of abituzumab to down-regulated the TUAD signature—it can therefore also be used to monitor abituzumab effectiveness. Because of the mentioned ability of the TUAD signature to serve as a marker predicting therapy response, and because of the link to disease severity or presence of fibrosis in several fibrotic diseases, we consider abituzumab to be a drug that can be used against all fibrotic diseases in general.

Tables

TABLE 8

Literature-based list of genes up-regulated in SSc and in TGF-stimulated fibroblasts present on at least one of the three SSc data sets

| Gene name | |
|---|---|
| SIGLEC1 | sialic acid binding Ig-like lectin 1, sialoadhesin |
| IFI44 | interferon-induced protein 44 |
| COMP | cartilage oligomeric matrix protein |
| THBS1 | thrombospondin 1 |
| SPARC | secreted protein, acidic, cysteine-rich (osteonectin) |
| SPP1 | secreted phosphoprotein 1 |
| TNC | tenascin C |
| FAP | fibroblast activation protein, alpha |
| POSTN | periostin, osteoblast specific factor |
| ELN | elastin |
| SERPINE1 | serpin peptidase inhibitor, clade E (nexin, plasminogen activator inhibitor type 1), member 1 |
| BMP1 | bone morphogenetic protein 1 |
| TIMP1 | TIMP metallopeptidase inhibitor 1 |
| TIMP3 | TIMP metallopeptidase inhibitor 3 |
| MMP1 | matrix metallopeptidase 1 (interstitial collagenase) |
| MMP2 | matrix metallopeptidase 2 (gelatinase A, 72 kDa gelatinase, 72 kDa type IV collagenase) |
| PLAUR | plasminogen activator, urokinase receptor |
| PLOD2 | symbol |

TABLE 8-continued

Literature-based list of genes up-regulated in SSc and in TGF-stimulated fibroblasts present on at least one of the three SSc data sets

| Gene name | |
|---|---|
| HAS2 | hyaluronan synthase 2 |
| LOX | lysyl oxidase |
| LOXL1 | lysyl oxidase-like 1 |
| TGF-β1 | transforming growth factor, beta 1 |
| TGF-β2 | transforming growth factor, beta 2 |
| TGF-β3 | transforming growth factor, beta 3 |
| CYR61 | cysteine-rich, angiogenic inducer, 61 |
| CTGF | connective tissue growth factor |
| THBS2 | thrombospondin 2 |
| ITGB5 | integrin, beta 5 |
| PDGFA | platelet-derived growth factor alpha polypeptide |
| ACTA2 | actin, alpha 2, smooth muscle, aorta |
| SNAI1 | snail family zinc finger 1 |
| EGR1 | early growth response 1 |
| EGR2 | early growth response 2 |
| CCL2 | chemokine (C-C motif) ligand 2 |
| IL6 | interleukin 6 (interferon, beta 2) |
| COL9A1 | collagen, type IX, alpha 1 |
| COL1A1 | collagen, type I, alpha 1 |
| COL9A3 | collagen, type IX, alpha 3 |
| COL6A2 | collagen, type VI, alpha 2 |
| COL5A3 | collagen, type V, alpha 3 |
| COL1A2 | collagen, type I, alpha 2 |
| COL27A1 | collagen, type XXVII, alpha 1 |
| COL13A1 | collagen, type XIII, alpha 1 |
| COL4A5 | collagen, type IV, alpha 5 |
| COL6A6 | collagen, type VI, alpha 6 |
| COL18A1 | collagen, type XVIII, alpha 1 |
| COL14A1 | collagen, type XIV, alpha 1 |
| COL4A3BP | collagen, type IV, alpha 3 (Goodpasture antigen) binding protein |
| COL4A1 | collagen, type IV, alpha 1 |
| COL10A1 | collagen, type X, alpha 1 |
| COL25A1 | collagen, type XXV, alpha 1 |
| COL3A1 | collagen, type III, alpha 1 |
| COL22A1 | collagen, type XXII, alpha 1 |
| COLEC11 | collectin sub-family member 11 |
| COL2A1 | collagen, type II, alpha 1 |
| COL11A1 | collagen, type XI, alpha 1 |
| COL9A2 | collagen, type IX, alpha 2 |
| COL17A1 | collagen, type XVII, alpha 1 |
| COL20A1 | collagen, type XX, alpha 1 |
| COL4A6 | collagen, type IV, alpha 6 |
| COL6A3 | collagen, type VI, alpha 3 |
| COL4A4 | collagen, type IV, alpha 4 |
| COL5A1 | collagen, type V, alpha 1 |
| COLQ | collagen-like tail subunit (single strand of homotrimer) of asymmetric acetylcholinesterase |
| COL11A2 | collagen, type XI, alpha 2 |
| COL6A1 | collagen, type VI, alpha 1 |
| COL8A2 | collagen, type VIII, alpha 2 |
| COL4A3 | collagen, type IV, alpha 3 (Goodpasture antigen) |
| COL4A2 | collagen, type IV, alpha 2 |
| COL5A2 | collagen, type V, alpha 2 |
| COL21A1 | collagen, type XXI, alpha 1 |
| COLEC12 | collectin sub-family member 12 |
| COL29A1 | collagen, type XXIX, alpha-1 |
| COL8A1 | collagen, type VIII, alpha 1 |
| COLEC10 | collectin sub-family member 10 (C-type lectin) |
| COL19A1 | collagen, type XIX, alpha 1 |
| COL15A1 | collagen, type XV, alpha 1 |
| COL12A1 | collagen, type XII, alpha 1 |
| COL16A1 | collagen, type XVI, alpha 1 |
| COL24A1 | collagen, type XXIV, alpha 1 |
| COL23A1 | collagen, type XXIII, alpha 1 |
| COL7A1 | collagen, type VII, alpha 1 |
| MMP9 | matrix metallopeptidase 9 (gelatinase B, 92 kDa gelatinase, 92 kDa type IV collagenase) |
| MMP19 | matrix metallopeptidase 19 |
| MMP27 | matrix metallopeptidase 27 |
| MMP16 | matrix metallopeptidase 16 (membrane-inserted) |
| MMP20 | matrix metallopeptidase 20 |
| MMP28 | matrix metallopeptidase 28 |
| MMP12 | matrix metallopeptidase 12 (macrophage elastase) |

TABLE 8-continued

Literature-based list of genes up-regulated in SSc and in TGF-stimulated fibroblasts present on at least one of the three SSc data sets

| | Gene name |
|---|---|
| MMP26 | matrix metallopeptidase 26 |
| MMP7 | matrix metallopeptidase 7 (matrilysin, uterine) |
| MMP15 | matrix metallopeptidase 15 (membrane-inserted) |
| MMP11 | matrix metallopeptidase 11 (stromelysin 3) |
| MMP3 | matrix metallopeptidase 3 (stromelysin 1, progelatinase) |
| MMP24 | matrix metallopeptidase 24 (membrane-inserted) |
| MMP21 | matrix metallopeptidase 21 |
| MMP14 | matrix metallopeptidase 14 (membrane-inserted) |
| MMP17 | matrix metallopeptidase 17 (membrane-inserted) |
| MMP8 | matrix metallopeptidase 8 (neutrophil collagenase) |
| MMP13 | matrix metallopeptidase 13 (collagenase 3) |
| MMP25 | matrix metallopeptidase 25 |
| MMP10 | matrix metallopeptidase 10 (stromelysin 2) |
| MMP23B | matrix metallopeptidase 23B |
| ITGA2B | integrin, alpha 2b (platelet glycoprotein IIb of IIb/IIIa complex, antigen CD41) |
| ITGAE | integrin, alpha E (antigen CD103, human mucosal lymphocyte antigen 1 alpha polypeptide) |
| ITGAM | integrin, alpha M (complement component 3 receptor 3 subunit) |
| ITGAV | integrin, alpha V |
| ITGB1 | integrin, beta 1 (fibronectin receptor, beta polypeptide, antigen CD29 includes MDF2, MSK12) |
| ITGA3 | integrin, alpha 3 (antigen CD49C, alpha 3 subunit of VLA-3 receptor) |
| ITGA1 | integrin, alpha 1 |
| ITGB2 | integrin, beta 2 (complement component 3 receptor 3 and 4 subunit) |
| ITGB3BP | integrin beta 3 binding protein (beta3-endonexin) |
| ITGAL | integrin, alpha L (antigen CD11A (p180), lymphocyte function-associated antigen 1 alpha polypeptide) |
| ITGB1BP3 | integrin beta 1 binding protein 3 |
| ITGB3 | integrin, beta 3 (platelet glycoprotein IIIa, antigen CD61) |
| ITGB8 | integrin, beta 8 |
| ITGA8 | integrin, alpha 8 |
| ITGB6 | integrin, beta 6 |
| ITGB7 | integrin, beta 7 |
| ITGA2 | integrin, alpha 2 (CD49B, alpha 2 subunit of VLA-2 receptor) |
| ITGB1BP2 | integrin beta 1 binding protein (melusin) 2 |
| ITGA6 | integrin, alpha 6 |
| ITGA5 | integrin, alpha 5 (fibronectin receptor, alpha polypeptide) |
| ITGA10 | integrin, alpha 10 |
| ITGB4 | integrin, beta 4 |
| ITGAX | integrin, alpha X (complement component 3 receptor 4 subunit) |
| ITGA9 | integrin, alpha 9 |
| ITGA7 | integrin, alpha 7 |
| ITGAD | integrin, alpha D |
| ITGA4 | integrin, alpha 4 (antigen CD49D, alpha 4 subunit of VLA-4 receptor) |
| ITGB1BP1 | integrin beta 1 binding protein 1 |
| ITGA11 | integrin, alpha 11 |
| ITGBL1 | integrin, beta-like 1 (with EGF-like repeat domains) |
| CSPG2 | chondroitin sulfate proteoglycan 2 |
| ITGB4BP/EIF6 | eukaryotic translation initiation factor 6 |

TABLE 9

19-gene SSc/fibrosis signature and the 9-gene TUAD signature (genes marked by *)

| symbol | gene name | NCBI RefSeq |
|---|---|---|
| COL15A1* | collagen, type XV, alpha 1 | NM_001855 |
| COL1A1* | collagen, type I, alpha 1 | NM_000088 |
| COMP* | cartilage oligomeric matrix protein | NM_000095 |
| RGS5 | regulator of G-protein signaling 5 | NM_003617 |
| COL10A1* | collagen, type X, alpha 1 | NM_000493 |
| COL5A1* | collagen, type V, alpha 1 | NM_000093 |
| IGFBP2 | insulin-like growth factor binding protein 2, 36 kDa | NM_000597 |
| LOXL1 | lysyl oxidase-like 1 | NM_005576 |
| MOXD1 | monooxygenase, DBH-like 1 | NM_015529 |
| ADRA2A | adrenoceptor alpha 2A | NM_000681 |
| COL5A2* | collagen, type V, alpha 2 | NM_000393 |
| MMP10 | matrix metallopeptidase 10 (stromelysin 2) | NM_002425 |
| TNFRSF21 | tumor necrosis factor receptor superfamily, member 21 | NM_014452 |
| ITGA7* | integrin, alpha 7 | NM_002206 |
| TGF-β3 | transforming growth factor, beta 3 | NM_003239 |
| MMP11* | matrix metallopeptidase 11 (stromelysin 3) | NM_005940 |
| SPP1 | secreted phosphoprotein 1 | NM_000582 |
| CCL2 | chemokine (C-C motif) ligand 2 | NM_002982 |
| TNC* | tenascin C | NM_002160 |

TABLE 10

Results of moderated t-tests of 19 fibrosis/SSc signature genes comparing SSc to normal skin samples in GSE45485

| Gene symbol | logFC | p-value | adj. p-value |
|---|---|---|---|
| COL15A1 | −0.05354741 | 0.63284437 | 0.85974021 |
| COL1A1 | −0.0564569 | 0.32613521 | 0.65911219 |
| COMP | 0.06396207 | 0.35028311 | 0.6787201 |
| RGS5 | 0.76552328 | 8.21E−07 | 0.00076264 |
| COL10A1 | 0.14700345 | 0.15561912 | 0.48216536 |
| COL5A1 | 0.17074828 | 0.18609626 | 0.52034919 |
| IGFBP2 | 0.17849483 | 0.07746999 | 0.3473223 |
| LOXL1 | 0.00652931 | 0.95853833 | 0.98965775 |
| MOXD1 | 1.7533069 | 1.09E−05 | 0.00250698 |
| ADRA2A | 0.58765 | 0.0010264 | 0.02967007 |
| COL5A2 | −0.10143678 | 0.21608038 | 0.55557497 |
| MMP10 | 0.78422241 | 0.00161561 | 0.03848804 |
| TNFRSF21 | 0.07153966 | 0.41999428 | 0.73134954 |
| ITGA7 | 0.2628 | 0.06029334 | 0.30433949 |
| TGF-β3 | 0.16204828 | 0.07167408 | 0.33376361 |
| MMP11 | 0.02576552 | 0.87854852 | 0.9641284 |
| SPP1 | 0.11211086 | 0.03788071 | 0.23926337 |
| CCL2 | 0.0468331 | 0.42387631 | 0.73379499 |
| TNC | 0.0137 | 0.93305485 | 0.98151167 | logFC = log fold change (from normal skin to SSc)

TABLE 11

Results of moderated t-tests of 19 fibrosis/SSc signature genes comparing SSc to normal skin samples in GSE32413

| Gene symbol | logFC | p-value | adj. p-value |
|---|---|---|---|
| COL15A1 | 8.65252005 | 1.03E−08 | 7.82E−06 |
| COL1A1 | 5.43265134 | 0.00155515 | 0.04371919 |
| COMP | 14.7144265 | 5.72E−08 | 2.83E−05 |
| RGS5 | 10.968877 | 3.13E−10 | 4.76E−07 |
| COL10A1 | 15.6671591 | 0.00031919 | 0.01472844 |
| COL5A1 | 4.77696658 | 8.35E−06 | 0.00103754 |
| IGFBP2 | 5.12541043 | 0.00010114 | 0.00668004 |
| LOXL1 | 7.84100134 | 1.77E−07 | 6.55E−05 |
| MOXD1 | 2.29202005 | 0.00022047 | 0.01145535 |
| ADRA2A | 8.27779545 | 0.0013305 | 0.03929527 |
| COL5A2 | 5.45322193 | 0.00029239 | 0.01384761 |
| MMP10 | 3.81981016 | 0.03358148 | 0.27003295 |
| TNFRSF21 | 1.99499398 | 0.00169115 | 0.04633193 |
| ITGA7 | 9.61105481 | 6.16E−06 | 0.00087583 |
| TGF-β3 | 8.35457821 | 1.64E−05 | 0.00172723 |
| MMP11 | 7.37892112 | 0.00018876 | 0.01035532 |
| SPP1 | 11.7482176 | 0.00097261 | 0.03164442 |
| CCL2 | 18.0195571 | 3.18E−12 | 1.05E−08 |
| TNC | 7.44044385 | 3.28E−05 | 0.00296034 | logFC = log fold change (from normal skin to SSc)

TABLE 12

Results of moderated t-tests of 19 fibrosis/SSc signature genes comparing SSc to normal skin samples in GSE9285

| Gene symbol | logFC | p-value | adj. p-value |
|---|---|---|---|
| COL15A1 | −0.80155204 | 0.4462029 | 0.64884688 |
| COL1A1 | 2.7221 | 0.12952504 | 0.32731037 |
| COMP | 13.0156364 | 0.00032598 | 0.01168603 |
| RGS5 | 0.50973333 | 0.7285143 | 0.8421874 |
| COL10A1 | 0.42446491 | 0.49108962 | 0.68406853 |
| COL5A1 | −0.02584363 | 0.91217968 | 0.95182504 |
| IGFBP2 | 6.09920351 | 0.00147053 | 0.02511234 |
| LOXL1 | 0.24474737 | 0.69148258 | 0.8189216 |
| MOXD1 | 0.12781754 | 0.29020488 | 0.5176974 |
| ADRA2A | NA | NA | NA |
| COL5A2 | 1.29160053 | 0.25303864 | 0.47936774 |
| MMP10 | −0.02789369 | 0.54630288 | 0.72218046 |
| TNFRSF21 | 0.1827807 | 0.00237558 | 0.03309656 |
| ITGA7 | 2.09964561 | 0.12139797 | 0.31533591 |
| TGF-β3 | 0.79875045 | 0.34075749 | 0.56391476 |
| MMP11 | 0.13554094 | 0.15 | 0.33526052 |
| SPP1 | 5.44541353 | 0.03795579 | 0.16699841 |
| CCL2 | 2.2879614 | 0.30601935 | 0.5326055 |
| TNC | 1.03070292 | 0.03803824 | 0.16720506 | logFC = log fold change (from normal skin to SSc),
NA = not available (ADRA2A is not measured in GSE9285)

TABLE 13

Results of moderated t-tests of 19 fibrosis/SSc signature genes comparing SSc-PF to normal lung samples in GSE48149

| Gene symbol | logFC | p-value | adj. p-value |
|---|---|---|---|
| COL15A1 | 1.9608 | <0.0001 | 1.00E−04 |
| COL1A1 | 2.086 | <0.0001 | 3.00E−04 |
| COMP | 2.5904 | <0.0001 | 1.00E−04 |
| RGS5 | 1.1167 | 0.0027 | 0.017 |
| COL10A1 | 1.3117 | 1.00E−04 | 6.00E−04 |
| COL5A1 | 0.6399 | 0.0628 | 0.1754 |
| IGFBP2 | 1.5049 | <0.0001 | 1.00E−04 |
| LOXL1 | 0.3851 | 0.0102 | 0.046 |
| MOXD1 | 0.6583 | 0.0225 | 0.0806 |
| ADRA2A | 0.4079 | 0.022 | 0.0806 |
| COL5A2 | 1.1264 | 0.0032 | 0.0191 |
| MMP10 | 1.3084 | 0.0042 | 0.0233 |
| TNFRSF21 | 1.1712 | <0.0001 | <0.0001 |
| ITGA7 | 0.5962 | 0.0072 | 0.0343 |
| TGF-β3 | 1.3211 | <0.0001 | 4.00E−04 |
| MMP11 | 1.8952 | 3.00E−04 | 0.0026 |
| SPP1 | 3.6653 | <0.0001 | 1.00E−04 |
| CCL2 | 1.6668 | 0.0019 | 0.0131 |
| TNC | 0.7709 | 0.0059 | 0.0293 | logFC = log fold change (from normal lung to SSc-PF)

TABLE 14

Results of moderated t-tests of 19 fibrosis/SSc signature genes comparing UIP/IPF to normal lung samples in GSE48149

| Gene symbol | logFC | p-value | adj. p-value |
|---|---|---|---|
| COL15A1 | 1.5947 | <0.0001 | 3.00E−04 |
| COL1A1 | 2.2934 | <0.0001 | <0.0001 |
| COMP | 2.4615 | <0.0001 | <0.0001 |
| RGS5 | 1.1082 | 4.00E−04 | 0.0027 |
| COL10A1 | 1.1817 | <0.0001 | <0.0001 |
| COL5A1 | 0.8224 | 0.0021 | 0.0109 |
| IGFBP2 | 1.2668 | <0.0001 | 1.00E−04 |
| LOXL1 | 0.3737 | 9.00E−04 | 0.0056 |
| MOXD1 | 0.8316 | <0.0001 | 4.00E−04 |
| ADRA2A | 0.1787 | 0.3115 | 0.5192 |
| COL5A2 | 1.0829 | 1.00E−04 | 7.00E−04 |
| MMP10 | 1.121 | 0.0208 | 0.0761 |
| TNFRSF21 | 1.0945 | <0.0001 | <0.0001 |
| ITGA7 | 0.366 | 0.0074 | 0.0321 |
| TGF-β3 | 1.222 | <0.0001 | 1.00E−04 |
| MMP11 | 2.0049 | <0.0001 | 1.00E−04 |
| SPP1 | 3.1784 | <0.0001 | 2.00E−04 |
| CCL2 | 1.4158 | 0.0052 | 0.0236 |
| TNC | 0.6445 | 0.0081 | 0.0333 | logFC = log fold change (from normal lung to UIP/IPF)

TABLE 15

Results of moderated t-tests of 19 fibrosis/SSc signature genes comparing early IPF to normal lung samples in GSE24206

| Gene symbol | logFC | p-value | adj. p-value |
|---|---|---|---|
| COL15A1 | 2.4835 | <0.0001 | 7.00E−04 |
| COL1A1 | 1.5705 | 1.00E−04 | 0.0015 |
| COMP | 2.0974 | 4.00E−04 | 0.0053 |
| RGS5 | 0.8922 | 0.002 | 0.0158 |
| COL10A1 | 1.8361 | 0.0021 | 0.0158 |
| COL5A1 | 0.9854 | 0.0021 | 0.0158 |
| IGFBP2 | 1.4311 | 0.0039 | 0.0218 |
| LOXL1 | 1.1768 | 0.0049 | 0.0258 |
| MOXD1 | 0.7065 | 0.0051 | 0.0258 |
| ADRA2A | 0.9086 | 0.0064 | 0.0308 |
| COL5A2 | 0.712 | 0.0092 | 0.0369 |
| MMP10 | 1.4297 | 0.0725 | 0.1699 |
| TNFRSF21 | 0.8836 | 0.014 | 0.0539 |
| ITGA7 | 0.3274 | 0.1951 | 0.3345 |
| TGF-β3 | 0.2844 | 0.0418 | 0.1143 |
| MMP11 | 0.0967 | 0.5179 | 0.666 |
| SPP1 | 1.2133 | 0.0943 | 0.2105 |
| CCL2 | −1.3519 | 0.0149 | 0.0551 |
| TNC | 0.2502 | 0.5779 | 0.6849 | logFC = log fold change (from normal lung to early IPF)

TABLE 16

Results of moderated t-tests of 19 fibrosis/SSc signature genes comparing advanced IPF to normal lung samples in GSE24206

| Gene symbol | logFC | p-value | adj. p-value |
|---|---|---|---|
| COL15A1 | 2.5317 | <0.0001 | 2.00E−04 |
| COL1A1 | 1.7003 | 1.00E−04 | 0.0013 |
| COMP | 2.6938 | <0.0001 | 1.00E−04 |
| RGS5 | 0.9015 | 6.00E−04 | 0.0062 |
| COL10A1 | 1.6965 | <0.0001 | 2.00E−04 |
| COL5A1 | 0.9463 | 0.0017 | 0.0136 |
| IGFBP2 | 2.555 | <0.0001 | <0.0001 |
| LOXL1 | 1.4254 | 5.00E−04 | 0.0055 |
| MOXD1 | 0.6028 | 0.0152 | 0.0729 |
| ADRA2A | 0.9429 | 5.00E−04 | 0.0055 |
| COL5A2 | 0.6755 | 0.0108 | 0.0576 |
| MMP10 | 2.7984 | 1.00E−04 | 0.0016 |
| TNFRSF21 | 1.2348 | 7.00E−04 | 0.0065 |
| ITGA7 | 0.7677 | 0.0063 | 0.0435 |
| TGF-β3 | 0.3516 | 0.0087 | 0.052 |
| MMP11 | 0.117 | 0.4332 | 0.6515 |
| SPP1 | 1.2031 | 0.0672 | 0.1955 |
| CCL2 | −0.7953 | 0.0666 | 0.1955 |
| TNC | 0.2762 | 0.5107 | 0.7013 | logFC = log fold change (from normal lung to advanced IPF)

TABLE 17

Results of moderated t-tests of 19 fibrosis/SSc signature genes comparing immune-related to non-immune/non-cancer samples in GSE1133

| Gene symbol | logFC | p-value | adj. p-value |
|---|---|---|---|
| COL15A1 | −0.57352943 | 0.00475152 | 0.00902789 |
| COL1A1 | −0.5599531 | 0.00583927 | 0.01008602 |
| COMP | −0.42298976 | 0.03724964 | 0.05055309 |
| RGS5 | −1.26000495 | 6.18E−10 | 5.87E−09 |
| COL10A1 | −0.38023756 | 0.06112002 | 0.06831061 |
| COL5A1 | −0.61908543 | 0.00230896 | 0.00548379 |
| IGFBP2 | −0.91215384 | 7.28E−06 | 3.46E−05 |
| LOXL1 | −0.5903443 | 0.00366005 | 0.00772677 |
| MOXD1 | −0.70997396 | 0.00047627 | 0.00142367 |
| ADRA2A | −0.52178229 | 0.01019951 | 0.01490697 |
| COL5A2 | −0.54032041 | 0.00781064 | 0.01236685 |
| MMP10 | −0.08672332 | 0.66921027 | 0.70638861 |
| TNFRSF21 | −0.03008653 | 0.88216925 | 0.88216925 |
| ITGA7 | −0.98300833 | 1.35E−06 | 8.54E−06 |
| TGF-β3 | −1.30537499 | 1.49E−10 | 2.82E−09 |
| MMP11 | −0.38530818 | 0.05775116 | 0.06831061 |
| SPP1 | −0.8725154 | 1.78E−05 | 6.75E−05 |
| CCL2 | −0.70471063 | 0.00052451 | 0.00142367 |
| TNC | −0.39344598 | 0.05266811 | 0.06671293 | logFC = log fold change (from non-immune to immune-related samples)

TABLE 18

Coherence scores of the 19-gene SSc/fibrosis signature and the 9-gene TUAD signature in distinct indications with minimal and maximal Coherence scores calculated from randomly picked 19 and 9 genes, respectively, in the respective data set

| data set | tissue/indication | min CS random 19 genes | max CS random 19 genes | CS 19-gene SSc/fibrosis signature | min CS random 9 genes | max CS random 9 genes | CS 9-gene TUAD signature |
|---|---|---|---|---|---|---|---|
| GSE22459 | kidney | −0.035 | 0.192 | 0.161 | −0.086 | 0.329 | 0.385 |
| GSE61260 | liver | −0.03 | 0.122 | 0.226 | −0.068 | 0.242 | 0.245 |
| GSE48452 | liver | −0.029 | 0.138 | 0.214 | −0.073 | 0.234 | 0.278 |
| GSE49541 | liver | −0.031 | 0.118 | 0.184 | −0.071 | 0.199 | 0.267 |
| GSE39491 | esophagus | −0.035 | 0.225 | 0.177 | −0.091 | 0.239 | 0.278 |
| GSE26886 | esophagus | −0.035 | 0.106 | 0.201 | −0.084 | 0.212 | 0.44 |
| GSE3720 | esophagus | −0.033 | 0.174 | 0.202 | −0.078 | 0.243 | 0.558 |
| GSE47460 | lung | −0.029 | 0.082 | 0.471 | −0.085 | 0.326 | 0.653 |
| GSE24988 | lung | −0.031 | 0.138 | 0.265 | −0.075 | 0.207 | 0.472 |
| GSE17978 | lung | −0.031 | 0.184 | 0.336 | −0.086 | 0.311 | 0.406 |
| GSE53845 | lung | −0.036 | 0.08 | 0.525 | −0.08 | 0.258 | 0.607 |

TABLE 19

Spearman correlation between signature scores of the 19-gene SSc/fibrosis signature and the 9-gene TUAD signature and inflammation, NAS (NADLF activity score) and fibrosis score in GSE61260

| | 19-gene SSc/fibrosis signature score | 9-gene TUAD signature score |
|---|---|---|
| Inflammation score | 0.354 | 0.335 |
| NAS | 0.270 | 0.284 |
| Fibrosis score | 0.505 | 0.523 |

BIBLIOGRAPHY

1 Benjamini Y, and Hochberg Y. Controlling the false discovery rate: a practical and powerful approach to multiple testing. Journal of the Royal Statistical Society Series B. 1995; 57, 289-300.

2 Farina G, Lafyatis D, Lemaire R, Lafyatis R. A four-gene biomarker predicts skin disease in patients with diffuse cutaneous systemic sclerosis. Arthritis Rheum. 2010 February; 62(2):580-8.

3 Hinchcliff M, Huang C C, Wood T A, Matthew Mahoney J et al. Molecular signatures in skin associated with clinical improvement during mycophenolate treatment in systemic sclerosis. J Invest Dermatol 2013 August; 133 (8):1979-89.

4 Meltzer E B, Barry W T, D'Amico T A, Davis R D et al. Bayesian probit regression model for the diagnosis of pulmonary fibrosis: proof-of-principle. BMC Med Genomics 2011 Oct. 5; 4:70.

5 Milano A, Pendergrass S A, Sargent J L, George L K et al. Molecular subsets in the gene expression signatures of scleroderma skin. PLoS One 2008 Jul. 16; 3(7):e2696.

6 Pendergrass S A, Lemaire R, Francis I P, Mahoney J M et al. Intrinsic gene expression subsets of diffuse cutaneous systemic sclerosis are stable in serial skin biopsies. J Invest Dermatol 2012 May; 132(5):1363-73.

7 Smyth G K. Linear models and empirical Bayes methods for assessing differential expression in microarray experiments. Statistical Applications in Genentics and Molecular Biology. 2004; 3(1), article 3.

8 Su A I, Wiltshire T, Batalov S, Lapp H et al. A gene atlas of the mouse and human protein-encoding transcriptomes. Proc Natl Acad Sci USA 2004 Apr. 20; 101 (16): 6062-7.

9 Staub E. An interferon response gene expression signature is activated in a subset of medulloblastomas. Transl Oncol. 2012 August; 5(4):297-304. Epub 2012 Aug. 1

Example 5

Phase I Study Clinical Study

A Phase I trial was initiated to determine safety, pharmacokinetics (and antitumor activity) of CRPC patients treated with DI17E6 including effects on prostate-specific antigen, circulating tumor cells (CTC), and soft tissue and bone metastases. All patients were suffering from a progressing disease after chemotherapy. Patients were treated with iv-infusions of 250, 500, 1000 or 1500 mg DI17E6 given over 1 hour.

Eligible patients were aged 18 years or older and had histologically or cytologically proven prostate cancer with evidence of bone metastases after prior chemotherapy. Patients had either undergone bilateral orchiectomy or were receiving continuous androgen deprivation therapy with a gonadotropin releasing hormone agonist or antagonist and had stopped anti-androgen therapy for at least 4 weeks prior to enrolment. Patients were required to either be on stable (i.e. at least 3 months) ongoing bisphosphonate therapy or without any bisphosphonate therapy, with a total serum testosterone level less than 50 ng/dL. All patients had evidence of progressive disease, defined as at least two prostate-specific antigen (PSA) values above the individual nadir level with a minimum increase of 10% each determined at least two weeks prior to screening; nodal or visceral progression was sufficient for inclusion independent of PSA. In addition, patients had to have an Eastern Cooperative Oncology Group (ECOG) score of 0 to 2, a life expectancy of at least 3 months, and adequate hematologic, renal and hepatic function. An institutional review board at each study center approved the study protocol, and all patients provided written informed consent.

In this phase 1, multicenter, open-label, dose-escalation study, mCRPC patients were administered three intravenous infusions of EMD 525797 at doses of 250, 500, 1000, or 1500 mg given over one hour every two weeks prior to response assessment at the end of week 6. Patients without evidence of progressive disease were eligible to receive further fortnightly doses until disease progression or unacceptable toxicity. Dose-limiting toxicities (DLTs) were assessed during the first six weeks and patients were followed for safety until four weeks after the last administration of EMD 525797. Patients were recruited in four sequential dose cohorts; after the last of six patients within a dose cohort had reached the end of week 6, a Safety Monitoring Committee determined subsequent dose escalation.

Twenty-six male patients aged between 43 and 80 years (median age, 66 years) were enrolled and received at least one intravenous infusion of EMD 525797, constituting the safety population. All patients were of Caucasian origin. In general, demographic characteristics were comparable across the four dose cohorts (Table 1a), with a median time since first diagnosis of 5.2 years (range, 2-18 years) and a median time from diagnosis to first metastatic disease of 0.1 years (range, 0-16 years). Two patients withdrew before the end of the DLT period and were subsequently replaced, with 24 patients receiving three doses of EMD 525797 through treatment Week 6.

TABLE 1a

Patient baseline demographics (safety population).

| Characteristic | DI17E6 (EMD 525797) dose cohort | | | | |
|---|---|---|---|---|---|
| | 250 mg (N = 8) | 500 mg (N = 6) | 1000 mg (N = 6) | 1500 mg (N = 6) | Total (N = 26) |
| Age, years, mean (range) | 67 (57-78) | 63 (47-77) | 62 (43-79) | 66 (52-80) | 65 (43-80) |
| Weight, kg, mean | 82.2 | 85.8 | 80.5 | 93.7 | 85.3 |
| BMI, kg/m², mean | 26.2 | 28.1 | 26.0 | 28.9 | 27.2 |

BMI, body mass index;

In Summary (Table 1b):

| | |
|---|---|
| Objectives | Safety, tolerability and PK after multiple rising i.v. doses |
| | Determine changes in markers of bone metabolism during treatment |
| | Investigate changes in efficacy parameters within the whole dose range |
| | Identification of potential pharmacodynamic markers |
| Number of subjects | Per dose level n = 6 |
| Dose selection | 250, 500, 1000, 1500 mg as 1 h i.v. infusion |
| Treatment duration | 6 weeks (every second week) and 4 weeks follow up. Option for further treatment if patient is non-progressive. |
| Dose escalation | Dose escalation will be based on the toxicity assessment (DLT) after 6 weeks. |

The clinical results from this Phase I clinical trial is being conducted at 3 sites in Germany and at one site in Belgium.

Treatment Duration 24 patients (43-80 years) received 3 doses (weeks 1, 3 and 5) prior to response assessment at the end of week 6. Dose-limiting toxicities (DLTs) were assessed over the first 6 weeks and patients were followed for safety until 4 weeks after the last administration of DI17E6.

Table 2a summarizes drug exposure per patient in each cohort. Patients had a mean EMD 525797 exposure duration of 117.5 days (median, 74.5 days; range, 14-534 days). Thirteen of 24 patients had a longer exposure time than expected (>84 days), with two patients in the 500 mg cohort remaining on treatment for 297 and 534 days, and one patient in the 1000 mg cohort receiving treatment for 310 days. No DLTs were reported within the DLT period of 6 weeks. All patients experienced at least one TEAE and no dose-dependent relationship in TEAEs was observed.

TABLE 2a

DI17E6 exposure per patient in each of the dose cohorts

| Pt | 250 mg | 500 mg | 1000 mg | 1500 mg |
|---|---|---|---|---|
| 1 | 42 | 297 | 113 | 91 |
| 2 | 42 | 380+ | 121 | 84+ |
| 3 | 42 | 85 | 198+ | 72+ |
| 4 | 42 | 142 | 41 | 64+ |
| 5 | 56 | 140 | 56 | 77+ |
| 6 | 98 | 56 | 43 | 57+ |
| 7 | 14* | | | |
| 8 | 28* | | | |

+= ongoing treatment;
*dropped out pts (1 and 2 infusions only)

The study protocol stated, that subjects will receive every other week at least 3 doses (250, 500, 1000 mg/each 2 weeks) of DI17E6.

TABLE 2b

This table shows the values of the treatment duration (state: August 2010).
Dose level 1: 250 mg DI17E6; dose level 2: 500 mg DI17E6; dose level 3: 1000 mg DI17E6; and dose level 4: 1500 mg DI17E6.

| Dose Level | Patients/No. weeks treatment | | | | | | | | | | | | | |
|---|---|---|---|---|---|---|---|---|---|---|---|---|---|---|
| | 1001 | 1002 | 1003 | 1004 | 1005 | 1006 | 1008 | 1010 | 2001 | 2002 | 2003 | 2005 | 2007 | 2009 |
| 1 | 6.3 | 6.3 | 3.3 | 6.0 | 6.1 | 9.1 | 4.1 | 13.0 | | | | | | |
| 2 | | | | | | | | | 42.3 | 49.3 | 12.1 | 18.3 | 20.0 | 6.4 |

TABLE 2b-continued

This table shows the values of the treatment duration (state: August 2010).
Dose level 1: 250 mg DI17E6; dose level 2: 500 mg DI17E6; dose level 3: 1000 mg
DI17E6; and dose level 4: 1500 mg DI17E6.

3
4

| Dose Level | Patients/No. weeks treatment | | | | | | | | | | | |
|---|---|---|---|---|---|---|---|---|---|---|---|---|
| | 3001 | 3002 | 3003 | 3004 | 3005 | 3006 | 4002 | 4003 | 4004 | 4005 | 4009 | 4011 |
| 1 | | | | | | | | | | | | |
| 2 | | | | | | | | | | | | |
| 3 | 14.1 | 17.8 | 24.3 | 8.0 | 7.1 | 6.1 | | | | | | |
| 4 | | | | | | | 9.4 | 6.4 | 6.3 | 9.1 | 6.1 | 2.43 |

Safety/Side Effects

Table 3 summarizes drug-related TEAEs. Eleven patients (42.3%) experienced drug-related TEAEs, which were most commonly reported in the system organ class "Skin and subcutaneous tissue disorders" (4 patients total; pruritus generalized, erythema, rash), "General disorders and administration site conditions" (3 patients total; fatigue, mucosal inflammation, edema peripheral), "Gastrointestinal disorders" (2 patients total; dry mouth, swollen tongue, upper gastrointestinal hemorrhage), and "Infections and infestations" (2 patients total; rhinitis, septicemia). Only two patients (7.7%) had a drug-related grade 3 or 4 TEAE: one patient in the 500 mg cohort experienced a grade 3 increase of gamma-glutamyltransferase (GGT) and a single patient in the 1000 mg cohort experienced a grade 3 septicemia.

Two patients experienced serious TEAEs that were considered to be related to treatment. These were a grade 1 upper gastrointestinal hemorrhage in a patient in the 250 mg cohort and a grade 3 septicemia in one patient in the 1000 mg cohort. At screening, this latter patient had an ongoing diagnosis of urinary tract infection and recurrent events of septicemia of which the last event was considered related to DI17E6 (EMD 525797). Four patients died and investigators assessed all deaths as not reasonably related to EMD 525797.

Six patients (23.1%) permanently discontinued treatment due to TEAEs, including 4 patients in the 250 mg cohort (upper gastrointestinal hemorrhage at day 12, muscular weakness at day 53, paraplegia at day 46, and ureteric obstruction at day 30), and 1 patient each in the 500 mg (grade 3 GGT increase at day 534) and 1500 mg (metastases to central nervous system at day 85) cohorts. No administration site skin reactions were reported. Post-baseline hematology and biochemistry toxicity shifts to grade 3 or 4 occurred in 8 patients. However, there were no obvious trends in laboratory findings, vital signs or ECG recordings. Overall, 65.4% of patients had the same worst ECOG performance status on treatment compared with baseline.

TABLE 3

Drug-related treatment emergent adverse events* (TEAEs).

| TEAEs related to EMD 525797 | n (%) |
|---|---|
| Patients with events | 11 (42) |
| Skin and subcutaneous tissue disorders | 4 (15) |
| Pruritus generalized | 2 (8) |
| Erythema | 1 (4) |
| Rash | 1 (4) |
| General disorders and administration site conditions | 3 (12) |
| Fatigue | 1 (4) |

TABLE 3-continued

Drug-related treatment emergent adverse events* (TEAEs).

| TEAEs related to EMD 525797 | n (%) |
|---|---|
| Mucosal inflammation | 1 (4) |
| Edema peripheral | 1 (4) |
| Gastrointestinal disorders | 2 (8) |
| Dry mouth | 1 (4) |
| Swollen tongue | 1 (4) |
| Upper gastrointestinal hemorrhage | 1 (4) |
| Infections and infestations | 2 (8) |
| Rhinitis | 1 (4) |
| Septicemia† | 1 (4) |
| Eye disorders | 1 (4) |
| Vision blurred | 1 (4) |
| Investigations | 1 (4) |
| Blood pressure increase | 1 (4) |
| Musculoskeletal and connective tissue disorders | 1 (4) |
| Arthralgia | 1 (4) |
| Nervous system disorders | 1 (4) |
| Dysgeusia | 1 (4) |
| Respiratory, thoracic, and mediastinal disorders | 1 (4) |
| Dyspnea | 1 (4) |

*MedDRA Primary System Organ Class. MedDRA Preffered Term Version 13.0.
†Grade 3 occurred after the first 6 weeks (dose limiting toxicity period).

Examples of Observed Side Effect:

(i) A 62 year-old male experienced grade 1 upper gastrointestinal bleeding 13 days after the first and only infusion of DI17E6 (250 mg). The subject presented with non-serious hematemesis and was hospitalized. Gastroscopy showed a lesion in the distal esophagus. Active bleeding was excluded, the subject was treated with omeprazole, and the event resolved (ii) A 79 year-old patient developed septicemia (grade 2) due to E. faecalis 1 days after the most recent and 9 weeks after the first infusion of DI17E6 (EMD 525797) (1000 mg). The patient was hospitalized and discharged with recovery. A month later, the patient developed a second septicemia episode (grade3) again due to E. faecalis 4 days after the most recent and 2.5 months after the first infusion. The patient was hospitalized and discharged with recovery. Another month later, the patient developed a third septicemia episode (grade 3) 4 days after the most recent and 3.5 months after the first infusion, which was attributed to EMD 525797.

In Summary:

Accumulating safety data have been reviewed at all 4 SMCs

Overall no DLTs have been observed: DLT is defined as any grade 3 or 4 hematological or non-hematological toxicity occurring until end of week 6 suspected to be reasonably related to the investigational product by the Investigator and/or Sponsor except for allergic/hypersensitivity reactions and any out-of-range laboratory values without clinical correlate which are reversible within 7 days.

No MTD reached until now

Overall only 2 SAEs have been observed as related to study medication

Pharmacokinetics and Pharmacodynamics

After single and multiple doses, EMD 525797 showed a dose-dependent, non-linear PK profile. After the first 1-hour intravenous infusion, $C_{max}$ of DI17E6 (EMD 525797) was generally reached within 1-2 hours after the start of dosing. The elimination half-life increased with dose as a consequence of EMD 525797 clearance increasing with dose, whereas mean volume of distribution remained constant over the dose range (Table 4).

As given in Table 4 below, administration of cohort 2 CRPC patients with 500 mg/each 2 weeks reached serum levels with IC95, whereas patients from cohort 1 with 250 mg/each 2 weeks failed. The serum trough concentration of EMD 525797 in cohort 2, 500 mg/each 2 weeks, is above the $IC_{95}$ and reach the $IC_{99}$ of the non-linear CL pathway (250 mg/each 2 weeks failed).

TABLE 4

|  | 250 mg (N = 6) | 500 mg (N = 6) | 1000 mg (N = 6) | 1500 mg (N = 6) |
|---|---|---|---|---|
| $C_{max}$, µg/mL, mean ± SD | 57.1 ± 13.8 | 131.9 ± 22.8 | 376.6 ± 64.1 | 498.8 ± 132.8 |
| $T_{max}$, h, median (range) | 1 (1-5) | 3 (1-5) | 1 (1-4) | 1 (1-8) |
| $C_{min}$, µg/mL, mean ± SD | 2.7 ± 4.1 | 28.0 ± 12.3 | 102.8 ± 28.2 | 150.7 ± 47.4 |
| $V_{ss}$, L, mean ± SD | 4.75 ± 1.19 | 4.35 ± 0.17 | 3.36 ± 0.36 | 4.46 ± 1.22 |
| $AUC_T$ µg/mL * h, mean ± SD | 6694 ± 3746 | 21225 ± 6505 | 68145 ± 12811 | 87535 ± 21575 |
| Ratio__AUC, mean ± SD | 1.42 ± 0.46 | 1.37 ± 0.39 | 1.70 ± 0.36 | 1.70 ± 0.18 |
| Ratio__$C_{max}$, mean ± SD | 1.11 ± 0.17 | 1.21 ± 0.22 | 1.25 ± 0.12 | 1.33 ± 0.18 |

$AUC_T$, area under the concentration-time curve within one complete dosing interval;
$C_{max}$, maximum serum concentration,
$C_{min}$, through serum concentration;
Ratio__AUC, relative area under the curve [$AUC_T$(Dose period3)/$AUC_T$(Dose period 1)];
Ratio__$C_{max}$, relative maxiumum serum concentration [$C_{max}$(Dose period 3)/$C_{max}$(Dose period 1)];
$t_{max}$, time to reach $C_{max}$;
$V_{ss}$, apparent volume of distribution at steady stage.

After multiple doses, DI17E6 (EMD 525797) maximal serum concentrations and exposure accumulated dose-dependently up to a maximum value (dosing period 3/dosing period 1) of 1.33 and 1.70, respectively, at 1500 mg.

In most patients, CTC concentrations remained stable around baseline values (data not shown). In two patients, considerable decreases in CTC concentrations were observed at around 14 and 42 days after the start of treatment, respectively.

Anti-EMD 525797 antibodies were detected in 4 of 25 (16.0%) evaluable patients. All four patients were in the 250 mg cohort; two patients reverted to seronegative status after two weeks, one patient had no follow-up, and one patient remained seropositive over the entire study period.

The invention claimed is:

1. A method of treating fibrosis and/or a fibrotic disorder, said method comprising:
   determining, based upon a TGF-β-up/abituzumab-down signature ("TUAD") for a patient suffering from fibrosis and/or a fibrotic disorder, that said patient is likely to respond to treatment with anti-αv integrin antibody DI17E6; wherein genes in the TUAD signature are upregulated by TGF-β and down modulated by abituzumab, the genes of the TUAD signature are selected from the group consisting of two or more of COL15A1, COL1A1, COMP, RGS5, COL10A1, COL5A1, IGFBP2, NM_005576, MOXD1, ADRA2A, COL5A2, MMP10, TNFRSF21, ITGA7, TGF-133, MMP11, SPP1, CCL2, and TNC,
   administering an effective dose of said anti-αv integrin antibody DI17E6 to the patient; wherein said anti-αv integrin antibody DI17E6 is abituzumab and comprises
   a light chain variable region (VL) complementarity determining region (CDR)1 comprising the sequence of amino acids 24 to 34 of SEQ ID NO: 1, VL CDR2 comprising the sequence of amino acids 50 to 56 of SEQ ID NO: 1, and VL CDR3 comprising the sequence of amino acids 89 to 97 of SEQ ID NO: 1; and
   a heavy chain variable region (VH) CDR1 comprising the sequence of amino acids 31 to 35 of SEQ ID NO: 2, VH CDR2 comprising the sequence of amino acids 50 to 53 of SEQ ID NO: 2, and VH CDR3 comprising the sequence of amino acids 99 to 107 of SEQ ID NO: 2,
   wherein the fibrosis and/or the fibrotic disorder is systemic sclerosis (SSc).

2. The method according to claim 1, wherein an organ affected by said fibrosis and/or fibrotic disorder is at least one selected from the group consisting of lung, liver, kidney, cardiovascular system and skin.

3. The method according to claim 1, wherein the systemic sclerosis comprises systemic sclerosis of the lung, liver, kidney, cardiovascular system or skin.

4. The method according to claim 1, wherein the systemic sclerosis affects the cardiovascular system, the blood vessels and/or the blood.

5. The method according to claim 1, wherein the systemic sclerosis comprises one or more indications selected from the group consisting of idiopathic pulmonary fibrosis, primary sclerosing cholangitis, non-alcoholic steatohepatitis (NASH), primary focal glomerulosclerosis, primary segmental glomerulosclerosis, diabetic nephropathy, diastolic dysfunction and myelofibrosis.

6. The method according to claim 1, wherein said systemic sclerosis comprises pulmonary fibrosis and/or alveolitis (interstitial lung disease, ILD).

7. The method according to claim 1, wherein a disease to be treated is systemic sclerosis of the lung and/or skin.

8. The method according to claim 7, wherein the systemic sclerosis of the skin is diffuse cutaneous systemic sclerosis (dcSSc) or limited cutaneous systemic sclerosis (lcSSc).

9. The method according to claim 1, wherein a disease to be treated is pulmonary fibrosis, alveolitis (interstitial lung disease, ILD), and/or sclerodermal interstitial lung disease (SSc-ILD).

10. The method according to claim 1, comprising:
    administering the effective dose of said antibody in an amount of 500 mg-3000 mg per month.

11. The method according to claim 1, comprising:
    administering the effective dose of said antibody in an amount of 1000 mg-2000 mg per month.

12. The method according to claim 1, comprising
    administering said antibody, in an amount of about 500 mg per month, about 1000 mg per month, about 1500 mg per month, about 2000 mg per month or about 2500 mg per month.

13. The method according to claim 1, wherein the genes of the TUAD signature are selected from the group consisting of COL15A1, COL1A1, COMP, COL10A1, COL5A1, COL5A2, ITGA7, MMP11, and TNC.

14. The method according to claim 1, wherein the effective dose is administered in a single dose as monotherapy.

15. The method according to claim 1, wherein a difference in expression of the genes in the TUAD signature is induced by the presence of abituzumab when only abituzumab is administered.

* * * * *

SEQUENCE LISTING

```
<160> NUMBER OF SEQ ID NOS: 21

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      DI17E6 light chain polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
```

```
                35                  40                  45
Tyr Tyr Thr Ser Lys Ile His Ser Gly Val Pro Ser Arg Phe Ser Gly
 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Gly Asn Thr Phe Pro Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 447
<212> TYPE: PRT
<213> ORGANISM: Artificial Sequence
<220> FEATURE:
<223> OTHER INFORMATION: Description of Artificial Sequence: Synthetic
      DI17E6 heavy chain polypeptide

<400> SEQUENCE: 2

Gln Val Gln Leu Gln Gln Ser Gly Gly Glu Leu Ala Lys Pro Gly Ala
1               5                  10                  15

Ser Val Lys Val Ser Cys Lys Ala Ser Gly Tyr Thr Phe Ser Ser Phe
             20                  25                  30

Trp Met His Trp Val Arg Gln Ala Pro Gly Gln Gly Leu Glu Trp Ile
         35                  40                  45

Gly Tyr Ile Asn Pro Arg Ser Gly Tyr Thr Glu Tyr Asn Glu Ile Phe
 50                  55                  60

Arg Asp Lys Ala Thr Met Thr Thr Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Phe Leu Gly Arg Gly Ala Met Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Pro Lys Ser Ser Asp Lys Thr
    210                 215                 220

His Thr Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Ala Gln Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      modified IgG1 hinge region peptide

<400> SEQUENCE: 3

Glu Pro Lys Ser Ser Asp Lys Thr His Thr Cys Pro Pro Cys Pro
1               5                   10                  15

<210> SEQ ID NO 4

<400> SEQUENCE: 4

000

<210> SEQ ID NO 5

<400> SEQUENCE: 5

000
```

```
<210> SEQ ID NO 6
<400> SEQUENCE: 6
000

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      heavy chain framework region polypeptide
```

<400> SEQUENCE: 16

Gln Val Gln Leu Gln Gln Ser Gly Ala Glu Leu Ala Glu Pro Gly Ala
1               5                   10                  15
Ser Val Lys Met Ser Cys Lys Ala Ser Gly Tyr Thr Phe Ser
            20                  25                  30

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      heavy chain framework region peptide

<400> SEQUENCE: 17

Trp Val Lys Gln Arg Pro Gly Gln Gly Leu Glu Trp Ile Gly
1               5                   10

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      heavy chain framework region polypeptide

<400> SEQUENCE: 18

Lys Ala Thr Met Thr Ala Asp Thr Ser Ser Ser Thr Ala Tyr Met Gln
1               5                   10                  15
Leu Ser Gly Leu Thr Ser Glu Asp Ser Ala Val Tyr Tyr Cys Ala Ser
            20                  25                  30

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      heavy chain framework region peptide

<400> SEQUENCE: 19

Trp Gly Gln Gly Thr Ser Val Thr Val Ser Ser
1               5                   10

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Gly Asp Ser
1

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 21

Thr Phe Leu Leu Arg Asn
1               5
```